US005807553A

United States Patent [19]

Malcolm

[11] Patent Number: 5,807,553
[45] Date of Patent: Sep. 15, 1998

[54] IMMONOGENIC OLIGOSACCHARIDE COMPOSITIONS

[75] Inventor: Andrew J. Malcolm, Edmonton, Canada

[73] Assignee: Alberta Research Council, Edmonton, Canada

[21] Appl. No.: 647,602

[22] Filed: May 13, 1996

Related U.S. Application Data

[62] Division of Ser. No. 477,497, Jun. 7, 1995.

[51] Int. Cl.$^6$ .................................................. A61K 39/385
[52] U.S. Cl. ................................... 424/193.1; 424/194.1; 424/196.11; 424/197.11; 424/234.1; 530/403; 530/416; 530/417
[58] Field of Search .............................. 424/234.1, 193.1, 424/194.1, 196.11, 197.11; 530/403, 416, 417

[56] References Cited

U.S. PATENT DOCUMENTS

| | | |
|---|---|---|
| 4,619,828 | 10/1986 | Gordon . |
| 4,644,059 | 2/1987 | Gordon . |
| 4,663,160 | 5/1987 | Tsay . |
| 4,673,574 | 6/1987 | Anderson . |
| 4,695,624 | 9/1987 | Marburg et al. . |
| 4,711,779 | 12/1987 | Porro et al. ............................... 424/92 |
| 4,771,127 | 9/1988 | Cryz et al. . |
| 4,882,317 | 11/1989 | Marburg et al. . |
| 5,153,312 | 10/1992 | Porro ..................................... 530/405 |

FOREIGN PATENT DOCUMENTS

| | | |
|---|---|---|
| 1181344 | 1/1985 | Canada . |
| 1261320 | 9/1989 | Canada . |
| 2052323 | 3/1992 | Canada . |
| 0 208 375 | 1/1987 | European Pat. Off. . |
| 0497525 | 1/1992 | European Pat. Off. . |
| 0 497525 A2 | 8/1992 | European Pat. Off. . |
| WO87/06267 | 10/1987 | WIPO . |

OTHER PUBLICATIONS

Anderson, P., *Infect. Immun.*, 39:233–238, 1983.
Anderson, P., Pichichero, M.E., and Insel, R.A., *J. Clin. Invest.*, 76:52–59, 1985a.
Anderson, P., Pichichero, M.E., and Insel, R.A., *J. Pediatr.*, 107:346–351, 1985b.
Anderson, P.W., Pichichero, M.E., Insel, R.A., Betts, R., Eby, R., and Smith, D.J., *J. Immunol.*, 137:1181–1186, 1986.
Anderson, P.W., Pichichero, M.E., Stein, E.C., Porcelli, S., Betts, R.F., Connuch, D.M., Korones, D., Insel, R.A., Zabradnick, J.M., and Eby, R., *J. Immunol.*, 142:2464–2468, 1989.
Avery, O.T. and Goebel, W.F., *J. Exp. Med.*, 50:566–550, 1929.
Barra, A., Dogan, R., Prued'homme, J.L., Bajart, A., Danue, B. and Fritzell, B., *Vaccine*, 11:1003–1006, 1993.
Bixler, G.S. and Pillai, S., "The Cellular Basis of the Immune Response to Conjugate Vaccines" *Conjugate Vaccines. Contributions to Microbiology and Immunology*, J.M. Cruse and R.E. Lewis, Eds., 10:18–47 1989.

Bolan, G., Broome, C.V., Fracklam, R.R., Pitkaytis, B.D., Fraser, D.W., and Schlech, W.F., III, *Ann, Internal Med.*, 104(1):1–6, 1986.
Borgano, J.M., McLean, A.A., Vella, P.P., Canepa, I., Davidson, W.L., and Hilleman, M.R., *Proc. Soc. Exp. Biol. Med.*, 157:148–154, 1978.
Broome, C.V., Facklam, R.R., and Fraser, D.W., *N. Engl. J. Med.*, 303:549–552, 1980.
Bruyn, G.A.W., and van Furth, R., *Eur. J. Clin. Microbiol. Infect. Dis.*, 10:897–910, 1991.
Chudwin, D.S., Artrip, S.C., Korenbilt, A., Schiffman, G., and Rao, S., *Infect. Immun.*, 50:213–217, 1985.
Connelly, K.K., and Starke, J.R., *Sem. Resp. Inf.*, 6:204–216, 1991.
Eby, R., Koster, M., Hogerman, D. and Malinoski, F., "Pneumococcal Conjugate Vaccines", in *Modern Approaches to New Vaccines Including Prevention of AIDS*, E. Norrby, F. Brown, R. Chanock and H. Ginsberg, eds., Cold Spring Harbor Laboratory Press, New York, 1994.
Fattom, A., Lue, C., Szu, S.C., Mestecky, J., Schiffman, G., Brylar, D., Vann., W.F., Watson, D., Kimzey, L.M., Robbins, J.B. and Schneerson, R., *Infect. and Immun.*, 58(7):2309–2312, 1990.
Fattom, A., Vann, W.F., Szu, S.C., Schneerson, R., Robbins, J.B., Chu, C., Sutton, A., Vickers, J.C., London, W.T., Curfman, B., Hardagree, M.C., and Shiloach, *Infect. and Immun.*, 56(9):2292–2298, 1988.
Forrester, H.L., Jahnigen, D.W., and LaForce, F.M., *Am. J. Med.*, 83:425–430, 1987.
Gaur, A., Arunan, K., Singh, O. and Talwar, G.P., *Int. Immunol.*, 2(2):151–155, 1990.
Giebink, G.S., Koskela, M., Vella, P.P., Harris, M. and Chap, T.L., *J. Inf. Dis.*, 167:347–355, 1993.
Goebel, W.F. and Avery, O.T., *J. Exp. Med.*, 50:521–531, 1929.
Hazelwood, M., Nusrat, R., Kumararatne, D.S., Goodal, M., Raykundalia, C., Wang, D.G., Joyce, H.J., Milford–Wards, A., Forte, M. and Pahor, A., *Clin. Ex. Immunol.*, 93:157–164, 1993.
Hakamori, S. and Kannagi, R., Carbohydrate Antigens in Higher Animals, in *Handbook of Experimental Immunology*, vol. 1, D.M. Weir, L. A. Herzenberg, C. Blackwell and L.A. Herzenberg, eds., Blackwell, Oxford, 1986 (Ch. 9):9.1–9.39.
Heidelberger, M. and Avery, O.T., *J. Exp. Med.*, 38:73–79, 1929.
Hilleman, M.R., Carlson, A.J., Jr., McLean, A.A., Vella, P.O., Weibel, R.E., and Woodhour, A.F., *Rev. Infect. Dis.*, 3(suppl):S31–S42, 1981.

(List continued on next page.)

*Primary Examiner*—James C. Housel
*Assistant Examiner*—Jennifer Shaver
*Attorney, Agent, or Firm*—Burns, Doane, Swecker & Mathis, L.L.P.

[57] ABSTRACT

The invention provides immunogenic oligosaccharide compositions and methods of making and using them. In particular, the compositions comprise oligosaccharides covalently coupled to carrier protein, wherein the resultant conjugate has been shown to contain specific immunogenic epitopes and elicits a protectively immunogenic response.

7 Claims, 22 Drawing Sheets

OTHER PUBLICATIONS

Jones, J.K.N. and Perry, M.B., *J. Am. Chem. Soc.,* 79:2787–2793, 1957.

Kenne, L. and Lindberg, B., "Bacterial Polysaccharides" in *The Polysaccharides,* vol. 2, G.O. Aspinall, Ed., Academic Press, New York, 1983, p. 287–362.

Lee, C–J., Banks, S.D. and Li, J.P., *Crit. Rev. Microbio.,* 18(2):89–114, 1991.

Lees, A., Finkelman, F., Inman, J.K., Witherspoon, K., Johnson, P., Kennedy, J. and Mond, J.J., *Vaccine,* 12:1160–1166, 1994.

Lock, R.A., Hansman, D., and Paton, J.C., *Microbial Pathogen.,* 12:137–143, 1992.

Madore, D.V., Jackson, C.L., Phipps, D.C., Penridge Pediatric Association, Popejoy, L.A., Eby, R., and Smith, D.H., *Pediatric.,* 85(3):331–337, 1990.

Malcolm, A.J., Messner, P., Sleytr, U.B., Smith, R.H., and Unger, F.M., Crystalline Bacterial Cell Surface Layers (S–layers) as Combined Carrier/Adjuvants for Conjugate Vaccines, in *Immobilized Macromolecules: Application Potentials,* U.B. Sleytr, P. Messner, D. Pum and M. Sara, Eds., pp. 195–207, Springer–Verlag, London, 1993a.

Malcolm, A.J., Best, M.W., Szarka, R.J., Mosleh, Z., Unger, F., M., Messner, P. and Sleytr, U.B., Surface Layers of *Bacillus alvei* as a Carrier for a *Streptococcus pneumoniae* Conjugate Vaccine in "Advances in Bacterial Paracrystalline Surface Layers," Ch. 21, pp. 219–233, T.J. Beveridge and S.F. Koval, Ed., Plenum Press, New York, 1993b.

Lindberg, et al., "Structural Studies of the Capsular Polysaccharide from *Streptococcus pneumoniae* Type I", *Carb. Res.,* 78:111–117 (1980).

Marburg, S., Jorn, D., Tolman, R.L., Arison, B., McCauley, J., Kniskern, P.J., Hagopian, A., and Vella, P.O., *J. Am. Chem. Soc.,* 108:5282–5287, 1986.

Mufson, M.A., Hughey, D., and Lydick, E., *J. Infect. Dis.,* 151:749–750, 1985.

Mufson, M.A., Krause, H.E., Schiffman, G., and Hughey, D.E., *Am. J. Med. Sci.,* 293:279–284, 1987.

Nielsen, S.V., and Henrichsen, J., *Scand. J. Infect. Dis.,* 25:165–170, 1993.

Paton, J.C., Lock, R.A., Lees, C–J., Li, J.P., Berry, A.M., Mitchell, T.J., Andrew, P.W., Hansman, D., and Boulnois, G.J., *Infection and Immunity,* 59(7):2297–2304, 1991.

Peeters, C.C.A.M., Tenbergen–Meekes, A–M., Poolman, J.T., Berutett, M., Zegers, B.J.M. and Rijkers, G.T., *Infection and Immunity,* 59(10):3504–3510, 1991.

Perlmutter, R.M., Hansburg, D., Briles, D.E., Nicolotti, R.A., and Davie, J.M., *J. Immunol.,* 121(2):566–572, 1978.

Sanders, L.A.M., Rijkers, G.T., Kuis, W., Tenbergen–Meekes, A.J., de Graff–Meeker, B.R., Hiemstra, I. and Zegers, B.J.M., *J. Allergy Clin. Immunol.,* 91:110–119, 1993.

Shildt, R.A., Boyd, J.F., McCracken, J.D., Schiffman, G., and Giolma, J.P., *Med. Pediatr. Oncol.,* 11:305, 1983.

Schneerson, R., Barrera, O., Sutton, A., and Robins, J.B., *J. Exp. Med.,* 152:361–376, 1980.

Schneerson, R., Robbins, J.B., Chu, C., Sutton, A., Vann, W., Vickers, J.C., London, W.T., Curfman, B., and Hardegree, M.C., *Infection and Immunity,* 45(3):582–591, 1984.

Schneerson, R., Robbins, J.B., Parke, J.C., Bell, C., Schlesselman, J.J. Sutton, A., Wang, Z., Schiffman, G., Karpas, A., and Shiloach, J., *Infection and Immunity,* 52(2):519–528, 1986.

Schneerson, R., Levi, L., Robbins, J.B., Bryla, D.M., Schiffman, G., and Lagergard, T., *Infection and Immunity,* 60(9):3528–3532, 1992.

Seid, R.C., Jr., Boykins, R.A., Liu, D.F., Kibrough, K.W., Hsieh, C.L., Eby, R., *Glycoconj. J.,* 6:489–498, 1989.

Sell, S.H., Wright, P.F., Vaugh, W.K., Thompson, J., and Schiffman, G., *Rev. Infect. Dis.,* 3(suppl):S97–S107, 1981.

Shapiro, E.D., and Clemens, J.D., *Ann. Intern. Med.,* 101:325–330, 1984.

Shapiro, E.D., *N. Engl. J. Med.,* 316:1272–1273, 1987.

Shapiro, E.D., "Pneumococcal Vaccine", in *Vaccines and Immunotherapy,* S.J. Fryz Jr., ed., Pergamon Press, New York, 1991, Ch. 10: pp. 127–139.

Siber, G.R., Weitzman, S.A., Aisenberg, A.C., Weinstein, H.J., and Schiffman, G., *N. Engl. J. Med.,* 299(9):442–448, 1978.

Simberkoff, M.S., Cross, A.P., Al–Ibrahim, M., Baltch, A.L., Geiseler, P.J., Nadler, J., Richmond, A.S., Smith, R.P., Schiffman, G., and Shepard, D.S., *N. Engl. J. Med.,* 315(21):1318–1327, 1986.

Simberkoff, M.S., "Pnuemococcal Vaccine in Adults", in *Immunization,* Ch. 10:125–135, M.A. Sande, and R.K. Root, ed., Churchill Livingstone, New York,, 1989.

Sims, R.V., Steinman, W.C., McConville, J.H., King, L.K., Zwick, W.C., and Schwartz, J.C., 1988, *Ann. Intern. Med.,* 108(5):653–657, 1988.

Slack, J., Der–Balian, G.P., Nahm, M. and Davie, J.M., *J. Exp. Med.,* 151:853–862, 1990.

Sorensen, U. B.S., *J. Clin. Micro.,* 31:2097–2100, 1993.

Sloyer, J.L., Jr., Ploussard, J.H., and Howie, V.M., 1981, *Rev. Infect. Dis.,* 3(suppl):S119–S123, 1981.

Stein, K.E., *J. Inf. Dis.,* 162:S49–S52, 1992.

Stein, K.E., *Int. J. Tech. Assess. Health Care,* 10(1):167–176, 1994.

Stein, K.E., Zopf, D.A., Johnson, B.M., Miller, C.B. and Paul, W. E., *J. Immunol.,* 128:1350–1354, 1982.

Stein, K.E., Zopf, D.A., and Miller, C.B., *J. Exp. Med.,* 157:657–666, 1983.

Steinhoff, M.C., Edwards, K., Keyserling, H., Thomas, M.L., Johnson, C., Madore, D. and Hogerman, D., *Pediatr. Infect. Dis. J.,* 13:368–372, 1994.

Paoletti, L. et al., "Group B Streptococcus Type II Polysaccharide–Tetanus Toxoid Conjugate Vaccine", *Infection and Immunity,* 60(10):4009–14, Oct. 1992.

Lee, C. et al., "Pneumococcal Infection and Immunization in Children", *Critical Reviews in Microbiology,* 20(1):1–12, 1994.

Peeters, C., et al., "Pneumococcal Conjugate Vaccines", *Immunology Letters,* 30:267–74, 1991.

De Velasco, E., et al., "Epitope Specificity of Rabbit Immunoglobulin G (IgG) Elicited by Pneumococcal Type 23F Synthetic Oligosaccharide–and Native Polysaccharide–Protein Conjugate Vaccines: Comparison with Human Anti–Polysaccharide 23F IgG", *Infection and Immunity,* 62(3):799–808, Mar. 1994.

Malcolm, A. et al., "Improved Conjugate Vaccines", *Journal of Cellular Biochemistry,* Supplement 17C, Feb. 8–Mar. 14, 1993.

Svenson et al., *J. Immunol. Methods,* 25:323–335, 1979.

Verheul et al., *Infection & Immun.,* 59(3):843–851, Mar. 1991.

Bhattacharjee, A.K. et al., "Structural Determination of the Sialic Acid Polysaccharide Antigens of *Neisseria meninigitidis* Serogroups B and C eith Carbon 13 Nuclear Magnetic Resonance", *Journal of Biological Chemistry*, 250(5): 1926–1932 (1975).

Cruse, J.M. et al., "Contemporary Trends in Conjugate Vaccines Development", *Contrib. Microbiol. Immunol.*, J.M. Cruse and E.R. Lewis, Eds., 10:1–10 (1989).

Garner, C.V. et al., "Immunologic Considerations for the Development of Conjugate Vaccines", *Contrib. Microbiol. Immunol.*, J.M. Cruse and E.R. Lewis, Eds., 10:11–17 (1989).

Jennings, H.J. et al., "Structural Determination of the Capsular Polysaccharide of *Streptococcus pneumoniae* Type–19 (19F)", *Can. J. Chem.*, 58:1069–1074 (1980).

Jennings, H.J. et al., "Structure of the Complex Polysaccharide C–Substances from *Streptococcus pneumoniae* Type 1", *Biochemistry*, 19:4712–4719 (1980).

Kabat, E.A., "Carbohydrates as Antigens and Immunogens: Size, Shape and Nature of Carbohydrate Epitopes and Idiotopes Polysaccharde Vaccines", R. Bell and G. Torrigiani (eds.), Towards Better Carbohydrate Vaccines, pp. 75–97 (1987).

Kenne, L. et al., "Structural Studies of the Capsular Antigen From *Streptococcus pneumoniae* Type 26" in *Carbohydrate Research*, 73:175–182 (1979).

Klein, David L., "PneumococcalConjugate Vaccines: Review and Update" Microbial Drug Resistance, 1(1):49–58 (1995).

Klein, J.O., "Otitis Externa, Otitis Media, Mastoiditis" Mandell, G.L. et al. (eds) in *Principals and Practice of Infectious Diseases*, Ch. 43:579–585 (1995).

Klugman, K.P. et al., "Antibiotic–Resistant Pneumococci in Pediatric Disease" in *Microbial Drug Resistance* 1(1):5–8 (1995).

Lindberg, B. et al., "Structrual Studies of the Specific Type–14 Pneumococcal Polysaccharide", *Carbohydrate Research*, 58:177–186 (1977).

Malcolm, A.J. et al., "Improved Glyco–Conjugates as Vaccines", Abstracts, No. D1.17, p. 503 (1994).

Moreno, C., "Carbohydrates as Immunogens and Tolerogens, Antibody versus Cell–Mediated Immune Response" in *Towards Better Carbohydrate Vaccines*, Ch. 19:263–277 (1987).

O'Brien, T.P. et al., "Conjunctivitis" G.L. Mandell et al. (eds), in *Principles and Infectious Diseases*, in Ch. 92:1103–1110 (1995).

Ohno, N. et al., "The Structure of the Type–Specific Polysaccharide of Pneumococcus Type XIX" in *Carbohydrate Research*, 80:297–304 (1980).

Richards et al., "Structure of the Specific Capsular Polysaccharide of StreptOcoccus pneumoniae Type 23F (American type 23)", *Biochem. Cell Biol.*, 66: 758–771 (1987).

Robbins, J.B. et al., "Studies of Carbohydrate Antigens of Bacterial Pathogens" R. Bell and G. Torrigiani (eds.), *Towards Better Carbohydrate Vaccines*, pp. 185–201 (1987).

PCT Search Report mailed Oct. 4, 1996.

Penney, et al., International Patent Application Publication No. WO 92/04915, published Apr. 2, 1992.

Paoletti, L.C. et al., "Effects of Chaing Length on the Immunogenicity in Rabbits of Group B Streptococcus Type III Oligosaccharide–Tetanus Toxoid Conjugates", *The Journal of Clinical Investigation*, 89:203–209 (1992).

Peeters et al. 1991 Imm. Letters 30: 267–274.

Lee et al. 1994. Crit. Rev. Microbiol. 20(1):1–12.

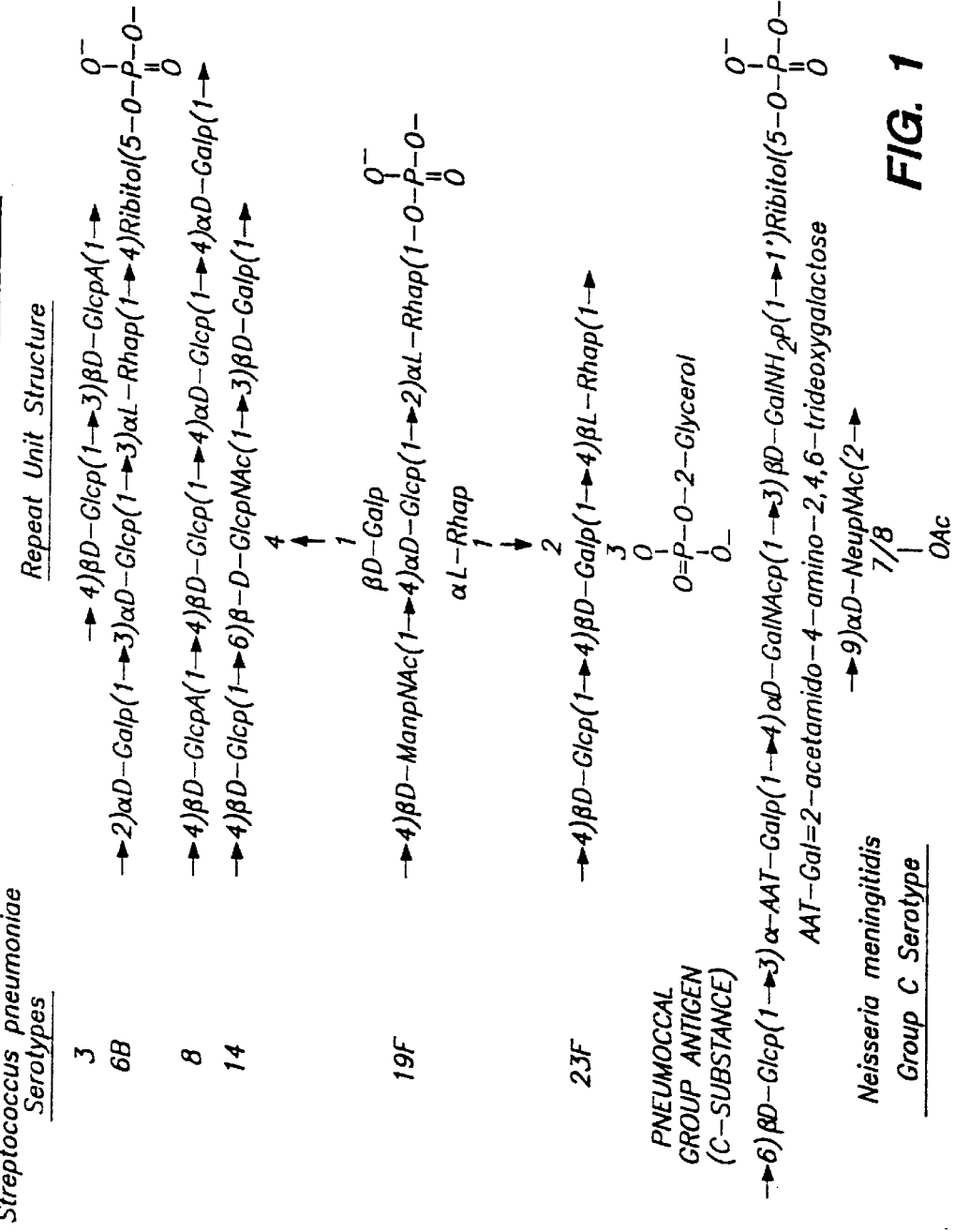

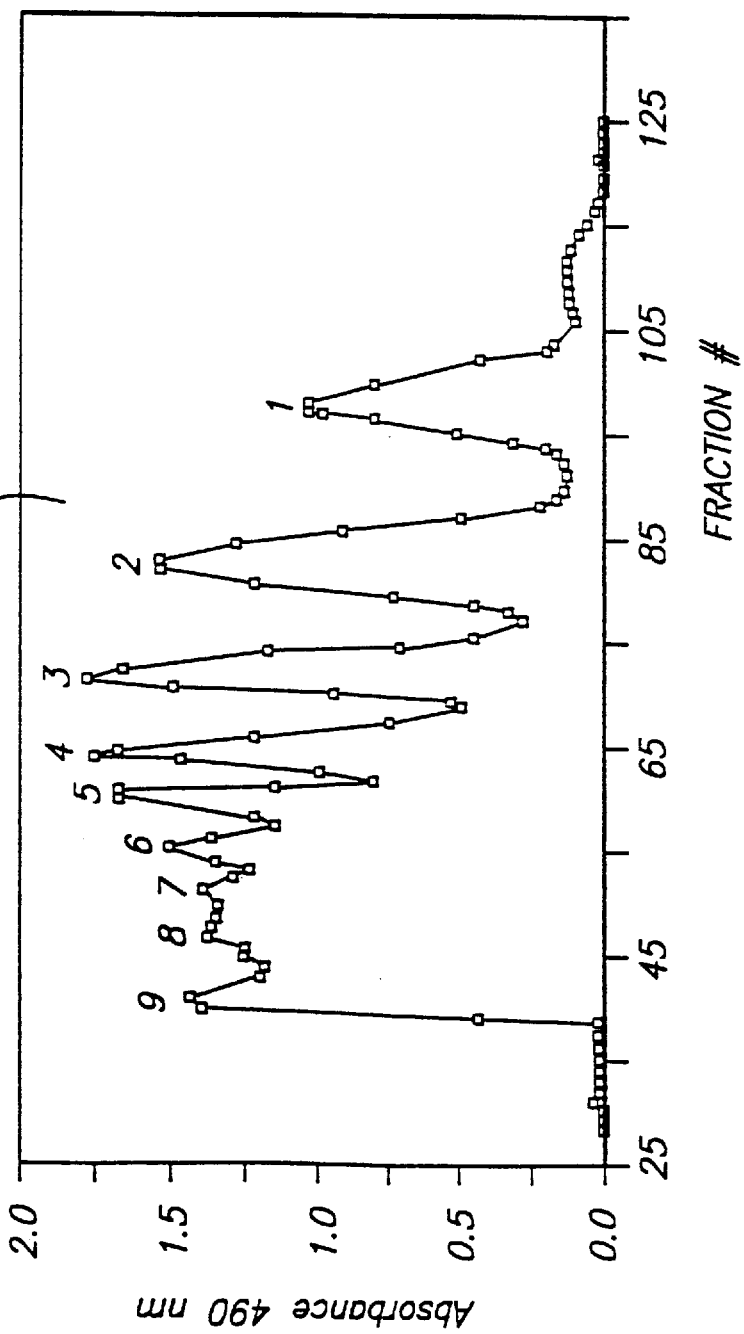

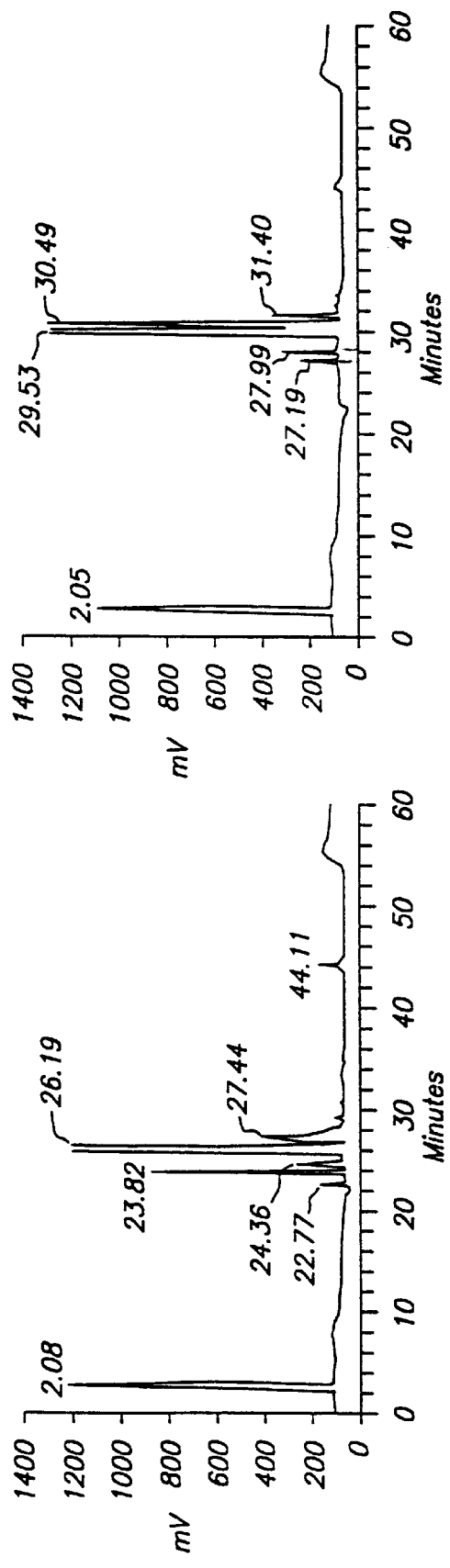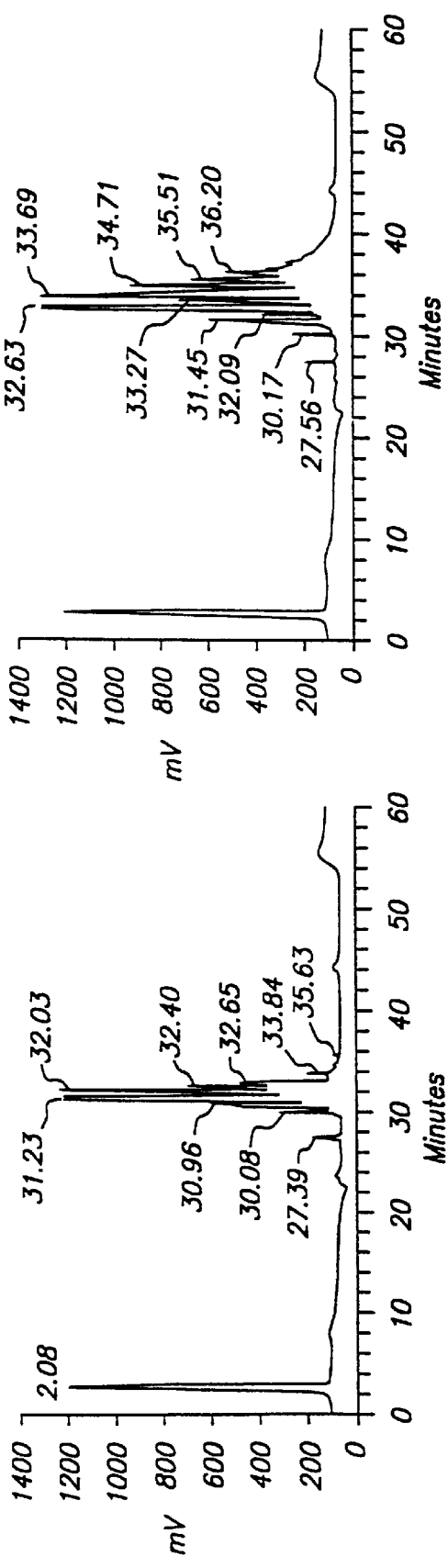

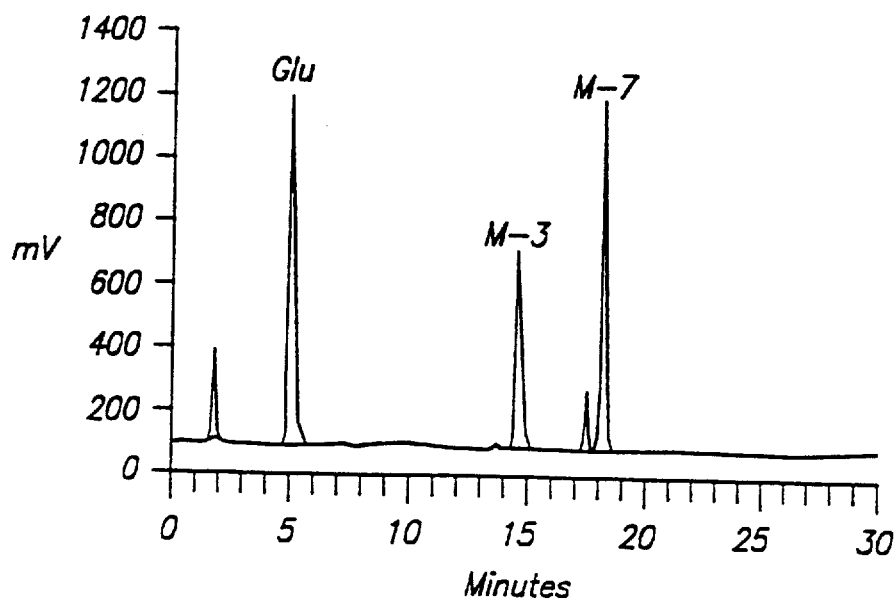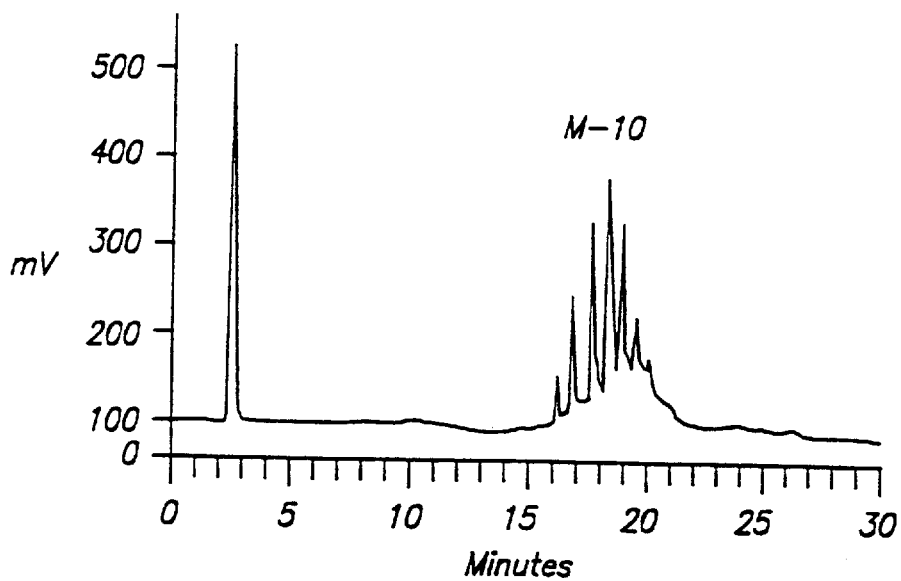
Dionex method and HPLC profiles showing retension times of glucose, maltotriose (M-3), maltoneotaose (M-7) and maltooligosaccharide (M-10) standards (Sigma Chemical Co.) used to determine size of oligosaccharide repeat units.
FIG. 4

Dionex method and HPLC profiles showing retention times of ribitol, rhamnose, galactose, glucose and mannose monosaccharide standards used to determine the carbohydrate content of hydrolysed repeat units.

ACIDIFICATION OF OLIGOSACCHARIDE FOR CARBODIIMIDE COUPLING
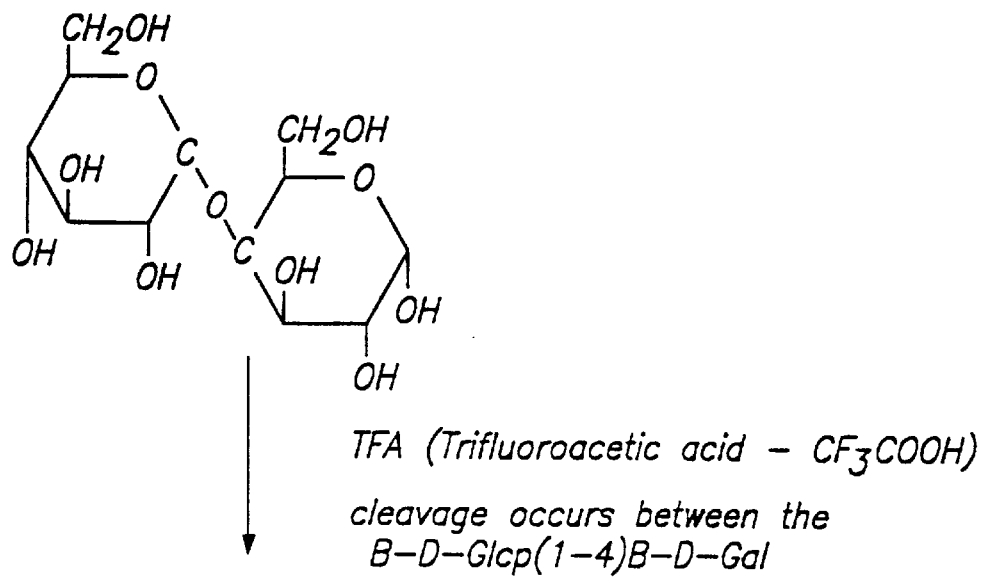
TFA (Trifluoroacetic acid – $CF_3COOH$)
cleavage occurs between the
B-D-Glcp(1-4)B-D-Gal
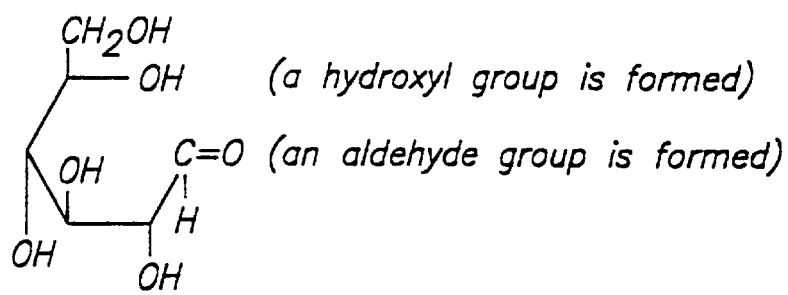
(a hydroxyl group is formed)
C=O (an aldehyde group is formed)
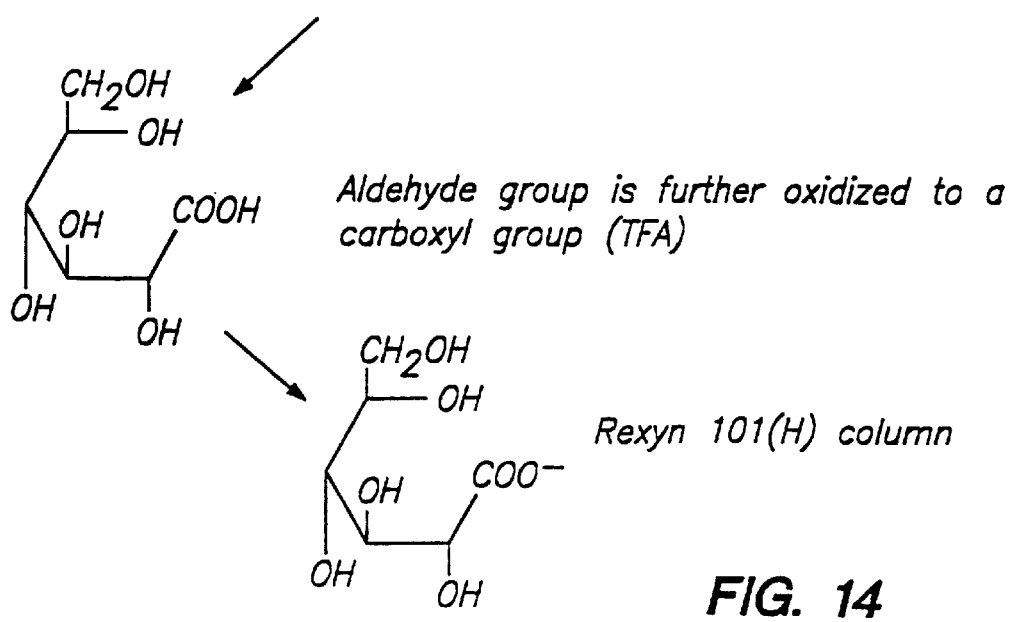
Aldehyde group is further oxidized to a carboxyl group (TFA)
Rexyn 101(H) column
FIG. 14

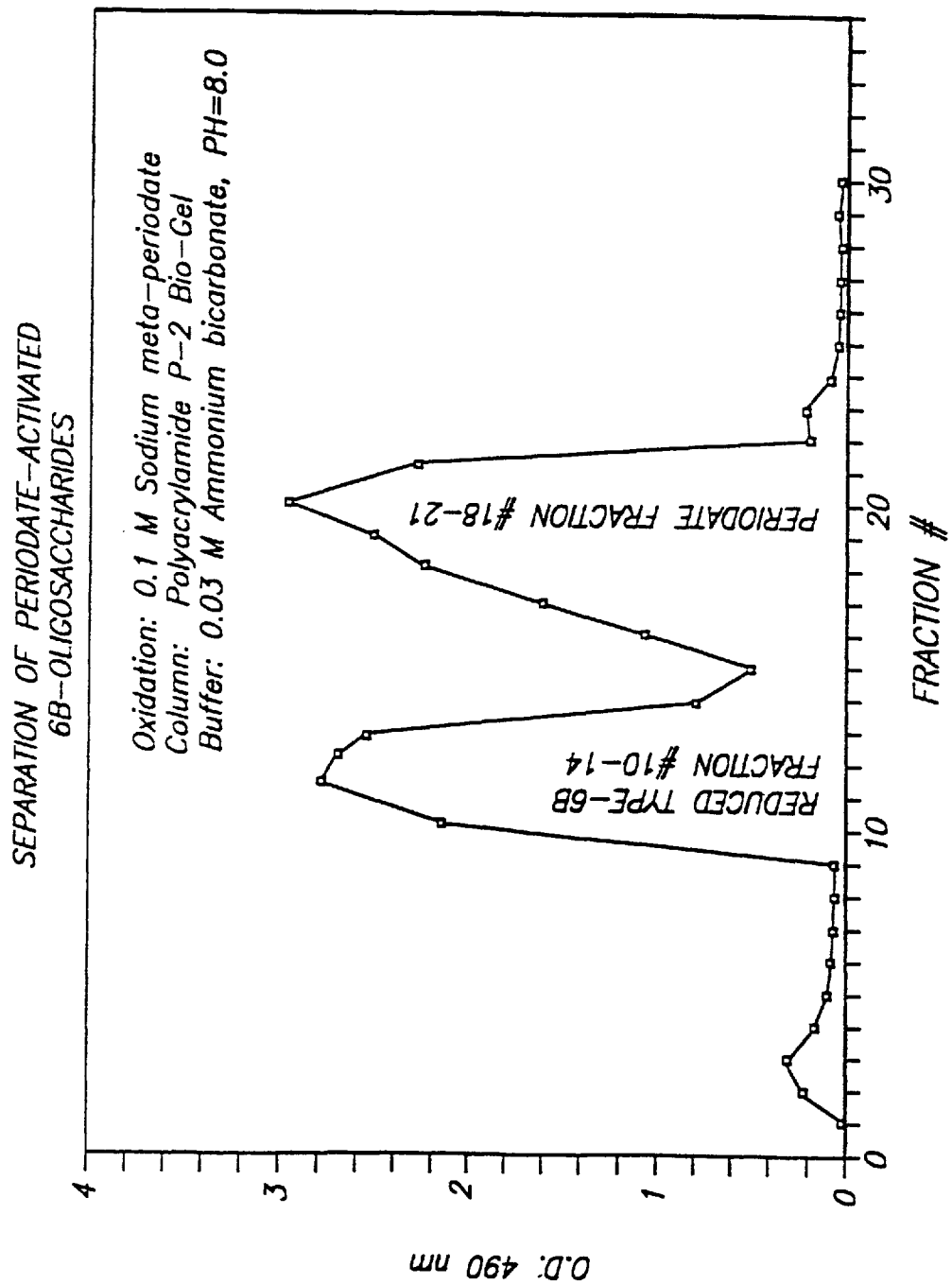

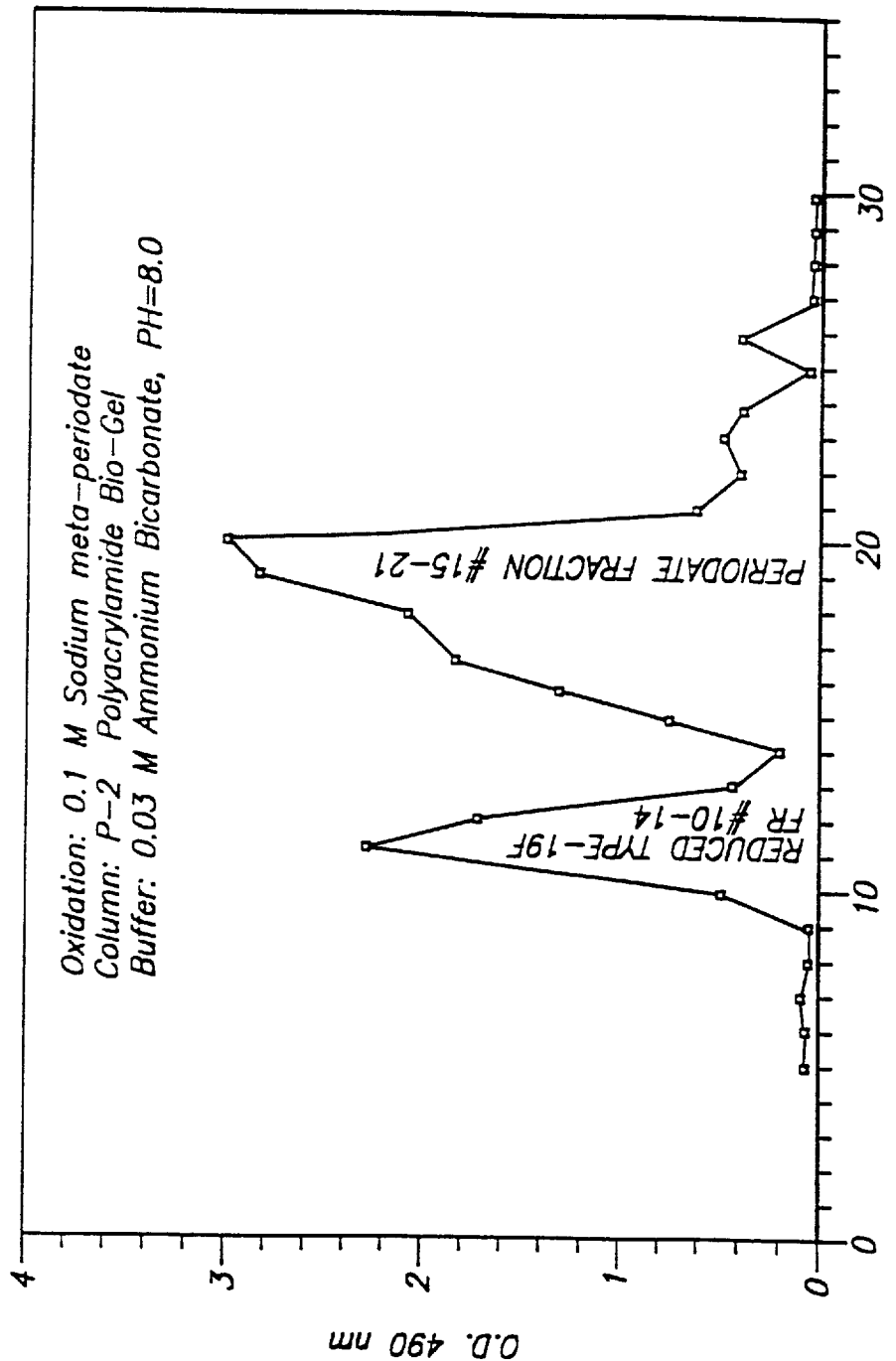

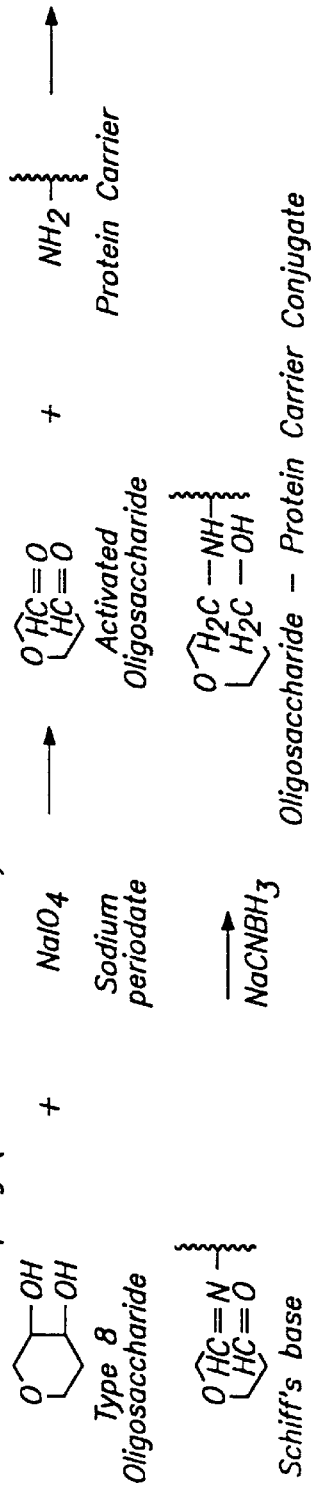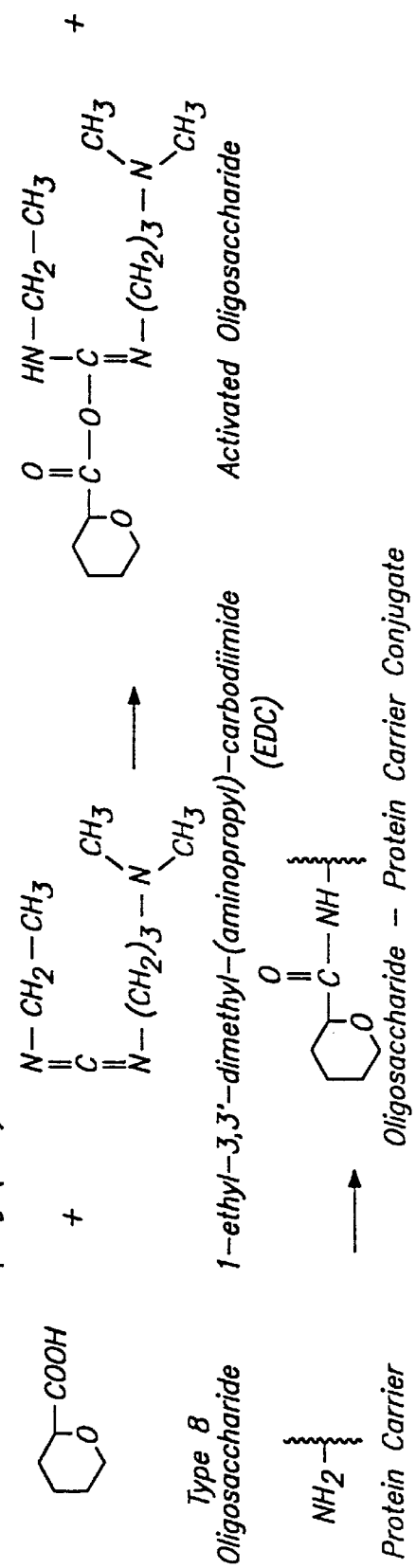

FIG. 18

COUPLING REACTIONS

1. Periodate Coupling (reductive amination)

1) Oxidative amination by sodium periodate activates diol groups in the oligosaccharide and with the addition of an amino group found on the protein carrier, an intermediate (Schiff's base) is formed. Reductive amination by sodium cyanoborohydride protonates the Schiff's base, resulting in the formation of a stable oligosaccharide-protein carrier conjugate.

2. Carbodiimide Coupling (EDC)

2) Carbodiimide activation of carboxyl groups in the oligosaccharide reacts with amino groups found on the protein carrier to form carbohydrate-protein conjugates.

IMMONOGENIC OLIGOSACCHARIDE COMPOSITIONS

This application is a divisional of application Ser. No. 08/477,497, filed Jun. 7, 1995.

FIELD OF THE INVENTION

This application relates to immunogenic oligosaccharide compositions and methods of making and using them. In particular, the compositions comprise oligosaccharides covalently coupled to carrier protein, wherein the resultant conjugate elicits an immunoprotective response.

REFERENCES

The following references are cited in the application at the relevant portion of the application.

Anderson, P., Infect. Immun. 39:233, 1983

Anderson, P. W., Immunogenic Conjugates, U.S. Pat. No. 4,673,574, 1987.

Anderson, P., Pichichero, M. E., and Insel, R. A., J. Clin. Invest. 76:52, 1985a.

Anderson, P., Pichichero, M. E., and Insel, R. A., J. Pediatr. 107:346, 1985b.

Anderson, P. W., Pichichero, M. E., Insel, R. A., Betts, R., Eby, R., and Smith, D. J., J. Immunol. 137:1181, 1986.

Anderson, P. W., Pichichero, M. E., Stein, E. C., Porcelli, S., Betts, R. F., Connuch, D. M., Korones, D., Insel, R. A., Zabradnick, J. M., and Eby, R., J. Immunol. 142:2464, 1989.

Avery, O. T. and Goebel, W. F., J. Exp. Med. 50:533, 1929.

Barro, A., Dogan, R., Prued'homme, J. L., Bajart, A., Danue, B. and Fritzell, B., Vaccine, II:1003, 1993.

Bixler, G. S. and Pillai, S., The cellular basis of the immune response to conjugate vaccines in "Conjugate Vaccines. Contributions to microbiology and immunology", J. M. Creese and R. E. Lewis, eds., Kargen, Basel, 1989.

Bolan, G., Broome, C. V., Fracklam, R. R., Pitkaytis, B. D., Fraser, D. W., and Schlech, W. F, III, Ann. Internal Med. 104:1, 1986.

Borgano, J. M., McLean, A. A., Vella, P. P., Canepa, I., Davidson, W. L., and Hilleman, M. R., Proc. Soc. Exp. Biol. Med. 157:148, 1978.

Broome, C. V., Facklam, R. R., and Fraser, D. W., N. Engl. J. Med. 303:549, 1980.

Bruyn, G. A. W., and van Furth, R., Eur. J. Clin. Microbiol. Infect. Dis., 10:897, 1991.

Chudwin, D. S., Artrip, S. C., Korenbilt, A., Schiffman, G., and Rao, S., Infect. Immun. 50:213, 1985.

Connelly, K. K., and Starke, J. R., Sem. Resp. Inf. 6:209, 1991.

Cryz, S. J., and Fürer, E., Conjugate vaccine against infections by gram-negative bacteria, method for its preparation and use, U.S. Pat. No. 4,771,127, 1988.

Eby, R., Koster, M., Hogerman, D. and Malinoski, F., Pneumococcal Conjugate Vaccines, in "Modern Approaches to New Vaccines Including Prevention of AIDS", E. Norrby, F. Brown, R. Chanock and H. Ginsberg, eds., Cold Spring Harbor Laboratory Press, New York, 1994.

Fattom, A., Lue, C., Szu, S. C., Mestecky, J., Schiffman, G., Brylar, D., Vann., W. F., Watson, D., Kimzey, L. M., Robbins, J. B. and Schneerson, R., Infect. and Immun. 58:2309, 1990.

Fattom, A., Vann, W. F., Szu, S. C., Schneerson, R., Robbins, J. B., Chu, C., Sutton, A., Vickers, J. C., London, W. T., Curfman, B., Hardagree, M. C., and Shiloach, J. Infect. Immun. 56:2292, 1988.

Forester, H. L., Jahnigen, D. W., and LaForce, F. M., Am. J. Med. 83:425, 1987.

Gaur, A., Arunan, K., Singh, O. and Talwar, G. P., Int. Immunol. 2:151, 1990.

Giebink, G. S., Koskela, M., Vella, P. P., Haris, M. and Chap, T. L., J. Inf. Dis. 167:347, 1993.

Goebel, W. F. and Avery, O. T., J. Exp. Med. 50:521, 1929.

Gordon, L. K., Polysaccharide-exotoxoid conjugate vaccines, U.S. Pat. No. 4,619,828, 1986.

Gordon, L. K., Haemophilus influenzae b polysaccharide-diphtheria toxoid conjugate vaccine, U.S. Pat. No. 4,644,059, 1987.

Hazelwood, M., Nusrat, R., Kumararatne, D. S., Goodal, M., Raykundalia, C., Wang, D. G., Joyce, H. J., Milford-Wards, A., Forte, M. and Pahor, A., Clin. Exp. Immunol. 93:157, 1993.

Hakamori, S. and Kannagi, R., Carbohydrate antigens in higher animals, in "Handbook of experimental immunology—vol. 1", D. M. Weir, L. A. Herzenberg, C. Blackwell and L. A. Herzenberg, eds., Blackwell, Oxford, 1986.

Heidelberger, M. and Avery, O. T., J. Exp. Med. 38:73, 1923.

Hilleman, M. R., Carlson, A. J., Jr., McLean, A. A., Vella, P. P., Weibel, R. E., and Woodhour, A. F., Rev. Infect. Dis. 3 (suppl):S31, 1981.

Jennings, H. J., and Lugowski, C., Immunogenic polysaccharide-protein conjugates, Canadian Patent No. 1,181,344, 1985.

Jennings, H. J., Roy, R., and Gamian, A. J., Modified meningococcal group b polysaccharide for conjugate vaccine, Canadian Patent No. 1,261,320, 1989.

Jones, J. K. N. and Perry, M. B., J. Am. Chem. Soc. 79:2787, 1957.

Kenne, L. and Lindberg, B., Bacterial polysaccharides in "The polysaccharides—Vol 2", G. O. Aspinall, Ed., Academic Press, New York, 1983.

Lee, C.-J., Banks, S. D. and Li, J. P., Crit. Rev. Microbio. 18:89, 1991.

Lees, A., Finkelman, F., Inman, J. K., Witherspoon, K., Johnson, P., Kennedy, J. and Mond, J. J., Vaccine 12:1160, 1994.

Lock, R. A., Hansman, D., and Paton, J. C., Microbial Pathogen. 12:137, 1992.

Madore, D. V., Jackson, C. L., Phipps, D. C., Penridge Pediatric Association, Popejoy, L. A., Eby, R., and Smith, D. H., Pediatric, 85:331, 1990.

Malcolm, A. J., Messner, P., Sleytr, U. B., Smith, R. H., and Unger, F. M., Crystalline bacterial cell surface layers (S-layers) as combined carrier/adjuvants for conjugate vaccines, in "Immobilized Macromolecules: Application Potentials," U. B. Sleytr, P. Messner, D. Pum and M. Sara, eds, Springer-Verlag, London, 1993a.

Malcolm, A. J., Best, M. W., Szarka, R. J., Mosleh, Z., Unger, F. M., Messner, P. and Sleytr, U. B., Surface layers of *Bacillus alvei* as a carrier for a *Streptococcus*

*pneunoniae* conjugate vaccine in "Adances in Bacterial Paracrystalline Surface Layers," T. J. Beveridge and S. F. Koval, eds., Plenum Press, New York, 1993b.

Mandell, G. L., "Principles and Practice of Infectious Diseases," Churchill Livingston, N.Y., 1990.

Marburg, S., Jorn, D., Tolman, R. L., Arison, B., McCauley, J., Kniskern, P. J., Hagopian, A., and Vella, P. O., J. Am. Chem. Soc. 108:5282, 1986.

Marburg, S., Tolman, R. L., and Kniskern, P. J., Covalently-modified polyanionic bacterial polysaccharides, stable covalent conjugates of such polysaccharides and immunogenic proteins with bigeneric spacers, and methods of preparing such polysaccharides and conjugates and of confirming covalency, U.S. Pat. No. 4,695,624, 1987.

Marburg, S., Kniskern, P. J., and Tolman, R. L., Covalently-modified bacterial polysaccharides, stable covalent conjugates of such polysaccharides and immunogenic proteins with bigeneric spacers and methods of preparing such polysaccharides and conjugates and of confirming covalency, U.S. Pat. No. 4,882,317, 1989.

Mufson, M. A., Hughey, D., and Lydick, E., J. Infect. Dis. 151:749, 1985.

Mufson, M. A., Krause, H. E., Schiffman, G., and Hughey, D. E., Am. J. Med. Sci. 293:279, 1987.

Nielsen, S. V., and Henrichsen, J., Scand. J. Infect. Dis. 25:165, 1993.

Paton, J. C., Lock, R. A., Lees, C.-J., Li, J. P., Berry, A. M., Mitchell, T. J., Andrew, P. W., Hansman, D., and Boulnois, G. J., Infect. Immun. 59:2297, 1991.

Peeters, C. C. A. M., Tenbergen-Meekes, A.-M., Poolman, J. T., Berutett, M., Zegers, B. J. M. and Rijkers, G. T., Infect. Immun. 59:3504, 1991.

Penney, C. L., Michon, F., and Jennings, H. J., Improved Vaccine Compositions, WO 92/04951, 1992.

Perlmutter, R. M., Hansburg, D., Briles, D. E., Nicolotti, R. A., and Davie, J. M., J. Immunol. 121:566, 1978.

Porro, M., Oligosaccharide Conjugate Vaccines, Canadian Patent No. 2 052 323, 1992.

Porro, M., and Costantino, P., Glycoproteineic conjugates having trivalent immunogenic activity, U.S. Pat. No. 4,711,779, 1987.

Porro, M., Oligosaccharide conjugate vaccines, U.S. patent application Ser. No. 07/590,649, 1990.

Saunders, L. A. M., Rijkers, G. T., Kuis, W., Tenbergen-Meekes, A. J., de Graff-Meeker, B. R., Hiemstra, I. and Zegers, B. J. M., J. Allergy Clin. Immunol. 91:110, 1993

Schidt, R. A., Boyd, J. F., McCracken, J. D., Schiffman, G., and Giolma, J. P., Med. Pediatr. Oncol. 11:305, 1983.

Schneerson, R., Barrera, O., Sutton, A., and Robins, J. B., J. Exp. Med. 152:361,1980.

Schneerson, R., Robbins, J. B., Chu, C., Sutton, A., Vann, W., Vickers, J. C., London, W. T., Curfman, B., and Hardegree, M. C., Infect. Immun. 45:582, 1984.

Schneerson, R., Robbins, J. B., Parke, J. C., Bell, C., Schlesselman, J. J., Sutton, A., Wang, Z., Schiffman, G., Karpas, A., and Shiloach, J., Infect. Immun. 52:519, 1986.

Schneerson, R., Levi, L., Robbins, J. B., Bryla, D. M., Schiffman, G, and Lagergard, T., Infect. and Immunity 60:3528, 1992.

Seid, R. C., Jr., Boykins, R. A., Liu, D. F., Kibrough, K. W., Hsieh, C. L., Eby, R., Glycoconj. J. 6:489, 1989.

Sell, S. H., Wright, P. F., Vaughn, W. K., Thompson, J., and Schiffman, G., Rev. Infect. Dis. 3 (suppl):S97, 1981.

Shapiro, E. D., and Clemens, J. D., Ann. Intern. Med. 101:325, 1984.

Shapiro, E. D., N. Engl. J. Med. 316:1272, 1987.

Shapiro, E. D., Pneumococcal vaccine, In: "Vaccines and Immunotherapy," S. J. Fryz Jr., ed., Pergamon Press, New York, 1991.

Siber, G. R., Weitzman, S. A., Aisenberg, A. C., Weinstein, H. J., and Schiffman, G., N. Engl. J. Med. 299:442, 1978.

Simberkoff, M. S., Cross, A. P., Al-Ibrahim, M., Baltch, A. L., Geiseler, P. J., Nadler, J., Richmond, A. S., Smith, R. P., Schiffman, G., and Shepard, D. S., N. Engl. J. Med. 315:1318, 1986.

Simberkoff, M. S., Pneumococcal vaccine in adults, In: "Immunization," M. A. Sande, and R. K. Root, ed., Churchill Livingstone, N.Y., 1989.

Sims, R. V., Steinman, W. C., McConville, J. H., King, L. K., Zwick, W. C., and Schwartz, J. C., 1988, Ann. Intern. Med., 108:653., 1988.

Slack, J., Der-Balian, G. P., Nahm, M. and Davie, J. M., J. Exp. Med. 151:853–1980.

Sorensen, U. B. S., J. Clin. Micro. 31:2097, 1993.

Sloyer, J. L., Jr., Ploussard, J. H., and Howie, V. M., 1981, Rev. Infect. Dis. 3 (suppl):S1, 1981.

Stein, K. E., J. Inf. Dis. 165: 549, 1992.

Stein, K. E., Int. J. Tech. Assess, Health Care, 10:167, 1994.

Stein, K. E., Zopf, D. A., Johnson, B. M., Miller, C. B. and Paul, W. E., J. Immunol. 128:1350, 1982.

Stein, K. E., Zopf, D. A. and Miller, C. B., J. Exp. Med., 157:657, 1983.

Steinhoff, M. C., Edwards, K., Keyserling, H., Thoms, M. L., Johnson, C., Madore, D. and Hogerman, D., Pediatr. Infect. Dis. J. 13:368, 1994.

Tsay, G. C., and Collins, M. S., Vaccines for gram-negative bacteria, U.S. Pat. No. 4,663,160, 1987.

The disclosure of the above publications, patents and patent applications are herein incorporated by reference in their entirety to the same extent as if the language of each individual publication, patent and patent application were specifically and individually included herein.

BACKGROUND OF THE INVENTION

Immune Responses to Polysaccharides

Heidelberger and Avery (1923) demonstrated that the type specific antigens of pneumococci are polysaccharides. Bacterial capsular polysaccharides are cell surface antigens composed of identical repeat units which form extended saccharide chains. Polysaccharide structures are present on pathogenic bacteria and have been identified on *Escherichia coli, Neisseria meningitidis, Haemophilus influenzae*, Group A and Group B Streptococcus, *Streptococcus pneumoniae* and other species. (Kenne and Lindberg 1983).

Specific blood group determinants and "tumor-associated" antigens are examples of mammalian cell surface carbohydrates. Oncogenically transformed cells often display surface carbohydrates distinctly different from those of non-transformed cells. These glycans consist of only a few monosaccharides (Hakomori and Kannagi 1986). The glycan structures by themselves are usually not antigenic, but constitute haptens in conjunction with protein or glycoprotein matrices.

A general feature of saccharide antigens is their inability to elicit significant levels of IgG antibody classes (IgG isotypes) or memory responses and, accordingly, they are considered thymus-independent (TI) antigens. Conjunction of polysaccharide antigens or of immunologically inert carbohydrate haptens to thymus dependent (TD) antigens such as proteins enhances their immunogenicity. The protein stimulates carrier-specific T-helper cells which play a role in the induction of anti-carbohydrate antibody synthesis (Bixler and Pillai 1989).

Much of our current knowledge of TI and TD responses comes from studies of pertinent mouse models (Stein et al., 1983; Stein, 1992; Stein, 1994). TI antigens generally elicit low affinity antibodies of restricted class and do not produce immunologic memory. Adjuvants have little effect on response to TI antigens. In contrast, TD antigens elicit heterogeneous and high affinity antibodies with immunization and produce immunologic memory. Adjuvants enhance response to TD antigens. Secondary responses to TD antigens shows an increase in the IgG to IgM ratio, while for TI antigens the secondary response IgG to IgM ratio is one-to-one, similar to that of a primary response (Stein et al., 1982; Stein, 1992 and 1994). In mice and humans, TD antigens elicit predominantly $IgG_1$ isotypes, with some amounts of $IgG_2$ and $IgG_3$ isotypes. TI responses to polysaccharides are restricted to $IgG_3$ of the IgG isotypes (Perlmutter et al., 1978; Slack et al., 1980).

Current Pneumococcal Vaccine

Pneumococci are currently divided into 84 serotypes based on their capsular polysaccharides. Although there is some variability of commonly occurring serotypes with geographic location, generally serotypes 1, 3, 4, 7, 8 and 12 are more prevalent in the adult population. Serotypes 1, 3, 4, 6, 9, 14, 18, 19 and 23 often cause pneumonia in children (Mandell, 1990; Connelly and Starke, 1991; Lee et al., 1991; Sorensen, 1993; Nielsen and Henricksen, 1993).

At present, the most widely used anti-pneumococcal vaccine is composed of purified capsular polysaccharides from 23 strains of pneumococci (Pneumovax® 23, Merck Sharp & Dohme). The pneumococcal capsular types included in Pneumovax® 23 are 1, 2, 3, 4, 5, 6B, 7F, 8, 9N, 9V, 10A, 11A, 12F, 14, 15B, 17F, 18C, 19F, 19A, 20, 22F, 23F, 33F (Danish nomenclature). These serotypes are said to be responsible for 90 percent of serious pneumococcal disease in the world.

Some controversy exists in the literature over the efficacy of the Pneumovax® 23 vaccine (Borgano et al., 1978; Broome et al., 1980; Sloyer et al., 1981,; Shapiro and Clemens, 1984; Bolan et al., 1986; Simberkoff et al., 1986; Forester et al., 1987; Shapiro, 1987; Sims et al., 1988; Simberkoff, 1989; Shapiro, 1991). The pneumococcal vaccine is effective for induction of an antibody response in healthy young adults (Hilleman et al., 1981; Mufson et al., 1985; Bruyan and van Furth, 1991). These antibodies have been shown to have in vitro opsonic activity (Chudwin et al., 1985). However, there is marked variability in the intensity of the response and in the persistence of antibody titers to the different serotypes (Hilleman et al., 1981; Mufson et al., 1987).

Children under 2 years of age are the group at highest risk of systemic disease, otitis media and acute lower respiratory infection caused by pneumococci, but they do not respond to this vaccine (Sell et al., 1981; Hazelwood et al., 1993; Saunders et al., 1993). Furthermore, elderly and immunosuppressed patients have impaired or varied responses to Pneumovax® 23 (Siber et al., 1978; Schildt et al., 1983; Forester et al., 1987; Simberkoff, 1989; Shapiro, 1991). These population groups do not respond well to the thymus independent polysaccharide antigens of this vaccine. Typical of thymus independent antigens, antibody class switching from an IgM to IgG isotype is not usually observed nor is an anamnestic response to a booster immunization (Borgano et al., 1978).

Recent occurrences of antibiotic resistant strains of bacteria stresses the need to develop efficacious vaccines for the prevention of childhood infection. Clearly, new vaccines against pneumococci are needed, especially for high risk groups and children.

Conjugate Vaccines

Avery and Goebel were the first to prepare vaccines against bacterial infections (Avery and Goebel 1929; Goebel and Avery 1929). More recently, several protein carrier conjugates have been developed which elicit thymus dependent responses to a variety of bacterial polysaccharides. To date, the development of conjugate vaccines to *Hemophilus influenzae* type b (Hib) has received the most attention. Schneerson et al. (1980) have covalently coupled Hib polysaccharides (polyribitol-phosphate) to diphtheria toxoid. This group has also developed a Hib vaccine by derivatizing the polysaccharide with an adipic acid dihydrazide spacer and coupling this material to tetanus toxoid with carbodiimide (Schneerson et al., 1986). A similar procedure was used to produce conjugates containing diphtheria toxoid as the carrier (Gordon, 1986 and 1987). A bifunctional spacer was utilized to couple the outer membrane protein of group B *Neissetia meningitidis* to Hib polysaccharides (Marburg et al., 1986, 1987 and 1989). Finally, Anderson (1983 and 1987) has produced a conjugate vaccine using Hib oligosaccharides coupled by reductive amination to a nontoxic, cross-reactive mutant diphtheria toxin $CRM_{197}$.

Reports in the literature differ on the efficacy of these vaccines, and many studies are still in progress. However, oligosaccharide conjugates (Anderson et al., 1985a, 1985b, 1986, 1989; Seid et al., 1989; Madore et al., 1990; Eby et al., 1994) and polysaccharide conjugates (Barra et al., 1993) are reported to be immunogenic in infants and elicit a thymus dependent response. Hapten loading is a key factor for conjugate immunogenicity (Anderson et al., 1989; Eby et al., 1994).

Other conjugate vaccines have been developed by Jennings et al. (1985 and 1989), who utilized periodate activation to couple polysaccharides of *Neisseria meningitidis* to tetanus or diphtheria toxoid carriers. Porro (1987) defined methods to couple esterified *N. meningitidis* oligosaccharides to carrier proteins. Conjugate vaccines containing polysaccharides of *Pseudomonas aeruginosa* coupled by the periodate procedure to detoxified protein from the same organism (Tsay and Collins, 1987) have been developed. Cryz and Furer (1988) used adipic acid dihydrazide as a spacer arm to produce conjugate vaccines against *P. aeruginosa*.

Polysaccharides of specific serotypes of *S. pneumoniae* have also been coupled to classical carrier proteins such as tetanus or diphtheria toxoids (Schneerson et al., 1984; Fattom et al., 1988 and 1990; Schneerson et al., 1992), to *N. meningitidis* membrane protein (Marburg et al., 1987; Giebink et al., 1993) and to a pneumolysin mutant carrier (Paton et al., 1991; Lock et al., 1992; Lee et al., 1994). Technology for coupling *S. pneumoniae* oligosaccharides to $CRM_{197}$ protein has been developed (Porro, 1990). These conjugate vaccines have variable or as yet undetermined immunopotentiation properties. Reproducibility of these coupling technologies with the maintenance of immunogenic epitopes is currently the greatest problem in developing effective *S. pneumoniae* glycoconjugate vaccines. The optimal immunogenic oligosaccharide size appears to vary dependent on the serotype, indicating a conformational aspect of certain immunogenic epitopes (Eby et al., 1994; Steinhoff et al., 1994).

Vaccines to DTP, tuberculosis, polio, measles, hepatitis, Hib and pneumonia which induce long lasting protection are needed. In order to induce protection in infants to *S. pneumoniae*, a multi-hapten protein conjugate containing a high level of oligosaccharides of optimal immunogenic size for each serotype is desired.

Various researchers have proposed enhancement of the immunogenicity of conjugate vaccines by adjuvant administration. Aluminum salt, which is approved for human use, is an example. Carbohydrate moieties, such as beta glucan particles and low molecular weight dextran, have also been reported to possess adjuvant activity. Adjuvax (Alpha-Beta Technology) is an adjuvant composition containing beta glucan particles. Lees et al. (1994) have reported the use of low molecular weight dextran constructs as adjuvants. Penney et al. (1992) have reported a long chain alkyl compound with immunological activity.

BRIEF DESCRIPTION OF THE DRAWINGS

FIG. 1 illustrates the repeat unit structures of the polysaccharides used in the Examples of the invention.

FIG. 2 shows the separation profile of *Streptococcus pneumoniae* serotype 8 capsular polysaccharides through a BioGel P-10 column after acid hydrolysis (0.5M trifluoroacetic acid, 100° C., 20 minutes) resulting in discernible oligosaccharides of one to eight repeat units.

FIGS. 3A–3D shows the relative size of the repeat units in peaks 1, 2, 3 and 4 of hydrolyzed *Streptococcus pneumoniae* serotype 8 capsular polysaccharides, as measured by HPLC analysis.

FIG. 4 shows the HPLC retention times of the glucose, M-3 maltotriose, M-7 maltoheptose, and M-10 malto-oligosaccharide standards used to determine the relative size of various oligosaccharide repeat units.

FIG. 14 illustrates the acidification of oligosaccharides for carbodiimide coupling.

FIG. 16 demonstrates separation of reduced and periodate fractions of oligosaccharides of serotype 6B of *Streptococcus pneumoniae*.

FIG. 17 demonstrates separation of reduced and periodate fractions of oligosaccharides of serotype 19F of *Streptococcus pneumoniae*.

FIG. 18 depicts the periodate and EDC coupling chemistry reactions.

SUMMARY OF THE INVENTION

Figure 5:
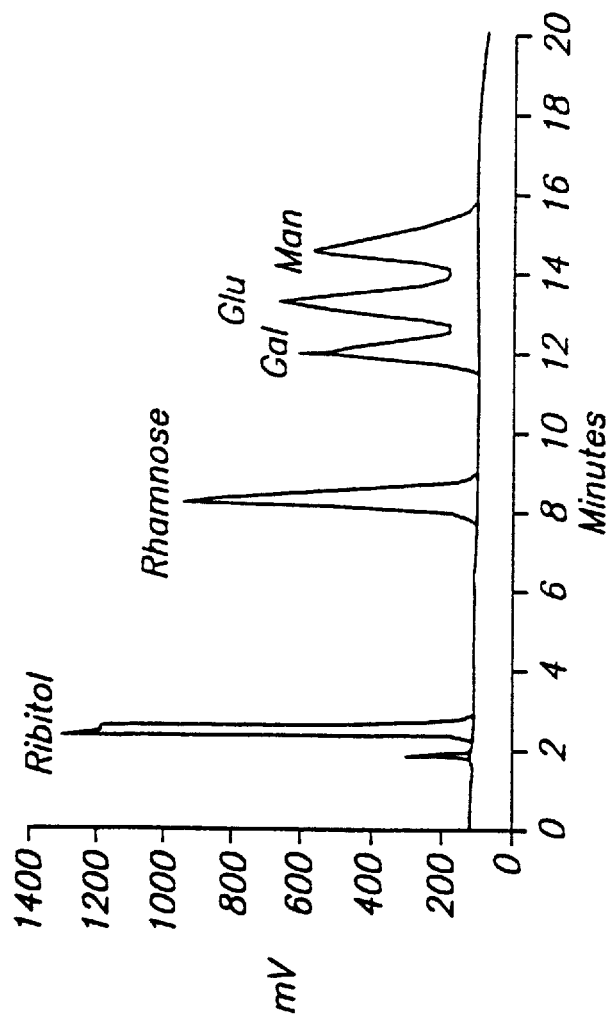
FIG. 5 is an example of the retention times of ribitol, rhamnose, galactose, fucose and mannose monosaccharide standards used to determine carbohydrate content of the hydrolysed repeat unit.
Figure 6:
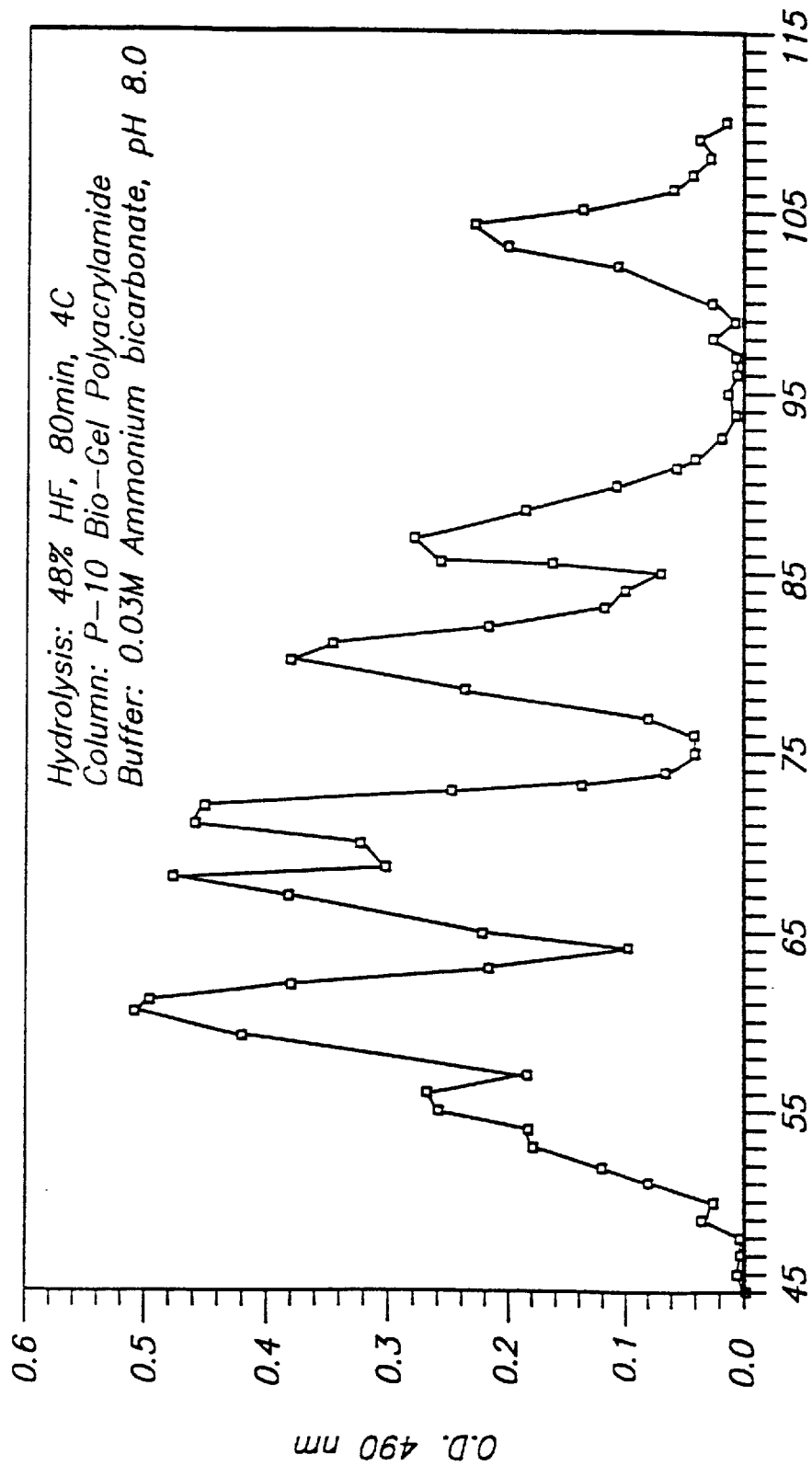
FIG. 6 shows the separation profile of *S. pneumoniae* serotype 6B polysaccharide hydrofluoric acid hydrolysates passed over a P-10 BioGel column.
Figure 7:
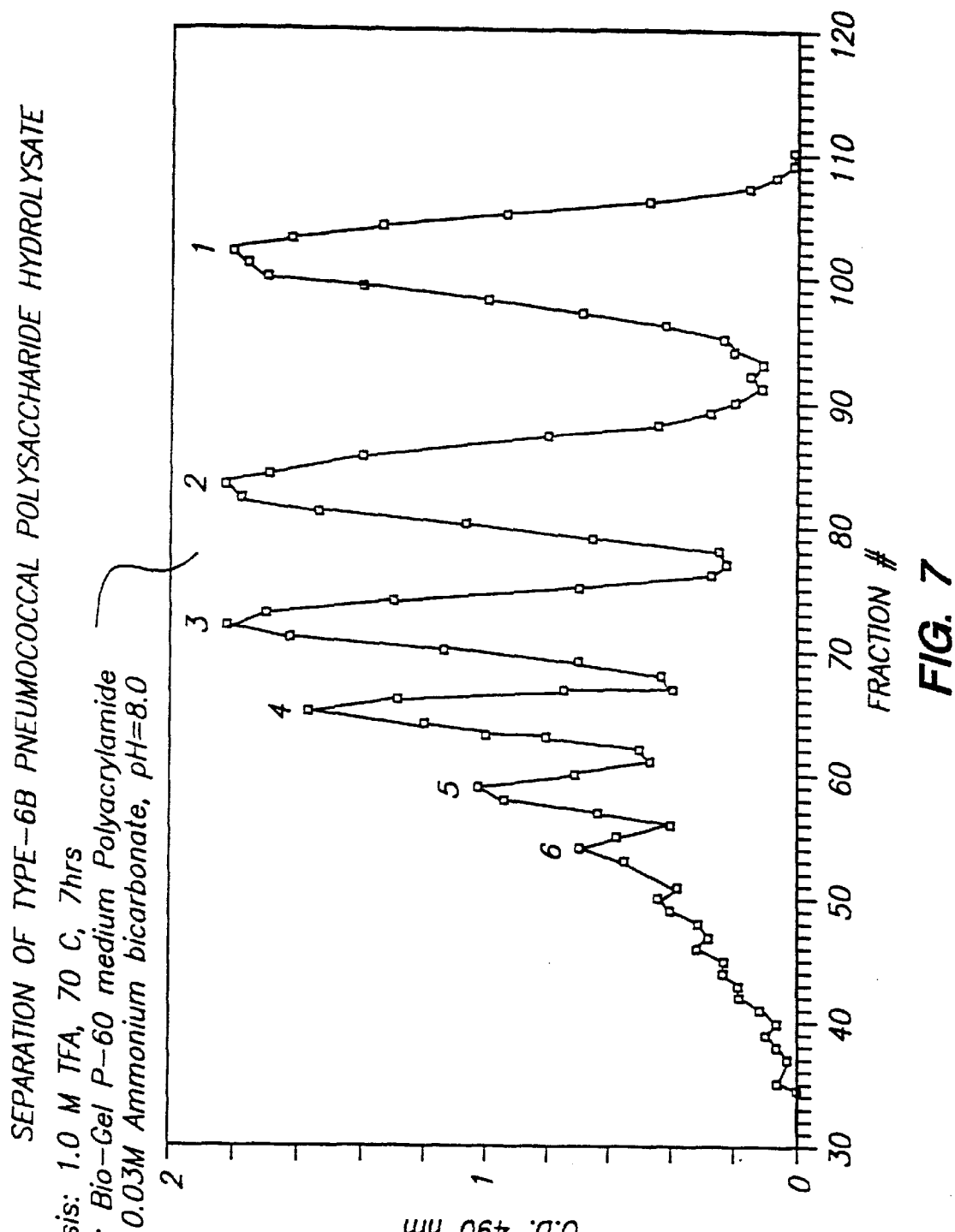
FIG. 7 shows the separation profile of *S. pneumoniae* serotype 6B polysaccharide TFA hydrolysates passed over a P-60 BioGel column.
Figure 8:
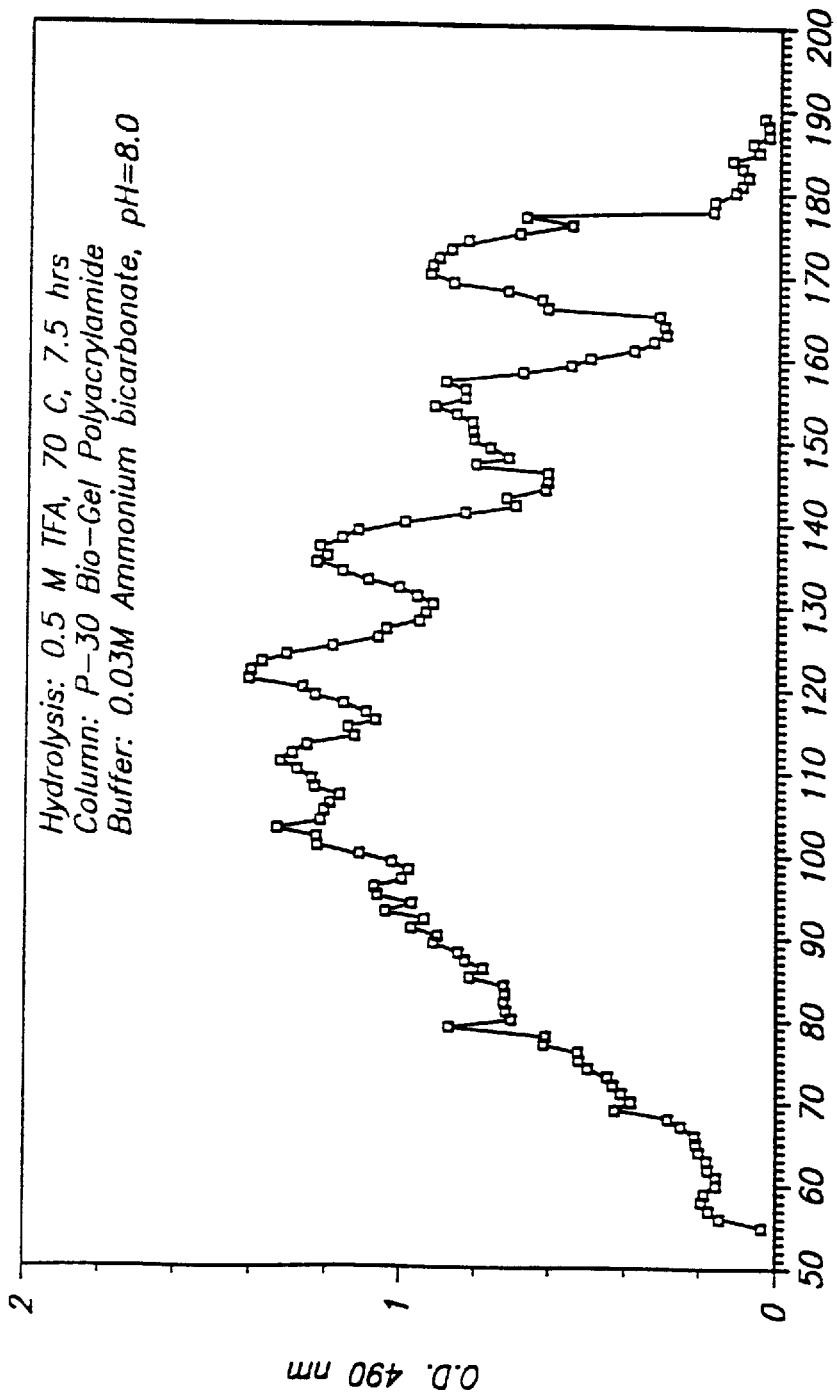
FIG. 8 shows the separation profile of *S. pneumoniae* serotype 14 polysaccharide TFA hydrolysates passed over a P-30 BioGel column.
Figure 9:
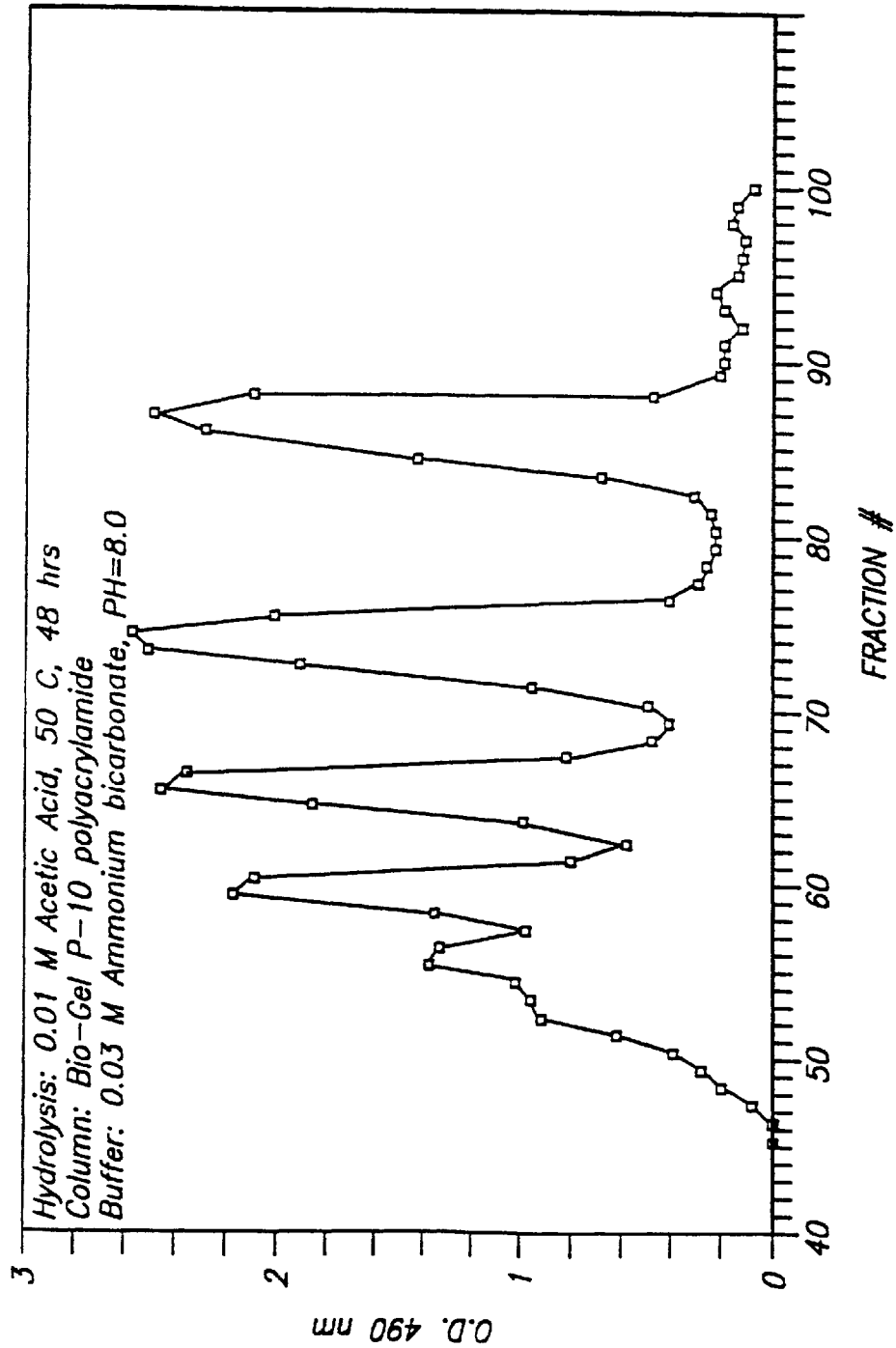
FIG. 9 shows a separation profile of *S. pneumoniae* serotype 19F polysaccharide acetic acid hydrolysates acetic acid passed over a P-10 BioGel column.
Figure 10:
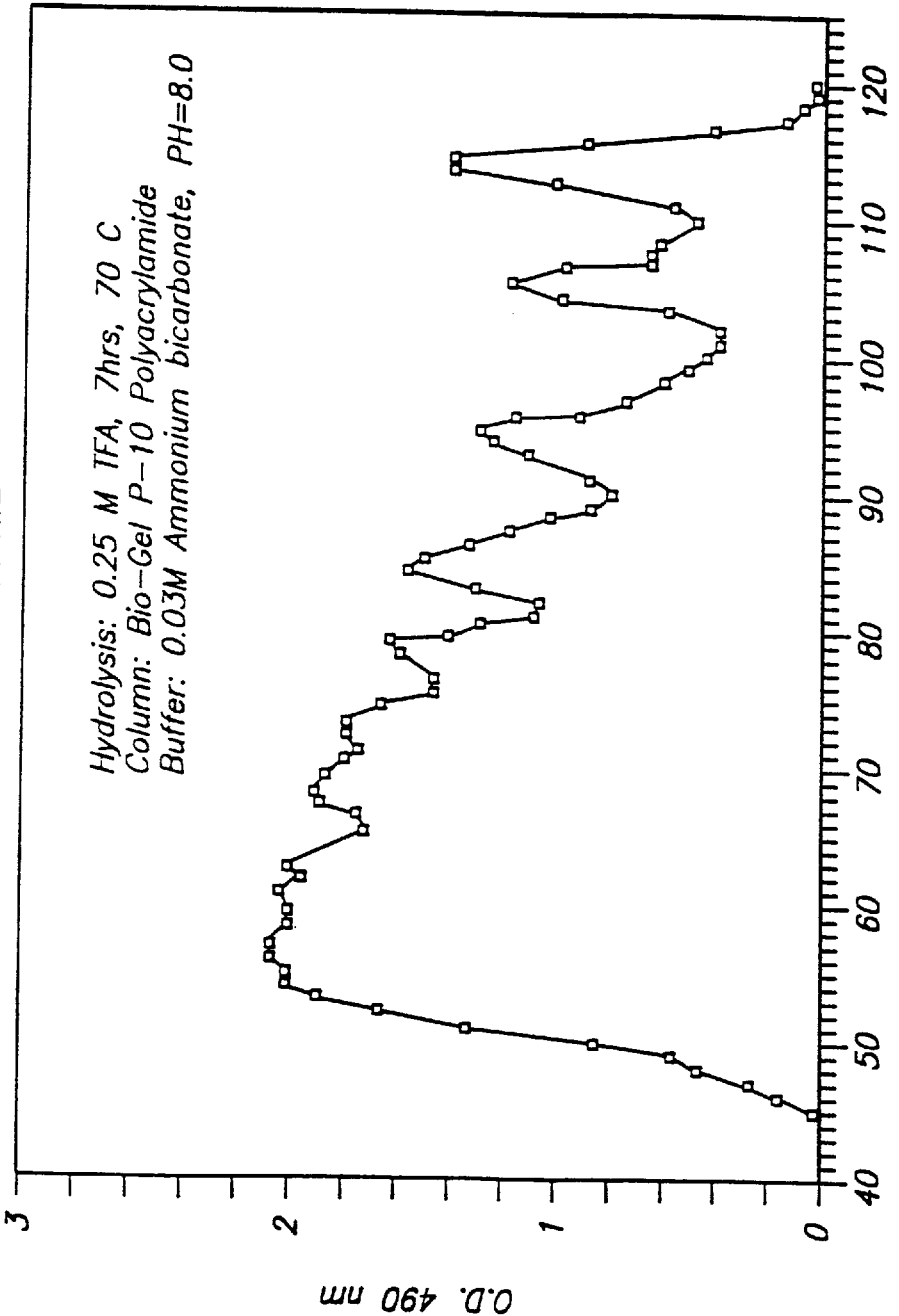
FIG. 10 shows the separation profile of *S. pneumoniae* serotype 23F polysaccharide TFA hydrolysates passed over a P-10 BioGel column.

In one aspect, the invention provides compositions comprising: a) a size-separated carbohydrate hapten comprising at least one immunogenic epitope; and b) a carrier, wherein said hapten is covalently coupled to said carrier and wherein said hapten-carrier conjugate is protectively immunogenic.

In another aspect, the invention provides methods of making conjugate compositions comprising: a) cleaving a bacterial or viral polysaccharide into oligosaccharides so as to preserve immunogenic epitopes on the resulting oligosaccharides; b) separating the resulting oligosaccharides based on size; c) selecting those oligosaccharides which contain immunogenic epitopes based on inhibition ELISA; d) activating the oligosaccharides selected in step c); and e) coupling the activated oligosaccharides to a purified carrier, wherein the resulting composition contains immunogenic epitopes and is protectively immunogenic.

In a further aspect, the invention provides methods of providing protective immunization against a bacterial pathogen comprising administering to a mammal in need of such treatment an effective amount of the vaccine composition described above.

In still a further aspect, the invention provides compositions useful for stimulating an immune response to an antigen, said immunostimulatory composition comprising an oligosaccharide of *S. pneumoniae* serotype 8 and a suitable pharmaceutical carrier, wherein said oligosaccharide provides an immunostimulatory effect.

In a yet further aspect, the invention provides methods of providing protective immunization against a bacterial pathogen comprising administering to a mammal in need of such treatment an effective amount of the composition of the serotype 8 composition described above.

A still further aspect of the invention provides methods of augmenting an immunogenic response to an antigen comprising administering an oligosaccharide of S. pneumoniae serotype 8 which contains an immunogenic epitope as determined by inhibition ELISA along with said antigen.

DETAILED DESCRIPTION OF THE INVENTION

This invention relates to improved methods for preparing oligosaccharide-protein carrier conjugates. The conjugate product may be composed of various haptens or carriers. Mono, di, and multi-hapten conjugates may be prepared. Methods to determine the presence of immunogenic epitopes on the hapten or carrier of the resultant conjugate are described. Such conjugates have utility as vaccines, therapeutic and prophylactic agents, immunomodulators, diagnostic agents, development and research tools.

This invention is particularly suited for developing conjugates as vaccines to such bacterial pathogens including, but not limited to *Streptococcus pneumoniae, Neisseria meningitidis, Haemophilus influenzae* B, Group B Streptococcus, Group A Streptococcus, *Bordetella pertussis, Escherichia coli, Streptococcus mutans, Staphylococcus aureus, Salmonella typhi, Cryptococcus neoformans, Pseudomonas aeruginosa* and *Klebsiella pneumoniae*. Conjugates of this invention convert weakly or non-immunogenic molecules to molecules which elicit specific immunoprotective antibody or cellular responses.

Poor immune responses to polysaccharide vaccines (thymus independent antigens, TI) have been observed with high risk groups, such as the elderly and children under 2 years of age. Several investigators are attempting to elicit thymus dependent (TD) responses to a variety of bacterial polysaccharides using protein carriers. Integrity of critical immunogenic epitopes and inconsistency of covalent linkage between the carbohydrate and protein are major limitations with these conjugate vaccines. The present invention is drawn to the discovery of coupling technology which gives good reproducibility with respect to the carbohydrate to carrier ratio of conjugates. This invention also provides methods to verify the presence of immunogenic epitopes on oligosaccharide haptens and hapten-carrier conjugates.

Polysaccharide conjugates elicit non-boostable IgM antibody responses, typical of TI antigens. The antiserum produced in response to these polysaccharide conjugates does not have opsonic activity. In the present invention, oligosaccharides prepared by cleavage of polysaccharides from various bacterial strains are size separated and used to produce mono-hapten conjugates. These conjugates elicit IgG antibody isotypes with immunoprotective, opsonization ability. This antibody response is elicited without the use of any adjuvant. Thus, the methods of the inventions are ideally suited for producing immunogenic oligosaccharide hapten-carrier conjugates which utilize weakly or non-immunogenic polysaccharides of various strains. The presence of immunogenic epitopes on these oligosaccharides was found to be critical for eliciting an immunoprotective response.

The number of bacterial antigens needed to develop efficacious anti-pathogen vaccines is expanding. However, repeated administration of tetanus or diphtheria toxoid (often used as carrier proteins in vaccine compositions and as a prophylactic measure following trauma) may cause a phenomenon called carrier-induced epitope suppression. Epitope suppression has been described in the literature with synthetic peptide and saccharide-toxoid conjugates (Gaur et al., 1990; Peeters et al., 1991). Immune responses to a hapten coupled to a carrier protein can be reduced or absent when the recipient has been previously immunized with the carrier.

The goal of many researchers is to develop vaccines which elicit protection to the predominant bacterial serotypes which cause acute lower respiratory infection, otitis media and bacteria in infants, without inducing carrier suppression. The methods of the invention can be utilized to produce multi-hapten conjugates with optimal immunogenic epitopes to each bacterial serotype. These conjugates, which contain lower carrier protein amounts than traditional conjugates, reduce the occurrence of the carrier suppression phenomenon. The reduced antigen load possible using these conjugates minimizes the antigenic competition observed with traditional conjugates.

Previously, we reported that crystalline bacterial cell surface layers (S-layers) were useful as carriers for the development of prototype conjugate vaccines (Malcolm et al., 1993a) and as a means to avoid the carrier suppression phenomenon (Malcolm et al., 1993b). In our laboratory, we identified several S-layer glycoproteins which elicit non-cross reactive antibody and cellular responses. Vaccines to a variety of diseases can be developed using S-layers isolated from various bacterial strains, thereby avoiding carrier suppression observed with tetanus and diphtheria toxoids. However, S-layers are difficult to isolate and purify, as well as costly to produce, making them impractical for wide usage as vaccine carriers. The present invention describes methods to prepare mono, di and multi-hapten oligosaccharide conjugates which reduce the amount of carrier necessary to elicit specific responses, thereby decreasing the risk of carrier induced epitope suppression, even when tetanus or diphtheria toxoid is used as the carrier.

One specific application of the technology of the invention is for the development of effective vaccines for the prevention of pediatric pneumoniae infections. Another application of the invention is to develop vaccines for protection to strains of Group B Streptococcus, Group A Streptococcus, *Haemophilus influenzae* B, *Streptococcus pneumoniae* and *N. meningitidis* prevalent in infant disease, in the elderly or the immunosuppressed. Other applications include development of conjugates for eliciting protection to various bacterial or virus pathogens.

We have found that the use of conditions which cleave specific linkages (i.e., 1–4 linkages) but leave sugar monosaccharides and other immunologically important compounds such as phosphate intact results in improved immunogenicity of the resulting conjugates.

We have found that oligosaccharide size and conformation is important to maximize immunogenicity of conjugate preparation. Different oligosaccharide sizes are separated from hydrolyzed polysaccharide mixtures and isolated by size fraction. The monosaccharide content and the relative size of separated oligosaccharides is measured by, for example, HPLC analysis. Different size repeat units are tested using inhibition ELISA. We have found that ELISA inhibition is directly proportional to the immunogenicity of the oligosaccharide preparation and the resultant conjugate.

In particular, oligosaccharides prepared from cleavage of polysaccharides of *S. pneunococcus* strains 3, 6B, 8, 14, 19F and 23; pneumococcal C-substance; and *N. meningitidis* C-polysaccharide have been used in our laboratory. Preferred repeat units (R.U.) for oligosaccharides are as follows for some *S. pneumococcus* serotypes and pneumococcal C-substance:

Serotype
  3: 4–8 R.U.
  6B: 4–10 R.U.
  8: 2–8 R.U.
  14: 4–6 R.U.
  19F: 4–10 R.U.
  C-substance: 6–10 R.U.
  Preferred repeat units for *N. meningitidis* C-polysaccharide is 6–10 R.U.

Creating charged groups on saccharide haptens has been discovered to facilitate the coupling of the haptens to the carrier. Use of cation or anion exchange columns is effective in allowing coupling of oligosaccharide to carrier at a higher sugar to carrier ratio. This provides more hapten per carrier, and reduces the carrier suppression phenomenon. Reduced fractions of carbohydrate are used for coupling to carrier.

Another important aspect to produce effective conjugate vaccines is the use of purified carrier. Impurities found in a carrier preparation may interfere with coupling procedures. Aggregates of carrier proteins found in a carrier preparation can affect optimum hapten to carrier ratios necessary to elicit the desired response. Carriers are generally purified using size exclusion column chromatography, although any standard method which removes impurities and aggregate may be used.

The coupling reaction time and the amount of oligosaccharide, coupling reagent and carrier are critical for obtaining an ideal carbohydrate to carrier conjugate ratio. We have developed methods which quantify carbohydrate to carrier ratios by reproducible assays. Maintenance of pH and temperature conditions determined to be optimal during the coupling reaction is also important to produce an effective conjugate. Likewise, the use of effective blocking reagents which stop the coupling reaction but do not mask the immunogenic groups is important to create effective conjugate compositions.

Use of coupling chemistry which maintains immunogenic epitopes on oligosaccharides/polysaccharides is essential. We have found that EDC and periodate coupling, as described below may be used for coupling oligosaccharides to carriers. In addition to direct coupling of sugar to carrier, various linkers may be used to space the saccharide from the surface of the protein. Appropriate linkers may also provide charged or uncharged moieties as desired. The immunogenicity of coupled sugar-carrier compositions is determined by inhibition ELISA.

Using the methods of the present invention, we have discovered means to produce di-hapten and multi-hapten conjugates which still maintain their immunogenic epitopes. Conjugates with various oligosaccharide sequences and/or sizes can be produced. Similarly, conjugates comprising oligosaccharide and polysaccharide combinations may be synthesized. Such conjugates are able to reduce or eliminate antigenic competition.

Thus, appropriate conjugate design provides the ability to reduce carrier induced epitope suppression. Keys in this regard are the identification and use of immunogenic oligosaccharide epitopes and more effective coupling of sugar to protein. Binding a larger number of immunogenic epitopes per protein molecule means that less carrier is needed to provide protective immunization.

We have developed methods to quantify immunoprotective antibody response to conjugate compositions by isotyping ELISA, bactericidal and opsonization assays. This allows determination of which conjugates will elicit the appropriate immunoglobulin isotype response, i.e., IgG isotypes, when used to protectively immunize mammals.

Definitions

The following terms have the following meanings when referenced herein:

Oligosaccharide means a carbohydrate compound made up of a small number of monosaccharide units. In particular, oligosaccharides may be formed by cleaving polysaccharides.

Polysaccharide means a carbohydrate compound containing a large number of saccharide groups. Polysaccharides found on the outer surface of bacteria or viruses are particularly useful in the present invention.

Carrier means a substance which elicits a thymus dependent immune response which can be coupled to a hapten or antigen to form a conjugate. In particular, various protein, glycoprotein, carbohydrate or sub-unit carriers can be used, including but not limited to, tetanus toxoid/toxin, diphtheria toxoid/toxin, bacteria outer membrane proteins, crystalline bacterial cell surface layers, serum albumin, gamma globulin or keyhole limpet hemocyanin.

Immunogenic means causing an immune response. An immunogenic epitope means that portion of a molecule which is recognized by the immune system to cause an immunogenic response.

Hapten means an antigen, including an incomplete or partial antigen which may not be capable, alone, of causing the production of antibodies. Di- and multi-hapten, for purposes of this application, refer to compositions including two (di) or more (multi) oligosaccharide haptens conjugated to carrier.

Protectively immunogenic or immunoprotective means stimulating an immune response which prevents infection by pathogen.

Immunostimulatory means stimulating or enhancing an immune response to weakly immunogenic haptens or antigens.

Neonate means a newborn animal, including an infant.

Methodology

Preparation and Separation of Cleaved Polysaccharides

Polysaccharides, available through American Type Culture Collection, Rockville, Md. or by isolation procedures known in the art, were cleaved into oligosaccharide units using appropriate concentrations of chemicals. These chemicals include, but are not limited to trifluoroacetic acid, acetic acid, hydrofluoric acid, hydrochloric acid, sodium hydroxide and sodium acetate. Different time periods and temperatures may be used depending on the particular chemistry and concentration and on the resulting oligosaccharide desired. Commercially available enzymes (e.g., cellulase and β-galactosidase) or isolated bacteriophage-associated endoglycans known in the art can also be used to prepare oligosaccharides from polysaccharides.

FIG. 1 shows the repeat unit structures of the polysaccharides used in the Examples of the invention. Other bacterial and viral polysaccharides are known to those of skill in the art, and may be used in the methods and compositions of the present invention. Various polysaccharides can be cleaved including, but not limited to, pneumococcal group antigen (C-substance) and capsular polysaccharide of serotypes of *Streptococcus pneumoniae, Neissenia meningitidis, Haemophilus influenzae*, Group A Streptococcus and Group B Streptococcus.

After cleavage, the resulting oligosaccharide mixtures are separated by size using P-10 (fractionation range 1,500–20,000 molecular weight), P-30 (2,500–40,000 molecular weight) and P-60 (3,000–60,000 molecular weight) BioGel columns. The presence of carbohydrates in the various column fractions is determined using phenol-sulphuric or sialic acid assays and thin layer chromatography (TLC). Carbohydrate-containing column fractions are then analyzed by HPLC.

The presence of immunogenic epitopes on size-separated fractions of cleaved polysaccharides is determined by inhibition ELISA, as described below. If a preparation does not result in oligosaccharide fractions which inhibit in the ELISA test, cleavage procedures may be modified by changing enzymes or chemicals, molarity, reaction time or temperature in order to produce immunogenic epitopes.

Determination of Immunogenic Epitopes in Oligosaccharide Preparations

The presence of immunogenic epitopes in column fractions is confirmed by inhibition ELISA and phosphorous assay as set forth in the Examples section. Oligosaccharide fractions containing immunogenic epitopes (defined as those which produce at least about a 50% reduction in $O.D._{405}$ at 12.5 μg concentration) are selected for coupling to carrier.

Coupling to Carrier

The oligosaccharide or polysaccharide to be used for coupling to carrier is acidified or reduced in preparation for EDC or periodate oxidation coupling. For example, the oligosaccharide preparation may be acidified using a Rexyn™ 101 (H) organic acid cation exchange column to acidify the sugar for EDC coupling. Similarly, sugars may be reduced using standard methods for periodate oxidation coupling. When preparing di-hapten or multi-hapten conjugates, each oligosaccharide is activated individually for EDC or periodate conjugation.

Preferred di-hapten oligosaccharide conjugates include: 3:8-TT, 6:8-TT, 6:14-TT, 8:14-TT, 8:19-TT, 8:23-TT and 14:19-TT.

Carrier

Various protein, glycoprotein, carbohydrate or sub-unit carriers can be used, including but not limited to, tetanus toxoid/toxin, diphtheria toxoid/toxin, bacteria outer membrane proteins, crystalline bacterial cell surface layers, serum albumin, gamma globulin or keyhole limpet hemocyanin. In the specific examples of this invention, tetanus toxoid was used as the carrier. Tetanus toxoid preparations routinely contain aggregates and low molecular weight impurities. Purity of carrier is essential for obtaining consistency with coupling reactions, so size exclusion chromatography is used to obtain a purified carrier preparation.

Size separated, immunogenic epitope-containing oligosaccharides are coupled to purified carriers by carbodiimide (EDC) or periodate activation, using the procedures described in the Examples section. Any free hapten oligosaccharides are separated from hapten-carrier conjugates by column chromatography. The carbohydrate to protein ratio of conjugates is determined by, phenol sulfuric or sialic acid and Lowry protein assays. Typically, conjugates prepared by EDC coupling have a carbohydrate to carrier ratio of 1:2, while conjugates prepared using periodate oxidation coupling have carbohydrate to carrier ratios ranging from 1:5 to 1:10.

Determination of Immunogenic Epitopes on Conjugates

As stated previously, integrity of critical immunogenic epitopes is a problem with previously known conjugation technologies. In the present invention, the ELISA inhibition assay is used to determine the potential immunogenicity of various conjugates produced by our conjugation procedures. We have found that conjugates which demonstrate inhibition in this assay (at least about 50% reduction in $O.D._{405}$ at 6.25 μg concentration) using the methods set forth in the Examples, provide protective immunogenicity when used as a vaccine in mammals. Thus, this assay is used to screen for useful conjugate compositions.

Immunization to Elicit Immunoprotective Antibody Responses

Typically, mice are immunized on day 0 (1°-primary immunization) day 7 (2°-secondary immunization) and day 28 (3°-tertiary immunization) by subcutaneous injection (100 μl into 2 flank sites) with antigens (polysaccharide-conjugates, oligosaccharide-conjugates, uncoupled polysaccharide or oligosaccharide, or uncoupled tetanus toxoid) at doses of 0.1, 0.5, 1, 2.5 and 5 μg, based on carbohydrate content for EDC conjugates and protein content for periodate conjugates.

Antigens were diluted to various doses in 0.9% NaCl and mice injected with 0.9% NaCl were used as negative controls. Mice were bled 7–10 days post –2° and 3° immunization to collect serum to assay immunoprotective antibody responses. A typical immunization schedule is shown in Table 1 for S. Pneumoniae serotype 3 polysaccharide and oligosaccharide-tetanus toxoid conjugates prepared using EDC coupling.

Various other immunization schedules are effective, including: day 0 (1°), day 14 (2°) and day 44 (3°); and day 0 (1°), day 30 (2°) and day 60 (3°).

The conjugates of this invention may be used as classical vaccines, as immunogens which elicit specific antibody production or stimulate specific cell mediated immunity responses. They may also be utilized as therapeutic modalities, for example, to stimulate the immune system to recognize tumor-associated antigens; as immunomodulators, for example, to stimulate lymphokine/cytokine production by activating specific cell receptors; as prophylactic agents, for example, to block receptors on cell membrane preventing cell adhesion; as diagnostic agents, for example, to identify specific cells; and as development and/or research tools, for example, to stimulate cells for monoclonal antibody production.

Determination of Response

As previously discussed, antibody responses to TI and TD antigens differ. In the mouse, the response to a polysaccharide (TI) antigen is usually composed of a one-to-one ratio of IgM and IgG. In general, IgG isotypes are restricted, with $IgG_3$ being over-expressed in anti-polysaccharide serum. IgA isotypes may also be present. TI antigens elicit antibodies with low affinity and immunologic memory is not produced.

With TD antigens, increased secondary IgG antibody responses (an anamnestic response) are found, with a higher IgG to IgM ratio. Marked levels of IgA are usually not present. The TD antigen elicits a heterogeneous IgG isotype response, the predominant isotype being $IgG_1$, $IgG_{2a}$ and 2b isotypes can be expressed, while the $IgG_3$ isotype level is usually relatively low. TD antigens elicit immunologic memory and antibody affinity increases with immunizations. Thus, analysis of the immunoglobulin isotypes produced in response to conjugate administration enables one to determine whether or not a conjugate will be protectively immunogenic.

We have found that the conjugates of the present invention induce a response typical of TD, rather than TI antigens, as measured by direct and isotyping ELISA and opsonization assay.

Conjugates prepared using our EDC coupling methods elicited better antibody responses than conjugates prepared by periodate activation. Doses of 1 μg were most immunogenic. Oligosaccharide-conjugates prepared with diphtheria toxoid carriers elicited antibody responses similar to the responses elicited with the oligosaccharide-tetanus toxoid conjugate.

As described previously, several investigators have attempted to increase immunogenicity and elicit thymus-dependent antibody protection by coupling polysaccharide material to tetanus and diphtheria toxoids. Results indicate that these conjugates are only slightly more immunogenic than uncoupled capsular polysaccharide (CPS). One possible explanation for this may be that pertussis, diphtheria and tetanus toxoids (in aluminum salt adjuvant) are often administered as a prophylactic four dose immunization regime to infants. This regime may tolerize the infant, making the infant incapable of mounting a protective antibody response to a hapten/antigen coupled to these toxoid carriers (carrier suppression). Another possible reason for failure to induce protection may be structural. Protein carriers elicit and augment the immune response to haptens, but in the case of CPS-protein conjugates, the CPS portion is a relatively large TI antigen. The immune system may not recognize the CPS-protein as a conjugate, but simply as two distinct entities, resulting in a thymus-independent response to the CPS and a thymus-dependent response to the carrier.

This appears to be the case in our studies, as shown in Table 2. The immune system recognizes the polysaccharide of our polysaccharide-tetanus toxoid (TT) conjugate as a TI antigen. The potential TD inducing capability of the carrier with respect to antibodies to the polysaccharide is not observed. We postulate that the immunogenic epitopes of the carbohydrate haptens (oligosaccharides) must be in close proximity to the TD inducing epitopes of the carrier in order to convert a TI response to a TD response.

We have also used linker arm technology to prepare conjugates. We have used, for example, 6-amino-n-hexanoic acid as a linker. The resulting conjugates were found to be less effective in eliciting antibody responses than conjugates prepared by directly coupling EDC activated oligosaccharide haptens to carriers. This finding supports our hypothesis that close hapten to carrier proximity is needed to elicit TD responses.

We have also developed methods to determine the level of immunoprotective antibody elicited by the conjugates of the present invention using bactericidal or opsonization assays. These tests have shown that the conjugates of the present invention are effective in eliciting protective antibodies, as measured by these assays.

As discussed previously, the epitope-carrier suppression phenomenon has been observed by other researchers and in our laboratory with the S-layer carrier studies (Malcolm et al., 1993b). Our multi-hapten conjugates will reduce or circumvent this suppression, because these conjugates will contain greater mass of immunogenic epitope per molecule of carrier than conventional conjugate vaccines. With our conjugates, the immune system will not be "overchallenged" by the carrier. For example, a tri-hapten conjugate prepared by methods of this invention will require only three injections to elicit specific immune responses to three different target pathogens. In contrast, using conventional monohapten conjugates, one would need to administer nine injections to elicit similar responses. This means three times the amount of protein would be required.

Further, immunization regimes convert an anti-polysaccharide TI response to a TD response can be designed using the conjugates of the present invention. Economical initial exposure to polysaccharide (e.g., using Pneumovax 23) followed by a single administration of a conjugate of the present invention would induce IgG antibody levels (an anamnestic response). Such an immunization regime would not induce carrier suppression. In such cases, the immune system initially educated to various carbohydrate epitopes and antigens (a TI response) would be induced by multi-hapten conjugates to elicit stronger immunogenic responses to pathogens frequently causing disease in specific population groups (e.g., serotypes 1, 3, 4, 6, 9, 14, 18, 19 and 23 in infants).

Pharmaceutical Compositions

To elicit antibodies to specific pathogens and/or various carbohydrate moieties the conjugates of the invention may be administered by various delivery methods including intraperitoneally, intramuscularly, intradermally, subcutaneously, orally or nasally.

The formulation of the compositions of the present invention may include suitable pharmaceutical carriers. The conjugates of the invention are immunogenic without adjuvant, however adjuvants may increase immunoprotective antibody titers or cell mediated immunity response. Such adjuvants could include, but are not limited to, Freunds complete adjuvant, Freunds incomplete adjuvant, aluminium hydroxide, dimethyldioctadecylammonium bromide, Adjuvax (Alpha-Beta Technology), Inject Alum (Pierce), Monophosphoryl Lipid A (Ribi Immunochem Research), MPL+TDM (Ribi Immunochem Research), Titermax (CytRx), toxins, toxoids, glycoproteins, lipids, glycolipids, bacterial cell walls, subunits (bacterial or viral), carbohydrate moieties (mono-, di-, tri- tetra-, oligo- and polysaccharide) various liposome formulations or saponins. Combinations of various adjuvants may be used with the conjugate to prepare the immunogen formulation.

Exact formulation of the compositions will depend on the particular conjugate, the species to be immunized and the route of administration.

Such compositions are useful for immunizing any animal susceptible to bacterial or viral infection, such as bovine, ovine, caprine, equine, leporine, porcine, canine, feline and avian species. Both domestic and wild animals may be immunized. Humans may also be immunized with these conjugate compositions.

The route of administration may be any convenient route, and may vary depending on the bacteria or virus, the animal to be immunized, and other factors. Parenteral administration, such as subcutaneous, intramuscular, or intravenous administration, is preferred. Subcutaneous administration is most preferred. Oral administration may also be used, including oral dosage forms which are enteric coated.

The schedule of administration may vary depending on the bacteria or virus pathogen and the animal to be immunized. Animals may receive a single dose, or may receive a booster dose or doses. Annual boosters may be used for continued protection. In particular, three doses at days 0, 7 and 28 are preferred to initially elicit antibody response.

The following examples are not intended to limit the scope of the invention in any manner.

EXAMPLES

Example 1

Preparation and Separation of Polysaccharide Hydrolysates

FIG. 2 shows the separation profile of *Streptococcus pneumoniae* serotype 8 capsular polysaccharides through a BioGel P-10 column after acid hydrolysis (0.5M trifluoroacetic acid, 100° C., 20 minutes) resulting in discernible oligosaccharides of one to eight repeat units. Numbers one to eight correspond to the number of repeat units found in each peak, peak nine contains oligosaccharides of greater than eight repeat units. Oligosaccharides derived from hyaluronic acid were used to standardize the chromatographic system.

The relative size of the repeat units in peaks 1, 2, 3 and 4 were measured by HPLC analysis (FIG. 3). The HPLC retention times of glucose, M-3 maltotriose, M-7 maltoheptose, and M-10 malto-oligosaccharide (Sigma Chemical Co.) used as standards to determine relative size of various oligosaccharide repeat units is shown in FIG. 4. Monosaccharide content of the repeat structure was established by further hydrolysis of the oligosaccharide repeats with 2.0M trifluoroacetic acid (TFA) at 100° C. for 2 hours.

An example of the retention times of ribitol, rhamnose, galactose, fucose and mannose monosaccharide standards used to determine carbohydrate content of the hydrolysed repeat unit is shown in FIG. 5. The chemical structure of one serotype 8 repeat unit was determine to be β-glucose (1→4) β-glucose (1→4) α-galactose (1→4) αglucuronic acid (1→4) by GC-MS and NMR analysis. This corresponds to the repeating unit structure cited in the literature (Jones and Perry 1957).

FIGS. 6–10 are examples of separation profiles of S. pneumoniae serotypes 6B, 14, 19F and 23F polysaccharide hydrolysates (TFA, acetic acid or hydrofluoric acid) passed over P-10, P-30 or P-60 BioGel columns.

Figure 11:
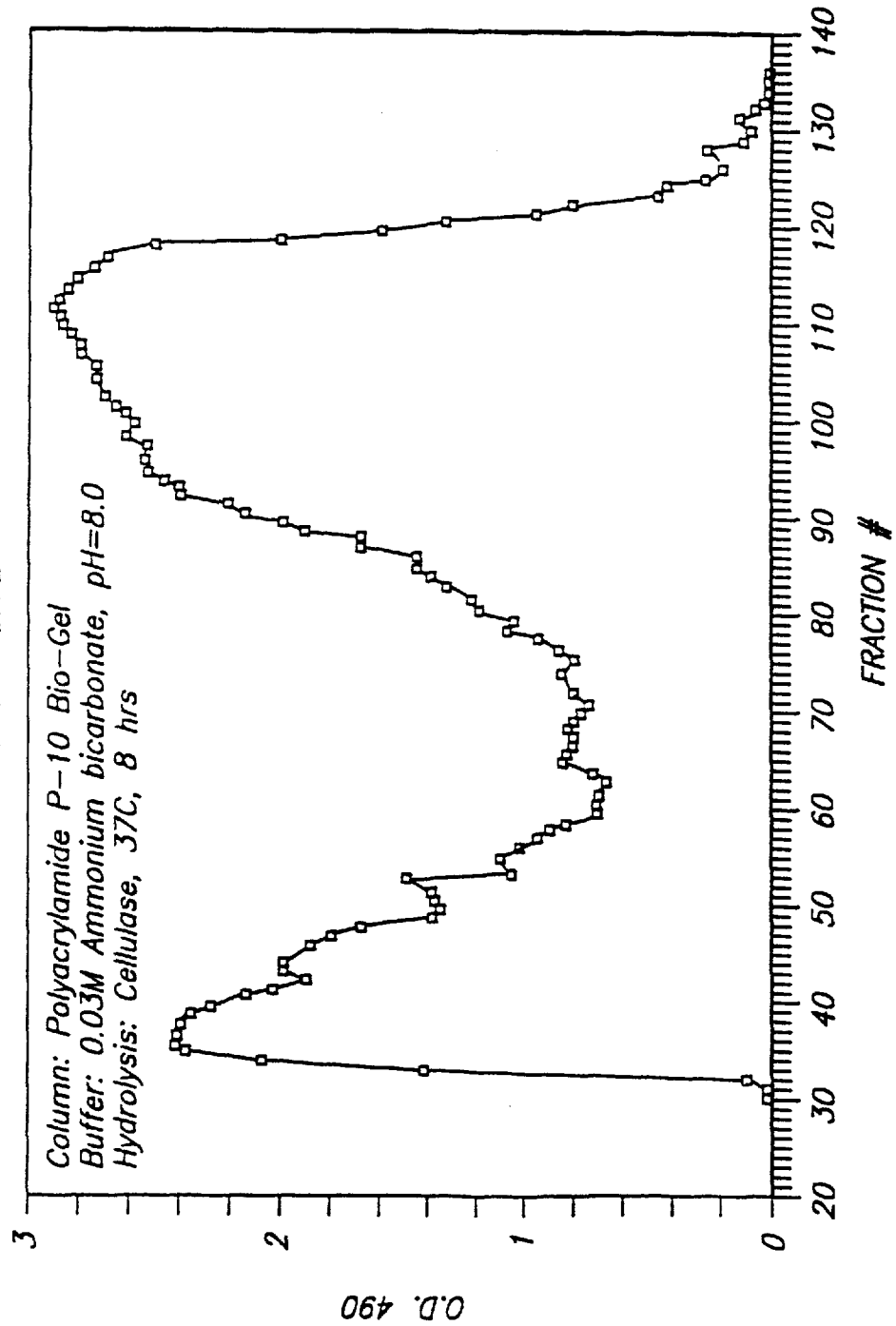
FIG. 11 shows the separation profile of *S. pneumoniae* serotype 8 polysaccharide cleaved by cellulase passed over a P-10 Bio Gel column.
Figure 12:
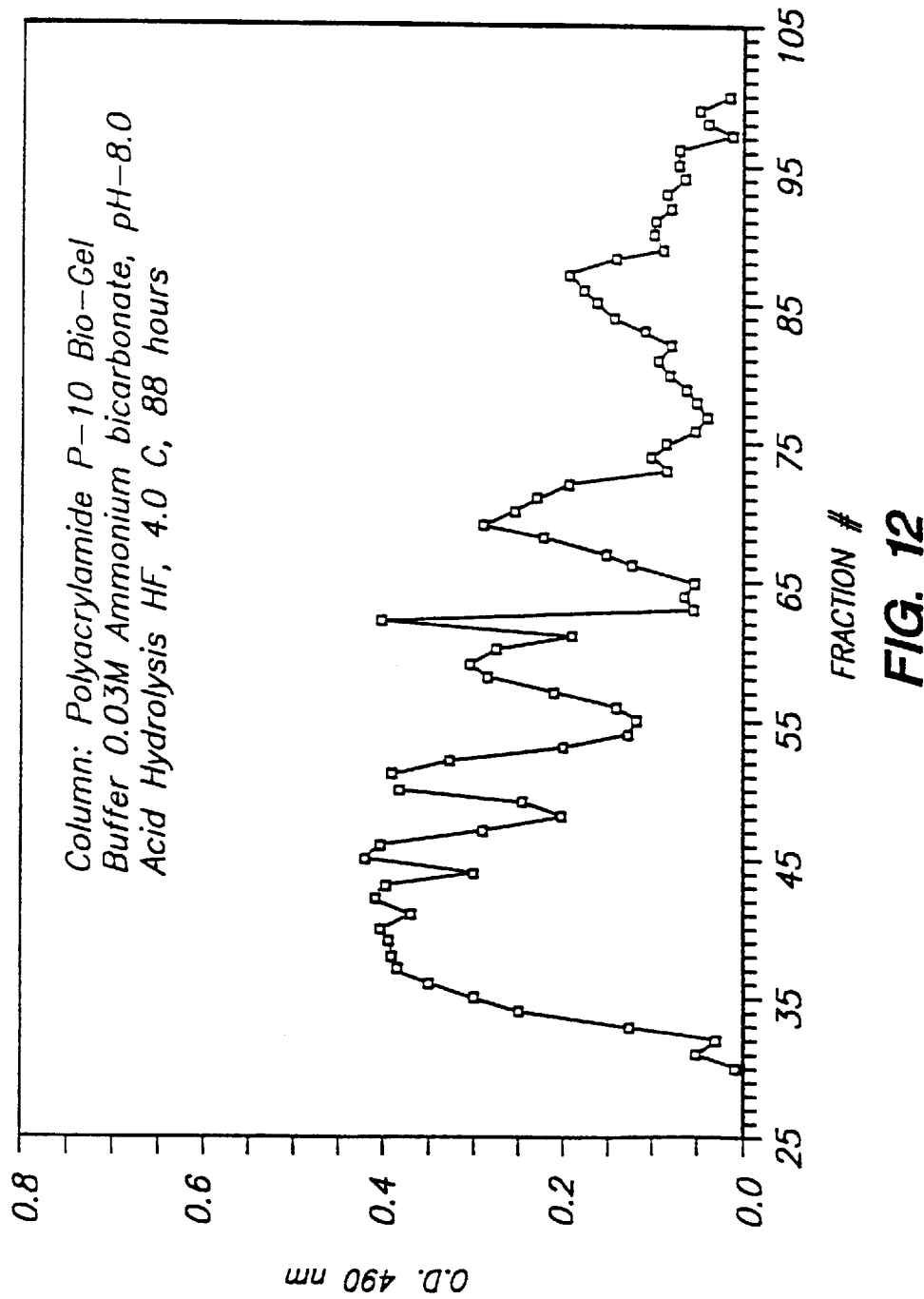
FIG. 12 shows the separation profile of pneumococcal C-substance polysaccharide hydrofluoric acid hydrolysates passed over a P-10 Bio Gel column.

FIG. 11 shows the separation of an enzyme cleaved polysaccharide (serotype 8 cleaved by cellulase). The separation of C-substance oligosaccharides is shown in FIG. 12.

Example 2
Inhibition ELISA to Determine Immunogenic Epitopes of Oligosaccharide Preparations The basic procedure utilized for inhibition ELISA to test for the presence of immunogenic epitopes on oligosaccharide preparations and oligosaccharide or polysaccharide-conjugates was as follows:

1. Coat 96 well EIA plates (NUNC) with 1 µg well of the antigen (Ag) using 0.05M $NaCO_3$ coating buffer (100 µl/well), incubate at 4° C. overnight.
2. On the same day, prepare inhibiting Ag tubes (e.g., various oligosaccharide hydrolysates) using 1×PBS–0.01% Tween 20 as diluent.

Make a 7 fold serial dilution in the tubes (starting from 25 µg/well to 0.391 µg/well in triplicate), the total volume in each tube should be 175 µl after serial dilution.

Prepare 1:1000 dilution of anti-serum of a specific type (e.g., Diagnostic anti-serum 14 that has been raised in rabbits, Statum Seruminstitut), in 1×PBS+Tween.

Add 175 µl of this solution to each tube. Total volume in each tube is now 350 µl. Incubate the tubes at 4° C. overnight.

3. Next day, block the EIA plates with 100 µl/well of blocking buffer (1×PBS+1% BSA), incubate at room temperature for 1 hour.
4. Flick off the plates and transfer content of each tube to the wells (100 µl/well,) incubate at room temperature for 2 hours.
5. Wash the plates 3 times with wash solution (0.01% Tween+1×PBS).
6. Prepare 1:1500 dilution of Goat-anti-rabbit (or anti-species of serotype specific serum used in Step 2) IgG Alkaline Phosphatase conjugate (TAGO) in 1×PBS+ 1% Tween buffer (100 µl/well). Incubate at room temperature for 2 hours.
7. Wash the plates 4 times with wash solution, flick off excess liquid.
8. Dissolve Alkaline Phosphatase substrate tablets (#104– Sigma) in the DEA (diethyleneamine) buffer pH=9.98, 5 ml/tablet, 100 µl/well.
9. Incubate the plates in the dark and read the Absorbance at 405 nm wavelength every 15 minutes.

Various commercial and laboratory prepared antiserum can be used in this assay, including, but not limited to, serum produced in mice, rat, rabbit, goat, pig, monkey, baboon and human.

Figure 13:
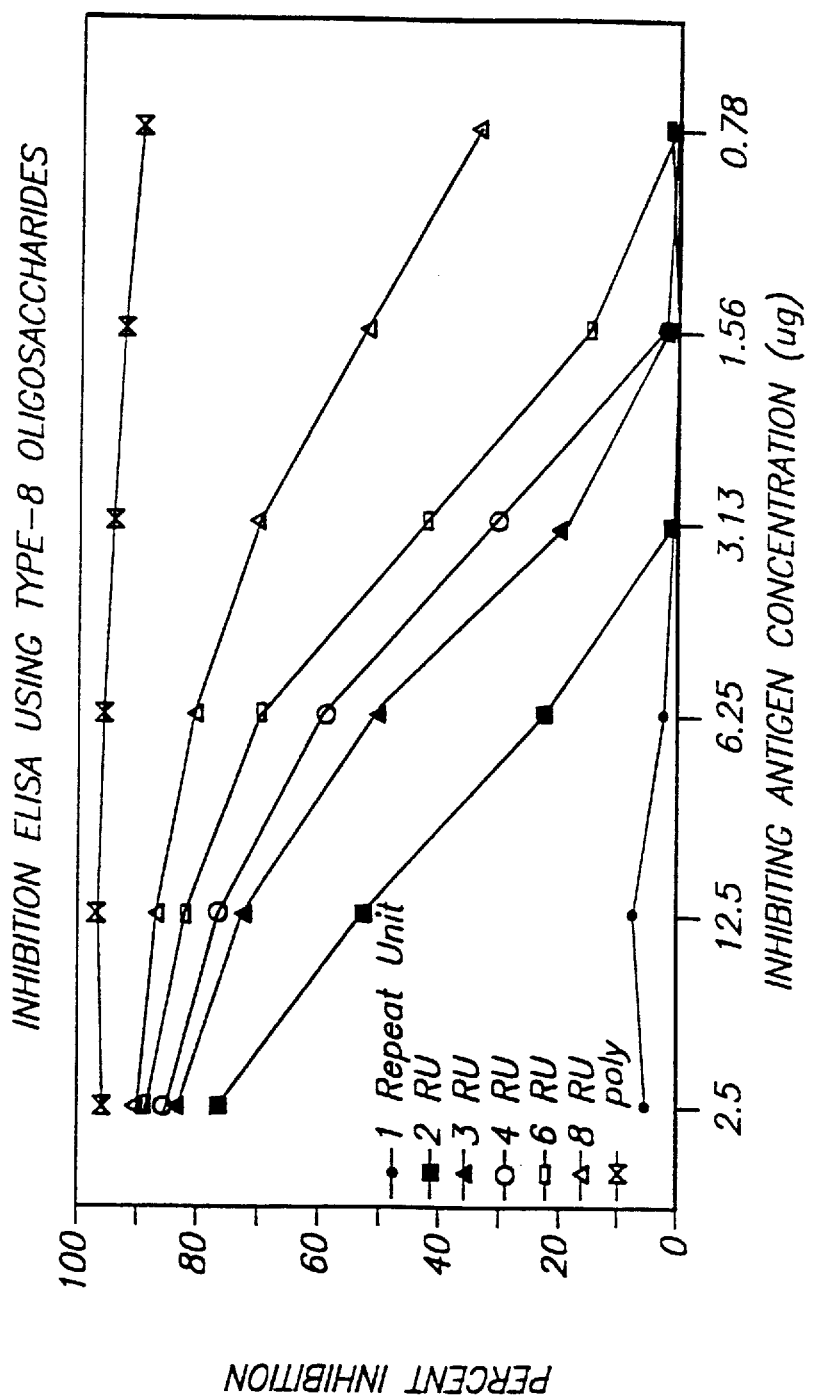
FIG. 13 shows the inhibition ELISA results using a mouse antiserum to *Streptococcus pneumoniae* serotype 8 oligosaccharide protein carrier conjugate.

FIG. 13 shows the inhibition ELISA results using a mouse antiserum to Streptococcus pneumoniae serotype 8 oligosaccharide protein carrier conjugate (2–4 repeat units coupled using EDC to tetanus toxoid). Inhibition was tested with type 8 oligosaccharides (0.5M TFA, 100° C., 20 minute preparation) of 1, 2, 3, 4, 6, & 8+ repeat units, and with type 8 polysaccharides. From these results, it can be seen that the 1 repeat unit (a 4 monosaccharide chain) does not contain an immunogenic epitope. The 2 repeat unit (8 monosaccharide chain) was capable of inhibiting antibody binding to the ELISA plate, indicating that it contains an immunogenic epitope. The molecular weight of repeat unit 2 was determined to be 1365 by FAB-MS analysis. This correlates well with the theoretical molecular weight of 8 saccharides. Repeat units of 3, 4, 6, 8+ and the whole polysaccharide also inhibited antibody binding to the ELISA plate, again indicating that immunogenic epitopes were present in these oligo/polysaccharides.

Table 3 demonstrates similar results found using a rabbit anti-S. pneumoniae serotype 8 specific serum (Statems Seruminstitut). Repeat unit 1 did not markedly inhibit binding; repeat units 2, 3, 4, 5, 6, 7, 8+ and whole polysaccharide inhibited binding.

Inhibition ELISA was also used to determine the presence of immunogenic epitopes on oligosaccharides prepared using different hydrolysis procedures on various polysaccharides. Table 4 shows results with methods used by the prior art, for example, Porro Canadian Patent No. 2 052 323 to hydrolyse S. pneumoniae serotype 6 polysaccharide (0.01M acetic acid, 100° C., 30 hours). Whole polysaccharide blocked binding at low antigen concentration (effective at 0.39 µg concentration) while the acetic acid hydrolysate did not. Note that we could not size separate the hydrolyzed preparation because it was "caramelized."

We discovered that different hydrolysing agents (e.g., TFA) and reduced time and temperature produced oligosaccharides with more immunogenic epitopes, as shown in Table 5. A 0.5M TFA, 70° C. 1 or 2 hour hydrolysate effectively inhibited antibody binding at a 3.13 µg concentration, a 4 hour preparation did not. Tables 6 and 7 also illustrate the effect of time for preparing 6B oligosaccharides with or without immunogenic epitopes. A 2 hour acetic acid preparation blocked antibody binding (at 3.13 µg concentration), the 24 and 48 hour preparations did not. Similarly, a 1.5 hour TFA preparation more effectively blocked binding than a 3 hour preparation.

As shown in Table 8, 0.5M TFA hydrolysis of S. pneumoniae serotype 14 at 70° C. for 7 hours, as disclosed in the prior art (Porro, Canadian Patent 2 052 323), is not preferred. Reduced molar concentrations of TFA (e.g., 0.1M) is better for preparing immunogenic 14 oligosaccharides.

Table 9 illustrates the importance of selecting oligosaccharides which contain immunogenic epitopes for coupling to carrier. The 3 repeat unit structure of serotype 14 oligosaccharide could not inhibit antibody binding, the 4 and 8 repeats, however, contain the immunogenic epitopes and effectively blocked antibody binding.

Table 10 shows the effect of hydrolysate concentration and reaction time for preparing 14 oligosaccharides containing immunogenic epitopes. Immunogenic epitopes were conserved by a TFA 7 hour hydrolysis, but destroyed when hydrolysed for 24 hours.

Table 11 illustrates the importance of using optimal heat conditions for producing 19F oligosaccharides containing immunogenic epitopes. Immunogenic epitopes were destroyed by HCl hydrolysis at room temperature, but maintained when hydrolysis was performed at 70° C.

As shown in Table 12, poor inhibition of antibody binding was observed with 0.25M TFA, 70° C., 3 hr hydrolysates of 23F polysaccharides, (Porro, Canadian Patent 2 052 323). Table 13 demonstrates the effect of time on the generation of immunogenic 23- oligosaccharides. Oligosaccharides produced by 0.1M TFA hydrolysis, 70° C. for 3 hours inhibited antibody binding, oligosaccharides prepared by hydrolysis for 5 hours did not inhibit. Table 14 demonstrates the presence of immunogenic oligosaccharides after 0.5M TFA hydrolysis at 70° C. for 15 minutes or with 5M acetic acid at 70° C. for 5 hours. These hydrolysates effectively inhibited to 0.78 μg concentration.

Table 15 demonstrates the utility of the inhibition ELISA to recognize immunogenic oligosaccharides of *Neisseria meningitidis* serotype C. Hydrolysates prepared with NaOAc, blocked antibody binding as effectively as the whole polysaccharide.

Example 3

Acidification of Carbohydrate Moieties for Carbodiimide Coupling

A Rexyn 101 (H) organic acid cation exchange column (Fisher Scientific) was prepared and washed with d $H_2O$. Polysaccharide or oligosaccharide samples dissolved in d $H_2O$ (pH neutral) were run over this column and collected at a rate of one drop per six seconds. Acidification was confirmed by pH colour-fixed indicator sticks. Excess $dH_2O$ was used to wash the column. Acidified fractions were pooled and lyophilized for use in coupling reactions.

FIG. 14 depicts a TFA cleavage between β-D-Glcp (1→4) β-D-Gal of an oligosaccharide structure resulting in the formation of an aldehyde and hydroxyl group. Further oxidation of the aldehyde results in a carboxyl group. When this material is passed through a cation exchange column, a $COO^-$ group results.

Example 4

Coupling Procedures and Quantification Assays

Carbodiimide (EDC) Coupling Procedure

A 1:1 weight ratio of ion charged carbohydrate (polysaccharide or oligosaccharide) sample (e.g., 3 mg) and EDC (3 mg) was dissolved in 2 mls of 0.1M $KH_2PO_4$, a pH of 4.5 was maintained with 1N NaOH or HCl. This mixture was stirred for 1 hour at room temperature. Carrier (3 mg) was added to the EDC activated carbohydrates and then stirred for 4 hours at room temperature. This reaction was stopped by the addition of 200 μl of 10% ammonium bicarbonate, the mixture was then further stirred for 1 hour at room temperature.

The resultant conjugate was dialysed against d $H_2O$ overnight using 50,000 molecular weight cut off (MWCO) dialysis tubing.

Conjugates were lyophilized and then assayed by Lowry protein, phenolsulfuric acid, sialic acid and phosphorous assays for composition (methods described below). Typically, conjugates prepared with this coupling methods have a carbohydrate to carrier ratio of 1:2.

Phenol-Sulfuric Acid Assay for Quantification of Carbohydrates

Reagent: 5% phenol solution (5.5 mL liquid phenol (90%) added to 94.5 mL distilled water).

Standard: Glucose 1 mg/ml stock solution. Prepare 2 to 60 μg/200 μl sample buffer for standard curve.

Procedure: (Adapted from: Handbook of Micromethods for the Biological Sciences. Keleti, G. & W. H. Lederer (eds). 1974. Van Nostrand Reinhold Co., New York.)

1. Place 200 μl samples into very clean tubes.
2. Add 200 μl phenol reagent.
3. Rapidly add 1 mL concentrated sulfuric acid.
4. Vortex well.
5. Let stand at room temperature for 30 minutes.
6. Color is stable at room temperature for 2 to 30 hours.
7. Read absorbance at 490 nm: blank with tube containing buffer only as sample in #1.

Quantitative Estimation of Sialic Acid Reagents a. 6 gram of $Al_2(SO_4)_3$. 18 $H_2O$ dissolved up to 20 ml with distilled water.

b. 1 gram para-dimethylaminobenzaldehyde dissolved up to 20 ml with 6N HCl. (Store in a dark bottle in the refrigerator).

Standard: N-acetylneuraminic acid at 0, 2.5, 5, 10, 15, 20, 25, 30, 35, 40, 45 and 50 μg/μl total volume is 350 μl. Use distilled water to make up to 350 μl.

Method 1. 200 μl of sample in duplicates. Make up to 350 μl with distilled water.
2. Add 700 μl of reagent A to each tube. Shake.
3. Add 350 μl of Ehrlich reagent B.
4. Cover all tubes with marbles.
5. Heat the tubes at 100° C. for 30 minutes using Pierce Heating modules.
6. Cool the tubes rapidly to room temperature in an ice bath.
7. Read optical density at 530 nm wavelength.

Phosphorous Assay

Reagents: a. 2.5% ammonium molybdate; b. 10% ascorbic acid; c. 70% perchloric acid; and d. 1 mM sodium phosphate standard.

Procedure: (Adapted from: Rouser, G., Siakotos, A. N. and Fleischer, S. 1966. Lipids 1:85–86)

1. Place samples and standards (0, 25, 50, 100 and 200 μl; 25 to 200 nmoles) into clean tubes.
2. Dry samples in a heater block at 180° C. for 5 minutes in the fume hood.
3. Add 450 μl perchloric acid to each tube, cover each tube with a marble and heat at 180° c. for 30–60 minutes.
4. Add 2.5 mL d $H_2O$. after tubes have cooled.
5. Add 0.5 ml ammonium molybdate and vortex immediately.
6. Add 0.5 ml ascorbic acid and vortex immediately.
7. Place tubes in 95° c. water for 15 minutes.
8. Read absorbance at 820 nm after tubes have cooled.
9. Samples can be left for several hours before being read.

Lowry Protein Assay Reagents a. 2% (w/v) $Na_2CO_3$ in 0.1M NaOH (1 L)

b. 0.5% $CuSO_4$ in 1% sodium citrate (100 mL)

c. Folin-Ciocalteu phenol reagent (2×)

d. Bovine serum albumin (1 mg/mL)

Procedure

1. Prepare standard curve which consists of: 0, 12.5, 25, 50, 100 and 200 μg of BSA in a final volume of 200 μL.
2. Bring unknown protein samples to 200 μL with d $H_2O$.
3. Mix reagents A and B 50:1 (v/v) and add 2 mL to each sample.

4. Vortex and let stand at room temperature for 10 minutes.
5. Dilute Folin-Ciocalteu phenol reagent 1:1 with d $H_2O$ and add 200 μL to each sample.
6. Vortex and let stand at room temperature for 30 minutes.
7. Read absorbance at 660 nm.

Periodate Oxidation Coupling Procedure

Samples of polysaccharide or oligosaccharide (e.g., 3 mg) were dissolved in 3 ml of freshly prepared 60 mM sodium meta-periodate in 50 mM sodium acetate. This preparation was then stirred overnight at 4° C. Ethylene glycol (300 μl) was then added to stop the reaction, this mixture was subsequently stirred at room temperature for 1 hour and then lyophilized. Samples dissolved in 1.5 ml of 0.03M ammonium bicarbonate (pH=8.0) were run over a P-2 Bio-Gel column. The phenol-sulfuric acid assay was used to determine fractions containing the periodate oxidized form of the samples, which were subsequently lyophilized.

Figure 15:
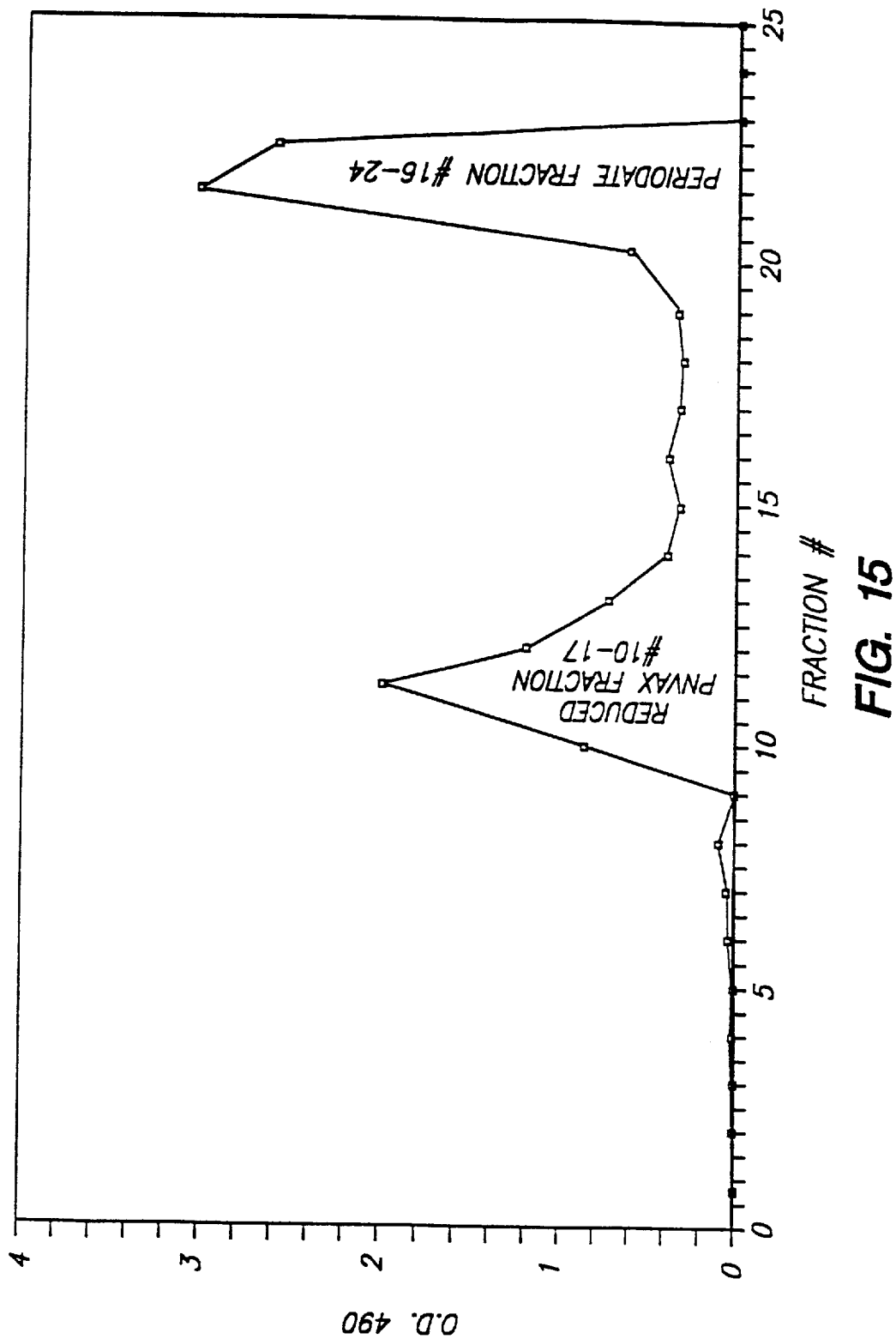
FIG. 15 shows the separation of reduced and periodate fractions of a polysaccharide (23 valent polysaccharide vaccine-Pneumovax® 23, Merck, Sharp and Dohme).

FIG. 15 shows the separation of a reduced polysaccharide (23 valent polysaccharide vaccine-Pneumovax® 23, Merck, Sharp and Dohme) fraction. FIGS. 16 and 17 demonstrate separation of reduced oligosaccharides of serotypes 6B and 19F of *Streptococcus pneumoniae*, respectively.

Three mg of reduced saccharide and 3 mg of carrier were dissolved in 3 mls of 0.1M sodium tetraborate decahydrate, pH 8.9. Sodium cyanoborohydride (H+ source) was then added to this mixture and stirred for 48 hours at 50° C. This reaction was stopped by adjusting the pH to 3–4 with 80% acetic acid. This conjugate was then dialysed for 48 hours against d $H_2O$ (2–3 d $H_2O$ changes) using 50,000 MWCO dialysis tubing.

The conjugate was lyophilized, and the composition of the conjugate determined by Lowry protein assay, phenol-sulfuric, sialic acid and phosphorous assays. Typically, conjugate prepared using this coupling method have carbohydrate to carrier ratios of 1:5 to 1:10.

FIG. 18 depicts the periodate and EDC coupling chemistry reactions.

Example 5
Conjugate Carriers

Example 4 describes methods used to produce immunogenic oligosaccharide/polysaccharide conjugates from weakly or non-immunogenic polysaccharides.

Tetanus toxoid was purified for use as a carrier by column chromatography. This purified toxoid elicited high levels of IgM (e.g., 50 μg/ml mouse serum) and IgG isotypes (e.g., $IgG_1$ 100 μg/ml of serum; $IgG_{2a}$, 38 μg/ml of serum; $IgG_{2b}$, 68 μg/ml of serum; and $IgG_3$, 105 μg/ml of serum).

Figure 19:
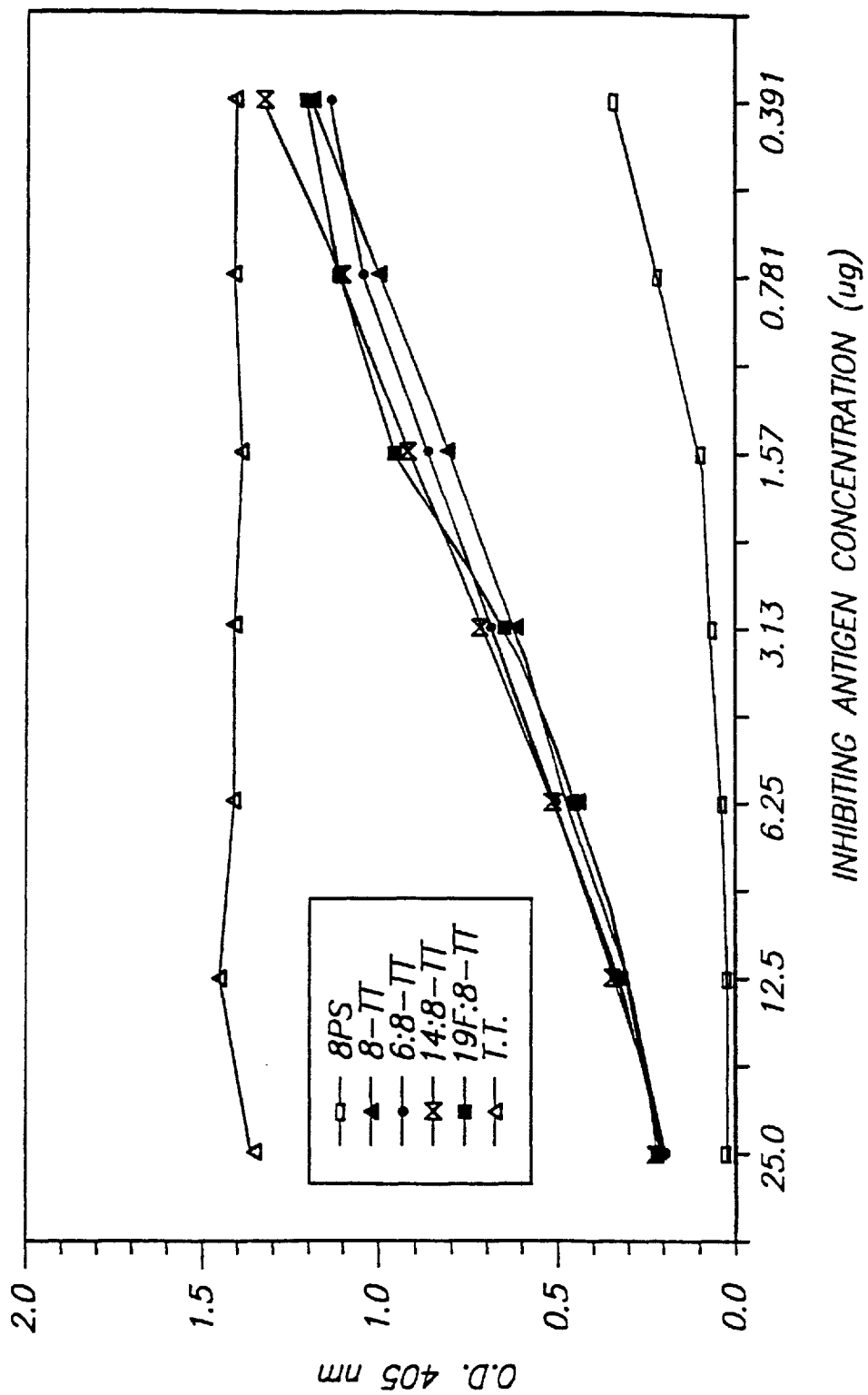
FIG. 19 shows how a mono-hapten 8-oligosaccharide tetanus toxoid, TT conjugate inhibited anti-8 serum binding to a 8 polysaccharide coated ELISA plate.

Example 6
Determination of Immunogenic Epitopes on Oligosaccharide/Polysaccharide Conjugates The inhibition ELISA as described in Example 2 was used. The presence of immunogenic epitopes on a mono-hapten 8-oligosaccharide tetanus toxoid conjugate was confirmed by inhibition ELISA. This conjugate inhibited anti-8 serum binding to a 8 polysaccharide coated ELISA plate (FIG. 19). Free tetanus toxoid did not inhibit binding. The presence of immunogenic 8 oligosaccharide on di-hapten 6:8; 14:8 and 19:8 conjugates was also shown. This figure illustrates the reproducibility of our coupling procedures, as the 8-mono-hapten and di-hapten conjugates equally blocked antibody binding, indicating that each conjugate contained equivalent amounts of 8 oligosaccharide.

Table 16 shows results of inhibition ELISA when 6B polysaccharide, 6B oligosaccharides, a 6B:8 di-hapten- oligosaccharide tetanus toxoid conjugate or tetanus toxoid alone was used as inhibiting antigens. Tetanus toxoid did not inhibit binding of anti-6B serum to a 6B-polysaccharide coated ELISA plate. Free 6B-oligosaccharide or polysaccharide did inhibit binding. The 6B:8 di-hapten-oligosaccharide-TT conjugate also inhibited binding. This confirms the presence of immunogenic 6B epitopes on the 6B:8 di-hapten-TT conjugate.

Similarly, a 14:8-di-hapten-TT conjugate inhibited anti-14 serum binding, demonstrating the presence of serotype 14 immunogenic epitopes (Table 17). Note that at high concentrations, there was non-specific inhibition by TT alone. We have found that this is an artifact of anti-14 in this assay.

Various oligosaccharide fractions of a 23F hydrolysate were coupled to TT. All contained immunogenic epitopes of the 23F serotype as shown in Table 18.

The immunogenic epitopes of *N. meningitidis* oligosaccharides (NaOAc preparation) were similarly maintained when coupled to tetanus toxoid (see Table 19).

Example 7
Determining Antibody Isotype Levels Elicited by Thymus Independent (TI) and Thymus Dependent (TD) Antigens The basic procedure to measure antibody isotype levels is as follows to quantify IgM, IgG and IgA isotypes elicited by various conjugates:

1. Coat EIA plates (NUNC, IMMUNOSORB) with 1 μg/well of Ag in 0.05M sodium carbonate/sodium bicarbonate buffer pH-9.5, 100 μl/well.
2. Incubate at 4° C. overnight.
3. Next day, block plates with 100 μl/well of blocking buffer (1×PBS+1% BSA). Incubate at room temperature for approximately 1 hour.
4. Prepare 1:25 dilution mouse serum in working-buffer (1×PBS+0.1% Tween). Add 100 μl/well into the appropriate well, incubate at room temperature for 2 hours.
5. Wash plates 3× with washing buffer (1×PBS+0.05% Tween). Flick off excess liquid by tapping the plates on the bench top.
6. Prepare 1:2 dilution of EIA Grade Mouse Type (Rabbit Anti-Mouse, IgM, $IgG_1$, $IgG_{2a}$, $IgG_{2b}$, $IgG_3$ and IgA, Bio-Rad) in working buffer at 100 μl/well. Incubate at room temperature for 2 hours.
7. Wash plates 3× with washing buffer.
8. Prepare 1:1500 dilution of Goat-anti-Rabbit IgA Alkaline Phosphatase conjugate (TAGO) in working buffer at 100 μl/well. Incubate at room temperature for 2 hours.
9. Wash plates 4× with washing buffer.
10. Prepare enzyme substrate using Sigma #104 Alkaline Phosphatase Substrate tablets (one tablet/5 mls of 10% diethanolamine substrate buffer), 100 μl/well. Incubate at room temperature in the dark and read every 30 minutes at 405 nm wavelength.
11. Convert absorbance readings to μg antibody/ml serum using dose-response curves generated from ELISA responses, of the rabbit anti-mouse isotype antibodies to various concentrations of mouse class and subclass specific immunoglobulin (Zymed Labs. Inc.).

Table 2 shows the antibody elicited in mice when immunized with *S. Pneumoniae* serotype 8 oligosaccharide and polysaccharide conjugates. Only the 8 oligosaccharide-conjugate elicited IgG antibodies of all isotypes, the unconjugated oligosaccharide was not immunogenic, the polysaccharide and the polysaccharide conjugate elicited antibody isotypes typical of TI responses (mainly IgM, IgA, and $IgG_3$ isotypes).

Adjuvant was not necessary to elicit the IgG isotypes with our oligosaccharide-tetanus toxoid conjugate. Conjugates comprising relatively small oligosaccharides, haptens of 2–4 repeat units (8–16 saccharides), elicited the best antibody responses as measured by direct ELISA.

Direct ELISA Protocol

1. Use NUNC Maxisorp Immunoplate.
2. Dilute coating antigen to 1.0 µg/100 µl in carbonate-bicarbonate buffer. Use glass tubes as antigen will stick to plastic.
3. Add 100 µl to each well of plate. Store overnight at 4° C.
4. Wash 3× in PBS–0.05% Tween. Shake out excess PBS by tapping on Kimwipes/paper towels.
5. Add 100 µl/well of blocking agent (1×PBS–1% BSA). Incubate for 60 minutes at room temperature.
6. Wash 3× as in Step 4.
7. Add 100 µl/well of test antibody appropriately diluted in PBS–0.01% Tween. Incubate for 90 minutes at room temperature.
8. Wash 3× as in Step 4.
9. Dilute alkaline phosphatase conjugated anti-mouse Ig (TAGO Cat #4653) in PBS-Tween 1/1500. Add 100 µl/well and incubate for 90 minutes in the dark.
10. Wash 3× as in Step 4.
11. Add 100 µl/well Sigma 104 Phosphatase Substrate (disodium-p-nitrophenyl phosphate tables). Add 2 tablets (5 mg/tablet) of substrate to 10 mL diethanolamine buffer. Keep in dark as substrate is inactivated by light.
12. Incubate in dark at room temperature. The development of the reaction varies depending on the antibody. Absorbance can be read on the Microelisa Auto Reader (405 nm) at approximate 30 minutes intervals.

Results in Table 20, show a comparison of $IgG_1$ and $IgG_3$ levels in mice immunized with 8-conjugate at 3 weeks of age or at 8 weeks of age. Significant $IgG_1$ levels were elicited by the 8-oligosaccharide-TT-conjugate in mice immunized at 3 weeks old (0.273 µg/ml) and at 8 weeks old (0.700 µg/ml). Indicative of a TD response, an adjuvant (e.g., FCA) increased specific $IgG_1$ (1.22 µg/ml). The 8-polysaccharide induced over-expression of $IgG_3$ and low $IgG_1$, typical of a polysaccharide TI response. The 8-polysaccharide-TT conjugate, considered a "TD antigen", induced only low levels of $IgG_1$, with overexpression of $IgG_3$, characteristic of TI polysaccharide antigens. Also, adjuvant in combination with the 8-polysaccharide-TT conjugate did not enhance $IgG_1$ levels, but did increase $IgG_3$ antibody (TI-like response). Some polysaccharide-conjugates are known to elicit combinations of TI and TD antibody response profiles (Stein, 1992; Stein, 1994).

Figure 20:
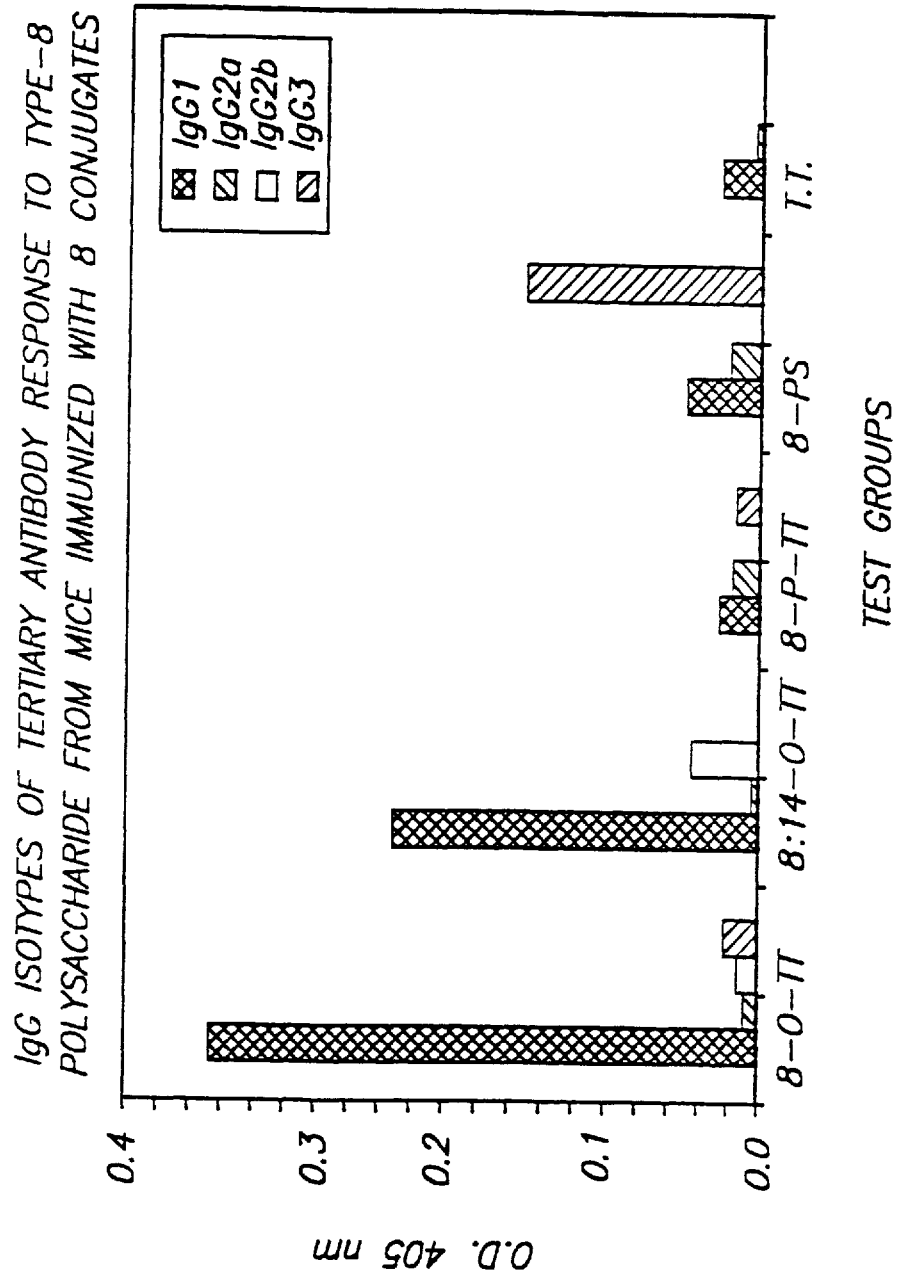
FIG. 20 depicts the IgG antibody isotypes elicited by *S. pneumoniae* serotype 8 polysaccharide following immunization with an 8:14 di-hapten-oligosaccharide-TT conjugate.

FIG. 20 depicts the IgG antibody isotypes elicited by a 8:14 di-hapten-oligosaccharide-TT conjugate to 8 polysaccharide. Like the 8-mono-hapten conjugate, this di-hapten conjugate could induce much higher levels of specific IgG, antibody (a TD response) than a 8-polysaccharide-conjugate or 8-polysaccharide alone. Overexpression of the $IgG_3$ isotype to polysaccharide immunogen is shown. Control mice were injected with tetanus toxoid alone.

Results obtained with serotype 14-oligosaccharide conjugates are shown in Table 21. A 14-oligosaccharide-TT-conjugate prepared by 0.1M TFA hydrolysis elicited $IgG_1$, $G_{2a}$, $G_{2b}$, and G3 isotypes, the 1 µg dose was the most immunogenic. Oligosaccharide-TT conjugates prepared using carbohydrate fractions of separation peaks 7 and 8 of a 0.5M TFA hydrolysate elicited lower levels of IgG isotypes. Smaller oligosaccharides (peaks 4 and 5 of the 0.5M TFA preparation) in conjugate form elicited low levels of IgG isotypes. The 14-polysaccharide-TT conjugate elicited relatively high levels of $IgG_1$ isotypes. However, serum from mice injected with this polysaccharide conjugate was not immunoprotective (as will be shown in Example 8, Table 24). There appears to be a required threshold level of IgG antibody isotypes to provide immunoprotection to the serotype 14 pathogen. The uncoupled 14 polysaccharide, tetanus toxoid alone, or 0.9% NaCl negative control serum all displayed low levels of all isotypes, equivalent to normal mouse serum (NMS) levels.

Figure 21:
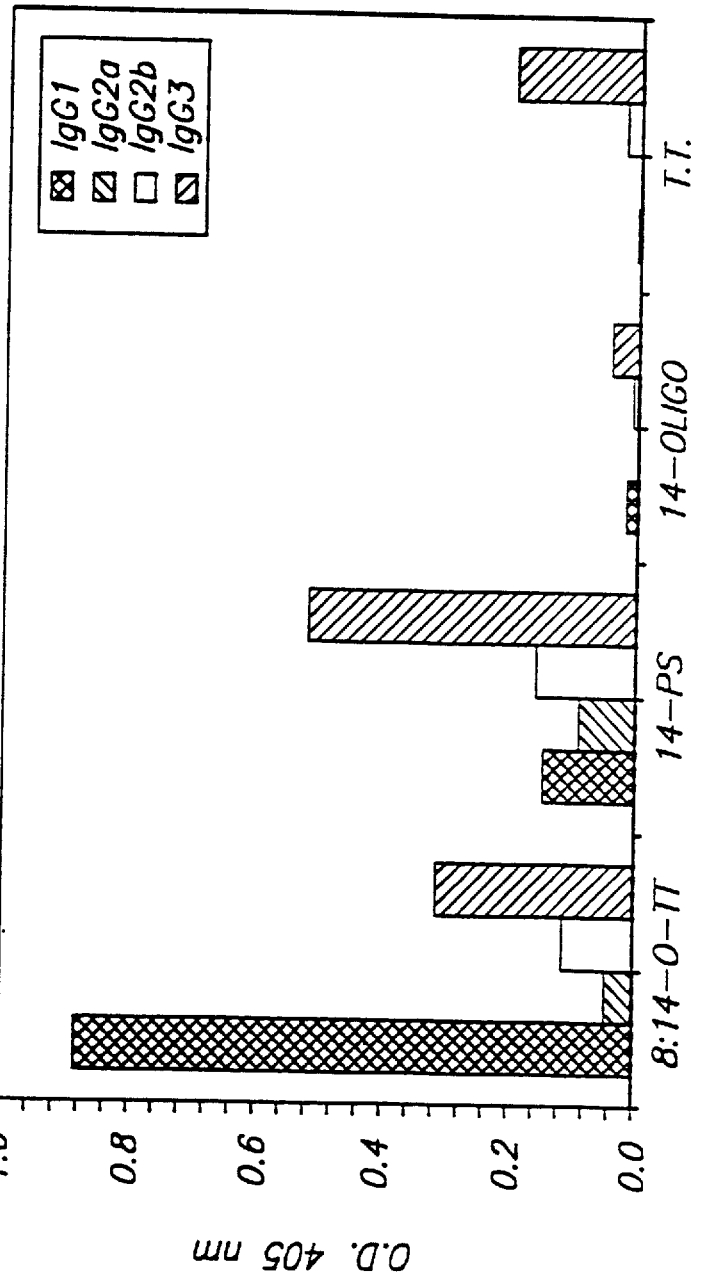
FIG. 21 shows an increased level of $IgG_1$ antibody isotype elicited by polysaccharide following immunization with an 8:14 di-hapten-oligosaccharide-conjugate, typical of a TD response.

FIG. 21 shows an increased level of IgG, antibody isotype to 14-polysaccharide elicited by a 8:14 di-hapten-oligosaccharide-conjugate, typical of a TD response. The 14-polysaccharide induced overexpression of $IgG_3$ (TI response), the 14 oligosaccharide alone was not immunogenic. Uncoupled tetanus toxoid was a negative control.

Figure 22A:
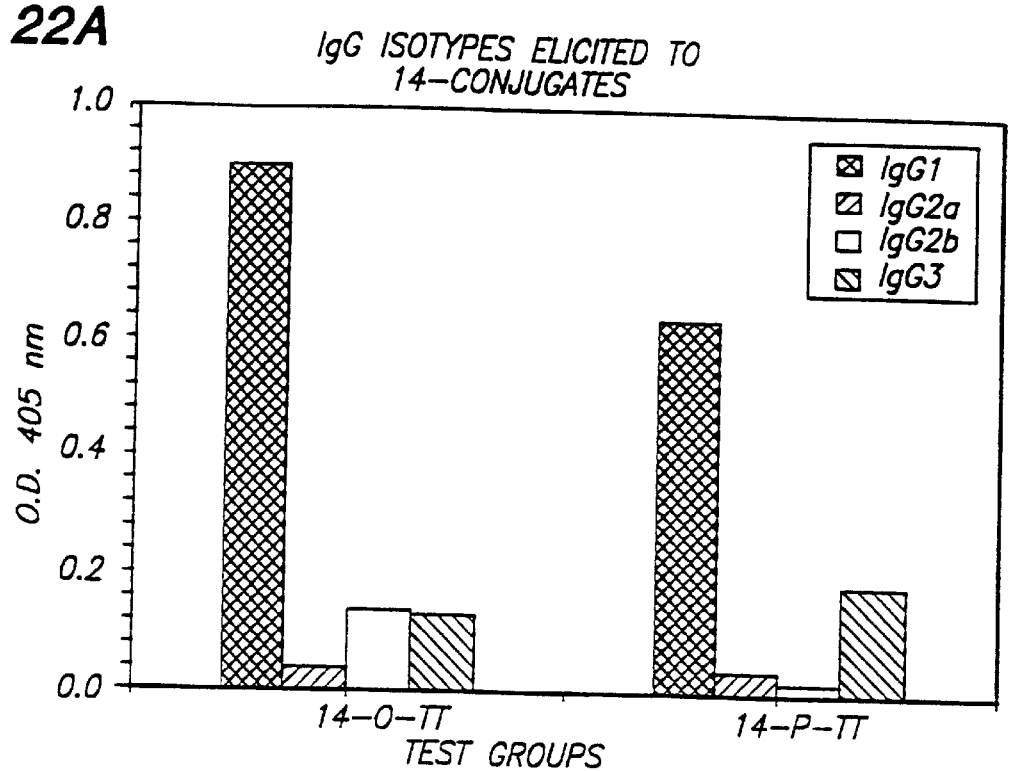
FIGS. 22A and 22B show IgG isotypes elicited from groups of mice immunized with 14-polysaccharide and oligosaccharide conjugates with and without adjuvant.
Figure 22B:
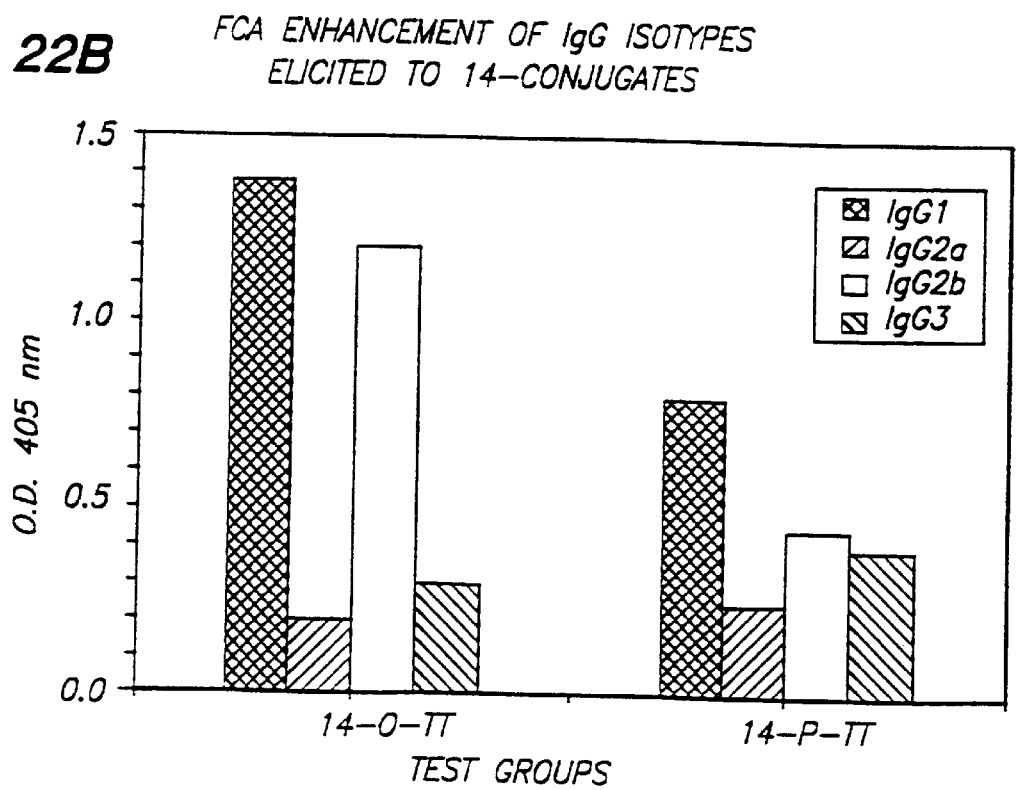

As with individual humans, different groups of mice displayed variable responsiveness to oligosaccharide- and polysaccharide-conjugates. In certain groups of mice, variations in the different IgG antibody isotype levels were observed. FIG. 22A shows results from a group of "good responser" mice which produced $IgG_1$ to a 14-polysaccharide conjugate (a TD-like response). Nevertheless, a 14-oligosaccharide-conjugate elicited higher $IgG_1$ levels. This conjugate also elicited substantial levels of $IgG_{2b}$ (0.955 µg/ml=oligosaccharide-conjugate; 0.139 µg/ml=polysaccharide-conjugate). This response was TD driven as FCA enhanced these $IgG_{2b}$ antibodies, FIG. 22B. (1.509 µg/ml=oligosaccharide-conjugate; 0.474 µg/ml= polysaccharide-conjugate).

The ability of oligosaccharide-conjugates of the invention, to elicit greater TD antibody responses than polysaccharide-conjugates was not limited to *S. pneumoniae* immunogens. Oligosaccharide-conjugates of *Neisseria meningitidis* Group C elicited greater levels of $IgG_1$ isotype antibody (7.01 µg/ml) than the polysaccharide-conjugate (3.60 µg/ml) or polysaccharide alone (0.162 µg/ml). Interestingly, the $IgG_3$ isotype amounts induced by the oligosaccharide conjugates was also more (13.11 µg/ml= oligosaccharide-conjugate; 9.84 µg/ml=polysaccharide-conjugate; 3.81 µg/ml=polysaccharide alone).

Example 8

Bactericidal and Opsonization Assays to Measure Immunoprotective Antibodies Elicited by Conjugates The basic bactericidal and opsonization assays used are as follows:

Bactericidal Assay

1. Streak a blood agar plate with desired gram negative bacteria procured from the American Type Culture Collection. Incubate at 37° C., overnight.
2. Next day, pick an isolated colony and inoculate it in 1.0 ml of Todd-Hewitt Broth (THB)+Yeast Extraction (YE) media in a sterile test tube. Incubate at 37° C. overnight.
3. On the following day, measure O.D. of inoculated bacteria at 420 nm wavelength. Use THB+YE media as blank.
4. To a sterile flat bottom 96-well plate, add a sterile 2.5 mm glass bead in each well.
5. To each well, add:
   a. 5 µl of bacteria.

b. 10 μl of mouse serum to be tested. Incubate at 37° C. for 1 hour.

Note: Step #5 and #6 are done in triplicate

6. After 1 hour incubation, prepare 1:20 dilution of exogenous complement e.g. (Low Tox Rabbit Complement, Cedarlane) sterilely in THB+YE. Add 50 μl/well. Incubate at 37° C. for 1 hour.
7. After complement incubation, 50 μl aliquot is plated out on blood agar plates using a glass spreader.
8. Wrap all agar plates in plastic bags and incubate at 37° C. for 12 hours.
9. Next day, count plaque forming colonies.

Opsonization Assay

1. Streak a blood agar plate with desired gram negative or positive bacteria (procured from the American Type Culture Collection). Incubate at 37° overnight.
2. Next day, pick an isolated colony and mix it with 1.0 ml of THB+YE media in sterile test tube. Incubate at 37° C. overnight.
3. The next day, prepare 100 U/ml of sterile heparin.
4. I.V. inject 100 μl of sterile heparin into tail of each mouse (5–10 mice). After 10 minutes, bleed mice retro-orbitally into a sterile tube.
5. Measure O.D. of bacteria at 420 nm wavelength. Use THB+YE media as blank. (Use spectrophotometer 4040 to measure O.D.)
6. To a sterile flat bottom 96 well plate with sterile 2.5 mm glass bead in each well, add:
   a. 50 μl of heparinized blood.
   b. 10 μl of serum
   c. 5 μl of bacteria
   Do this step in triplicate
7. Wrap plate in tinfoil and incubate at 37° C. incubator for one hour on a shaker (slow motion.
8. After one hour, a 50 μl aliquot is plated out on blood agar plates using a glass spreader.
9. Wrap all plates in plastic wrapper and incubate at 37° C. for 12 hours.
10. Next day, count plaque forming colonies.

Serum from mice immunized with a *S. pneumoniae* type 8 oligosaccharide conjugate was found to be immunoprotective as measured by the opsonization assay. Opsonization of *S. pneumoniae* bacteria mediated by specific anti-capsular antibodies is essential for host defense (Saunders, et al., 1993). This assay is generally considered a reliable indication of immunoprotective capability in vivo. Results from assays show that antibodies to the 8 oligo-conjugate greatly reduce growth of colony forming units of *S. pneumoniae* serotype 8 on blood agar plates (Table 22). This reduction was specific, as colony growth of serotypes 3 and 6B (used as specificity controls) were not inhibited. Immunization with the unconjugated oligosaccharide or polysaccharide (which is used in the commercially available pneumoniae vaccine) elicited no protection. Protection elicited with the polysaccharide-conjugate was much less (39% reduction) than the protection elicited with the oligosaccharide conjugate (98% reduction). These results demonstrate that our 8 oligo-tetanus toxoid conjugate elicits high levels of immunoprotective antibodies against the serotype 8 *S. pneumoniae* pathogen. The level of immunoprotective antibody elicited by poly-conjugates was marginal.

As well, the 8-oligo conjugate could elicit an immunoprotective antibody response in mice previously administered the whole polysaccharide alone. Mice injected with 2 doses of 8-polysaccharide followed by a tertiary oligo-conjugate injection had immunoprotective antibodies in their serum (70% colony reduction in opsonization assay). As in previous experiments, mice receiving 3 injections of polysaccharide elicited no significant amount of protective antibody. Oligosaccharide of specific serotypes coupled to a carrier protein may be beneficial as a booster to augment the immunoprotection of high risk groups, non-responsive or only marginally responsive to the current 23-valent polysaccharide vaccine.

We have performed an immunogenicity study with di-hapten 3 oligo/8 oligo-tetanus toxoid conjugates. Oligosaccharides of both serotypes were prepared by TFA hydrolysis. Mice injected with this multi-hapten conjugate elicited immunoprotective antibodies to the 3 and 8 serotypes (96–99% colony reduction—Table 23). A 3/8-polysaccharide conjugate elicited little immunoprotective antibody (10–12%). The mono-hapten 3 oligo-tetanus toxoid conjugate used in this study was not prepared with oligosaccharides that had been determined to have immunogenic epitopes by inhibition ELISA and was not capable of eliciting an immunoprotective response. The mechanism which allows the immune system to respond to epitopes on the 3 oligosaccharide in the di-hapten form is, of course, speculative. However, we suggest that the 8 oligosaccharides stimulate clones of cell (i.e. accessory or helper cells) which can augment the response to the epitopes on the serotype 3 oligosaccharide.

We have discovered that the 8 oligosaccharide structure has adjuvant or adjuvant "like" activity. The relatively simple repeating unit structure of the 8-oligosaccharide (β-glucose (1→4), β-Glucose (1→4)α-galactose (1→4) α gluconic acid) may specifically or non-specifically stimulate/activate immune cells or induce receptors or factors to enhance a humoral/cellular response to non-immunogenic or weakly immunogenic polysaccharides/oligosaccharides. Serotype 8 oligosaccharides has adjuvant activity in conjugate form or as an admixture to the vaccine formulation.

Opsonization results of a 14-oligosaccharide-TT conjugate (0.1M TFA preparation—Table 24) show good bacterial colony reduction of the 14 serotype (76%). The 14-oligo-TT 0.5M TFA preparation elicited less immunoprotective antibody (54% reduction). The serums from the polysaccharide-TT conjugate, the polysaccharide alone and the tetanus toxoid injected mice showed greatly reduced inhibition capacity (18, 2 and 15% respectively). Serum from control mice (0.9 NaCl injected and NMS) showed no reductive capacity.

Di-hapten-oligosaccharide conjugates also elicited antibody with opsonic activity. A serum to a 8:14-oligo-TT conjugate reduced serotype 14 colony forming units by 65% (Table 25). This di-hapten conjugate was as immunogenic as the mono-hapten 14-conjugate (reduction of CFU=68%). Serum from mice immunized with the polysaccharide-conjugate marginally reduced CFU's by 37%.

Example 9

Circumvention of Carrier Suppression and Reduction of Antigenic Competition

Reduced responses due to antigenic competition when multiple antigens are injected has been reported in the literature under some conditions. Results obtained from immunization schedules A and D (Table 26) will be used to determine if the response to each component of our multi-hapten conjugate is equal to the response elicited by the single mono-hapten conjugates.

The unit mass of carbohydrate antigen of our mono- and multi-hapten conjugates will be equivalent (i.e., 1:2 CHO:protein ratio for EDC conjugates). The design of our multi-hapten conjugates using reduced antigen load will minimize the potential for developing antigenic competition.

Schedules B and E will determine if a primary injection with the conjugate is sufficient to educate the immune system to elicit a T dependent response when boosted with uncoupled polysaccharide(s).

Schedules C and F will establish the capability of our conjugates to enhance immunoprotective antibody responses in mice previously primed with polysaccharide(s) alone. If so, a multi-hapten pneumoniae vaccine containing oligosaccharides of 3 to 4 serotypes may be very useful to augment the response to Pneumovax® 23 in high risk patients.

Groups of mice will be injected by 3 doses (1°, 2°, 3°) of tetanus toxoid (titers to tetanus toxoid to be confirmed by ELISA) followed by 3 injections of various *S. pneumoniae* oligo or poly-TT conjugates as in G (Table 26).

In all studies, conjugates will be administered orally and by subcutaneous injection.

The conjugates of the present invention will stimulate immune responses in infants, in children with immature immune systems and in the immunosuppressed. As models for these situations, we will determine the immunopotentiating efficacy of our conjugates in young mice, in SCID and nude mice. As described above, these mice will also be pre-sensitized with tetanus toxoid prior to multi-conjugate inoculation to study the carrier suppression phenomenon.

Modification of the above-described modes of carrying out the various embodiments of this invention will be apparent to those skilled in the art following the teachings of this invention as set forth herein. The examples described above are not limiting, but are merely exemplary of this invention, the scope of which is defined by the following claims.

TABLE 1

Typical Immunization Schedule for Conjugate Vaccines

| Day of Administration | Day of Bleed | Conjugate* |
|---|---|---|
| 0 | 17 | PSC-TT (A-123) |
| 7 | 38 | |
| 28 | | |
| 0 | 17 | PSC (A-123) |
| 7 | 38 | |
| 28 | | |
| 0 | 17 | OSC-TT (A-124) |
| 7 | 38 | |
| 28 | | |
| 0 | 17 | OSC (A-124) |
| 7 | 38 | |
| 28 | | |
| 0 | 17 | TT |
| 7 | 38 | |
| 28 | | |
| 0 | 17 | 0.9% NaCl |
| 7 | 38 | |
| 28 | | |
| N/A | Normal Mice | No Injection |

*Groups of 5 mice received subcutaneous injections of 0.1, 0.5, 1.0, 2.5 or 5.0 μg conjugate in 200 μl 0.9% NaCl (100 μl injection in each flank). PSC-TT (A-123) is Polysaccharide-Tetanus Toxoid Conjugate (Lot # A 123). OSC-TT (A-124) is Oligosaccharide (4–8 repeat units)-Tetanus Toxoid Conjugate (Lot # A-124). PSC (A-123) is Polysaccharide (Lot # A-123). OSC (A-124) is Oligosaccharide (4–8 repeat units) (Lot # A-124). TT is Tetanus Toxoid.

TABLE 2

Mean Levels of Mouse Serum Antibodies to Various Serotype 8 *S. Pneumoniae* Conjugates (Post-Tertiary Immunization)

| Antiserum to: | Immunoglobulin Isotype Class (μg/ml) | | | | | |
|---|---|---|---|---|---|---|
| | IgA | IgG$_1$ | IgG$_{2a}$ | IgG$_{2b}$ | IgG$_3$ | IgM |
| 8-Oligosaccharide-Tetanus Toxoid Conjugates | 3.3 | 2.7 | 0.08 | 0.07 | 1.7 | 8.4 |
| Unconjugated 8-Oligosaccharide | 0.3 | 0.05 | 0.02 | 0.02 | 0.8 | 0.8 |
| 8-Polysaccharide-Tetanus Toxoid Conjugates | 10.8 | 0.13 | 0.07 | 0.07 | 1.75 | 14.6 |
| Unconjugated 8-Polysaccharide | 5.75 | 0.08 | 0.05 | 0.06 | 2.75 | 10.4 |

TABLE 3

INHIBITION ELISA USING TYPE-8 OLIGOSACCHARIDES

| Inhibiting Antigen Concentration | O.D. 405 nm Repeat Units Prepared by 0.5M TFA, 100° C., 20 min | | | | | | | | |
|---|---|---|---|---|---|---|---|---|---|
| (ug) | 8-PS | 1 R.U. | 2 R.U. | 3 R.U. | 4 R.U. | 5 R.U. | 6 R.U. | 7 R.U | 8+ R.U. |
| 25.0 | 0.013 | 2.575 | 1.015 | 0.680 | 0.733 | 0.698 | 0.564 | 0.489 | 0.177 |
| 12.5 | 0.011 | 2.583 | 1.610 | 1.109 | 1.190 | 0.974 | 1.008 | 0.827 | 0.427 |
| 6.25 | 0.031 | 2.542 | 2.042 | 1.751 | 1.878 | 1.395 | 1.303 | 1.243 | 0.783 |
| 3.13 | 0.105 | 2.591 | 2.359 | 2.127 | 2.456 | 1.845 | 1.827 | 1.628 | 1.204 |
| 1.57 | 0.228 | 2.585 | 2.566 | 2.264 | 2.748 | 2.282 | 2.234 | 1.944 | 1.744 |
| 0.781 | 0.468 | 2.602 | 2.643 | 2.313 | 2.761 | 2.597 | 2.531 | 2.219 | 2.014 |
| 0.391 | 0.821 | 2.919 | 2.829 | 2.549 | 3.000 | 2.814 | 2.837 | 2.318 | 2.865 |

TABLE 4

INHIBITION ELISA USING TYPE-6B OLIGOSACCHARIDES

| | O.D. 405 nm | |
|---|---|---|
| Inhibiting Antigen Concentration (ug) | 6B-PS | 6B (0.01M Acetic Acid, 100° C., 30 h) |
| 25.0 | 0.018 | 0.300 |
| 12.5 | 0.023 | 0.502 |
| 6.25 | 0.025 | 0.776 |
| 3.13 | 0.054 | 0.952 |
| 1.57 | 0.109 | 1.090 |
| 0.781 | 0.207 | 1.192 |
| 0.391 | 0.331 | 1.266 |

TABLE 5

INHIBITION ELISA USING DIFFERENT TFA PREPARATIONS OF TYPE-6B OLIGOSACCHARIDES

| | O.D. 405 nm | | | |
|---|---|---|---|---|
| Inhibiting Antigen Concentration (ug) | 6B-PS | 6B (0.5M TFA, 70° C., 1 h) | 6B (0.1M TFA, 70° C., 2 h) | 6B (0.1M TFA, 70° C., 4 h) |
| 25.0 | 0.016 | 0.223 | 0.211 | 1.897 |
| 12.5 | 0.017 | 0.281 | 0.372 | 2.417 |
| 6.25 | 0.069 | 0.717 | 0.702 | 2.276 |
| 3.13 | 0.370 | 1.096 | 1.216 | 2.674 |
| 1.57 | 0.958 | 2.411 | 1.793 | 2.673 |
| 0.781 | 0.959 | 2.595 | 2.243 | 2.817 |
| 0.391 | 1.216 | 2.540 | 2.502 | 2.563 |

TABLE 6

INHIBITION ELISA USING DIFFERENT ACETIC ACID PREPARATIONS OF TYPE-6B OLIGOSACCHARIDES

| | O.D. 405 nm | | | |
|---|---|---|---|---|
| Inhibiting Antigen Concentration (ug) | 6B-PS | 6B (2M Acetic Acid, 70° C., 2 h) | 6B (2M Acetic Acid, 70° C., 24 h) | 6B (2M Acetic Acid, 70° C., 48 h) |
| 25.0 | 0.016 | 0.341 | 1.530 | 2.452 |
| 12.5 | 0.017 | 0.631 | 1.849 | 2.534 |
| 6.25 | 0.069 | 0.982 | 2.319 | 2.613 |
| 3.13 | 0.370 | 1.504 | 2.579 | 2.716 |
| 1.57 | 0.958 | 2.034 | 2.748 | 2.807 |
| 0.781 | 0.959 | 2.473 | 2.751 | 2.732 |
| 0.391 | 1.216 | 2.533 | 2.597 | 2.626 |

TABLE 7

INHIBITION ELISA USING TYPE-6B OLIGOSACCHARIDES

| | O.D. 405 nm | |
|---|---|---|
| Inhibiting Antigen Concentration (ug) | 6B-PS | 6B (0.05M TFA, 70° C., 1.5 h) | 6B (0.05M TFA, 70° C., 3 h) |
| 25.0 | 0.100 | 0.297 | 0.594 |
| 12.5 | 0.140 | 0.485 | 0.916 |
| 6.25 | 0.215 | 0.816 | 1.371 |
| 3.13 | 0.396 | 1.180 | 1.852 |
| 1.57 | 0.563 | 1.702 | 2.195 |
| 0.781 | 1.060 | 2.286 | 2.644 |
| 0.391 | 1.616 | 2.515 | 2.551 |

TABLE 8

INHIBITION ELISA USING TYPE-14 OLIGOSACCHARIDES

| | O.D. 405 nm | | |
|---|---|---|---|
| Inhibiting Antigen Concentration (ug) | 14-PS | 14 (0.1M TFA, 70° C., 3 h) | 14 (0.5M TFA, 70° C., 7 h) |
| 25.0 | 0.020 | 0.072 | 0.201 |
| 12.5 | 0.022 | 0.229 | 0.339 |
| 6.25 | 0.022 | 0.362 | 0.745 |
| 3.13 | 0.065 | 0.631 | 1.032 |
| 1.57 | 0.161 | 1.028 | 1.341 |
| 0.781 | 0.299 | 1.277 | 1.614 |
| 0.391 | 0.644 | 1.691 | 1.714 |

TABLE 9

INHIBITION ELISA USING TYPE-14 OLIGOSACCHARIDES

| | O.D. 405 nm Repeat Units Prepared by 0.5M TFA, 100° C., 15 min | | |
|---|---|---|---|
| Inhibiting Antigen Concentration (ug) | 3 R.U. | 4 R.U. | 8 R.U. |
| 25.0 | 2.011 | 0.596 | 0.337 |
| 12.5 | 1.966 | 1.078 | 0.517 |
| 6.25 | 1.936 | 1.425 | 0.712 |
| 3.13 | 1.891 | 1.620 | 0.924 |
| 1.57 | 2.021 | 1.889 | 1.242 |
| 0.781 | 2.055 | 1.923 | 1.595 |
| 0.391 | 2.089 | 1.877 | 1.727 |

TABLE 10

INHIBITION ELISA USING TYPE-14 OLIGOSACCHARIDES

| | O.D. 405 nm | | | |
|---|---|---|---|---|
| Inhibiting Antigen Concentration (ug) | 14-PS | 14 (0.01M TFA 70° C., 7 h) | 14 (0.05M TFA 70° C., 7 h) | 14 (0.05M TFA 70° C., 24 h) |
| 25.0 | 0.038 | 0.075 | 0.163 | 0.610 |
| 12.5 | 0.055 | 0.110 | 0.283 | 0.986 |
| 6.25 | 0.093 | 0.191 | 0.503 | 1.406 |
| 3.13 | 0.197 | 0.318 | 0.857 | 2.225 |
| 1.57 | 0.330 | 0.528 | 1.367 | 2.562 |
| 0.781 | 0.623 | 0.945 | 2.095 | 2.622 |
| 0.391 | 1.053 | 1.462 | 2.429 | 2.569 |

TABLE 11

INHIBITION ELISA USING TYPE-19F OLIGOSACCHARIDES

| | | O.D. 405 nm | |
|---|---|---|---|
| Inhibiting Antigen Concentration (ug) | 19F-PS | 19F (0.2M HCl, no heat, 3 h) | 19F (0.2M HCl, 70° C., 3 h) |
| 25.0 | 0.347 | 2.335 | 0.253 |
| 12.5 | 0.380 | 2.926 | 0.328 |
| 6.25 | 0.460 | 3.286 | 0.495 |
| 3.13 | 0.669 | 3.415 | 0.691 |
| 1.57 | 0.805 | 3.405 | 1.064 |
| 0.781 | 1.000 | 3.491 | 1.414 |
| 0.391 | 1.508 | 3.549 | 1.827 |

TABLE 12

INHIBITION ELISA USING TYPE-23F OLIGOSACCHARIDES

| | | O.D. 405 nm | |
|---|---|---|---|
| Inhibiting Antigen Concentration (ug) | 23F-PS | 23F (0.5M TFA, 70° C., 1 h) | 23F (0.25M TFA, 70° C., 3 h) |
| 25.0 | 0.033 | 0.385 | 0.435 |
| 12.5 | 0.033 | 0.586 | 0.592 |
| 6.25 | 0.027 | 0.686 | 0.743 |
| 3.13 | 0.037 | 0.832 | 0.870 |
| 1.57 | 0.062 | 0.952 | 0.933 |
| 0.781 | 0.128 | 1.085 | 1.029 |
| 0.391 | 0.240 | 1.155 | 1.099 |

TABLE 13

INHIBITION ELISA USING TYPE-23F OLIGOSACCHARIDES

| | | O.D. 405 nm | |
|---|---|---|---|
| Inhibiting Antigen Concentration (ug) | 23F-PS | 23F (0.1M TFA, 70° C., 3 h) | 23F (0.1M TFA, 70° C., 5 h) |
| 25.0 | 0.487 | 0.187 | 2.107 |
| 12.5 | 0.364 | 0.261 | 2.517 |
| 6.25 | 0.355 | 0.339 | 2.623 |
| 3.13 | 0.341 | 0.545 | 3.009 |
| 1.57 | 0.358 | 0.770 | 2.689 |
| 0.781 | 0.401 | 0.998 | 2.624 |
| 0.391 | 0.432 | 1.366 | 2.887 |

TABLE 14

INHIBITION ELISA USING TYPE-23F OLIGOSACCHARIDES

| | | O.D. 405 nm | | |
|---|---|---|---|---|
| Inhibiting Antigen Concentration (ug) | 23F-PS | 23F (0.5M TFA, 70° C., 1 h) | 23F (0.5M TFA, 70° C., 15 min) | 23F (5M Acetic Acid, 70° C., 5 h) | 23F (2M Acetic Acid, 70° C., 24 h) |
| 25.0 | 0.127 | 0.309 | 0.159 | 0.160 | 0.241 |
| 12.5 | 0.111 | 0.529 | 0.149 | 0.144 | 0.405 |
| 6.25 | 0.118 | 0.923 | 0.179 | 0.243 | 0.750 |
| 3.13 | 0.148 | 1.480 | 0.242 | 0.410 | 1.172 |
| 1.57 | 0.288 | 2.118 | 0.430 | 0.852 | 1.662 |
| 0.781 | 0.480 | 2.534 | 0.712 | 1.345 | 2.361 |
| 0.391 | 0.940 | 2.557 | 1.218 | 1.909 | 2.430 |

TABLE 15

INHIBITION ELISA USING *N. meningitidis*-C POLYSACCHARIDE

| | | O.D. 405 nm | |
|---|---|---|---|
| Inhibiting Antigen Concentration (ug) | N. meng-CPS | N. meng-C (0.1M NaOAc, 50° C., 6 h) | N. meng-C (1M NaOAc, 50° C., 6 h) |
| 25.0 | 0.304 | 0.269 | 0.269 |
| 12.5 | 0.240 | 0.245 | 0.258 |
| 6.25 | 0.369 | 0.406 | 0.412 |
| 3.13 | 0.836 | 1.088 | 1.151 |
| 1.57 | 2.402 | 2.593 | 2.512 |
| 0.781 | 2.679 | 2.839 | 2.749 |
| 0.391 | 2.434 | 2.448 | 2.504 |

TABLE 16

INHIBITION ELISA USING TYPE-6B CONJUGATES

| Inhibiting Antigen Concentration (ug) | O.D. 405 nm | | | |
|---|---|---|---|---|
| | 6B-PS | 6B:8-TT | 6B-OS | T.T. |
| 25.0 | 0.019 | 0.070 | 0.037 | 2.314 |
| 12.5 | 0.022 | 0.117 | 0.046 | 2.289 |
| 6.25 | 0.033 | 0.205 | 0.081 | 2.209 |
| 3.13 | 0.058 | 0.339 | 0.145 | 2.173 |
| 1.57 | 0.127 | 0.533 | 0.287 | 2.208 |
| 0.781 | 0.248 | 0.816 | 0.534 | 2.237 |
| 0.391 | 0.435 | 1.234 | 0.856 | 2.249 |

TABLE 17

INHIBITION ELISA USING TYPE-14 CONJUGATES

| Inhibiting Antigen Concentration (ug) | O.D. 405 nm | | | |
|---|---|---|---|---|
| | 14-PS | 14:8-TT | 14-OS | T.T. |
| 25.0 | 0.004 | 0.029 | 0.026 | 0.216 |
| 12.5 | 0.006 | 0.043 | 0.037 | 0.510 |
| 6.25 | 0.017 | 0.075 | 0.068 | 0.769 |
| 3.13 | 0.043 | 0.141 | 0.131 | 1.018 |
| 1.57 | 0.078 | 0.258 | 0.247 | 1.242 |
| 0.781 | 0.160 | 0.447 | 0.400 | 1.362 |
| 0.391 | 0.299 | 0.669 | 0.655 | 1.475 |

TABLE 18

INHIBITION ELISA USING TYPE-23F CONJUGATES

| Inhibiting Antigen Concentration (ug) | O.D. 405 nm | | | | | |
|---|---|---|---|---|---|---|
| | 23F-PS-TT | 23F-TT (F:27-47) | 23F-TT(F:32-51) | 23F-TT (F:32-65) | 23F-TT(F:31-51) | T.T. |
| 25.0 | 0.027 | 0.348 | 0.235 | 0.397 | 0.053 | 1.073 |
| 12.5 | 0.038 | 0.433 | 0.390 | 0.463 | 0.093 | 1.017 |
| 6.25 | 0.055 | 0.556 | 0.547 | 0.604 | 0.161 | 1.094 |
| 3.13 | 0.104 | 0.659 | 0.665 | 0.698 | 0.255 | 1.097 |
| 1.57 | 0.189 | 0.806 | 0.823 | 0.769 | 0.371 | 1.098 |
| 0.781 | 0.215 | 0.944 | 0.861 | 0.954 | 0.548 | 1.085 |
| 0.391 | 0.412 | 1.029 | 1.017 | 0.978 | 0.696 | 1.089 |

TABLE 19

INHIBITION ELISA USING N. meningitidis-C POLYSACCHARIDE

| Inhibiting Antigen Concentration (ug) | O.D. 405 nm | | | |
|---|---|---|---|---|
| | N.meng-CPS | N.meng-CPS-TT | N.mengC-TT (F:37–49) | T.T. |
| 25.0 | 0.038 | 0.068 | 0.250 | 2.222 |
| 12.5 | 0.025 | 0.042 | 0.221 | 1.880 |
| 6.25 | 0.028 | 0.120 | 0.297 | 1.917 |
| 3.13 | 0.058 | 0.209 | 0.529 | 1.894 |
| 1.57 | 0.108 | 0.212 | 0.610 | 1.807 |
| 0.781 | 0.371 | 0.511 | 0.762 | 1.813 |
| 0.391 | 0.393 | 0.623 | 1.101 | 1.849 |

TABLE 20

Means Levels of $IgG_1$ and $IgG_3$ Antibodies To Serotype 8 S. Pneumoniae Conjugates (Post-Tertiary Immunization)

| 1' Immunization at: | Immunoglobulin Isotype (µg/ml) | |
|---|---|---|
| | $IgG_1$ | $IgG_3$ |
| 3 weeks of age | | |
| 8-O-TT | 0.273 | 0.468 |
| 8-P-TT | 0.036 | 0.213 |
| 8-P | 0.052 | 3.18 |
| TT | 0.034 | — |
| 8 weeks of age | | |
| 8-O-TT | 0.700 | 1.96 |
| 8-P-TT | 0.159 | 2.89 |
| 8-P | 0.007 | 2.17 |
| TT | 0.003 | 0.74 |
| 8 weeks of age + FCA | | |
| 8-O-TT | 1.22 | 1.74 |
| 8-P-TT | — | 3.73 |
| 8-P | 0.055 | 5.06 |
| TT | — | 0.295 |

TABLE 21

Mean Levels of Mouse Serum Antibodies to Various Serotype 14 S. pneumoniae Conjugates (Post-Tertiary Immunization) Immunoglobulin Isotype µg/ml

| Antiserum to: | IgM | $IgG_1$ | $IgG_{2a}$ | $IgG_{2b}$ | $IgG_3$ | IgA |
|---|---|---|---|---|---|---|
| 14-oligo-TT (0.1 M TFA) | 6.50 | 50.99 | 0.178 | 0.158 | 37.65 | 0.078 |
| 1 µg 14-oligo-TT (0.5 M TFA peak 4 & 5) | 2.8 | — | 0.009 | 0.018 | 1.51 | — |

TABLE 21-continued

Mean Levels of Mouse Serum Antibodies to Various Serotype 14 S. pneumoniae Conjugates (Post-Tertiary Immunization) Immunoglobulin Isotype µg/ml

| Antiserum to: | IgM | $IgG_1$ | $IgG_{2a}$ | $IgG_{2b}$ | $IgG_3$ | IgA |
|---|---|---|---|---|---|---|
| 1µ 14-oligo-TT (0.5 M TFA peak 7 & 8) | 3.39 | 12.35 | 0.155 | 0.143 | 9.32 | 0.020 |
| 1 µg 14-poly-TT | 5.11 | 15.25 | 0.038 | 0.053 | 8.95 | 0.001 |
| 1 µg 14-poly | 4.70 | — | 0.008 | 0.031 | 9.20 | 0.077 |
| 1µ T.T. | 3.37 | — | 0.024 | 0.060 | 8.36 | 0.031 |

TABLE 22

Opsonization Results Testing Antiserum to Serotype 8 S. pneumoniae Conjugate % Reduction of Colony Forming Units (CFU)

| Antiserum to: | Type 8 |
|---|---|
| 8-Oligosaccharide Tetanus Toxoid Conjugate | 98 |
| Unconjugated 8-Oligosaccharide | 10 |
| 8-Polysaccharide Tetanus Toxoid Conjugate | 39 |
| Unconjugated 8-Polysaccharide | 11 |

TABLE 23

Opsonization Results Testing Antiserum to Serotype 3 and 8 S. Pneumoniae Conjugates % Reduction of CFU

| Anitiserum to: | Type 3 | Type 6B | Type 8 |
|---|---|---|---|
| 3/8-Oligosaccharide Tetanus Toxoid Conjugate | 96 | 0 | 99 |
| 3/8-Polysaccharide Tetanus Toxoid Conjugate | 10 | 0 | 12 |
| PBS control | 0 | 0 | 0 |

TABLE 24

Opsonization Results Testing Antiserum to Serotype 14 S. Pneumoniae Conjugates % Reduction of CFU

| Antiserum to: | Type 14 |
|---|---|
| 14-O-TT (0.1 M TFA) | 76 |
| 14-O-TT-10.5 M TFA Peaks 7 & 8) | 54 |
| 14-Poly-TT | 18 |
| 14-Polysaccharide | 2 |
| Tetanus Toxoid | 15 |
| 0.9% NaCl | 0 |
| NMS | 0 |

TABLE 25

Opsonization Results Testing Antiserum to
A Di-Hapten S. pneumoniae Conjugate
% Reduction of CFU

| Antiserum To: | Type 14 |
|---|---|
| 14-O-TT | 68 |
| 8:14-O-TT | 65 |
| 14-P-TT | 37 |
| Tetanus Toxoid | 0 |
| 0.9% NaCl | 0 |
| NMS | 0 |

TABLE 26

IMMUNIZATION REGIMES

| | |
|---|---|
| A: | 1˚ Mono-hapten-oligosaccharide conjugate |
| | 2˚ Mono-hapten-oligosaccharide conjugate |
| | 3˚ Mono-hapten-oligosaccharide conjugate |
| B: | 1˚ Mono-hapten-oligosaccharide conjugate |
| | 2˚ Uncoupled polysaccharide |
| | 3˚ Uncoupled polysaccharide |
| C: | 1˚ Uncoupled polysaccharides |
| | 2˚ Mono-hapten-oligosaccharide conjugate |
| | 3˚ Mono-hapten-oligosaccharide conjugate |
| D: | 1˚ Multi-hapten-oligosaccharide conjugate |
| | 2˚ Multi-hapten-oligosaccharide conjugate |
| | 3˚ Multi-hapten-oligosaccharide conjugate |
| E: | 1˚ Multi-hapten-oligosaccharide conjugate |
| | 2˚ Uncoupled polysaccharides |
| | 3˚ Uncoupled polysaccharides |
| F: | 1˚ Uncoupled polysaccharides |
| | 2˚ Multi-hapten-oligosaccharide conjugate |
| | 3˚ Multi-hapten-oligosaccharide conjugate |
| G: | 1˚ Tetanus toxoid |
| | 2˚ Tetanus toxoid |
| | 3˚ Tetanus toxoid |
| | 4˚ Mono- or multi-hapten oligosaccharide conjugates |
| | 5˚ Mono- or multi-hapten oligosaccharide conjugates |
| | 6˚ Mono- or multi-hapten oligosaccharide conjugates |

What is claimed is:

1. A method of preparing a composition comprising a conjugate, wherein each conjugate consists essentially of at least one oligosaccharide hapten which retains at least one immunogenic epitope wherein each said oligosaccharide hapten has a multiple of repeat subunits and a carrier which elicits a thymus dependent immune response in a subject, wherein said hapten is covalently coupled directly to said carrier and wherein said hapten-carrier conjugate is protectively immunogenic, which method comprises:

a) cleaving a bacterial or viral polysaccharide antigen which produces a thymus independent immunogenic response in a subject into oligosaccharide repeat units wherein the immunogenic epitopes on at least one of the resulting oligosaccharide repeat units is preserved;

b) separating the resulting oligosaccharide repeat units into oligosaccharide haptens having a multiple of repeat subunits;

c) selecting those oligosaccharide haptens which retain at least one immunogenic epitope as oligosaccharide haptens;

d) activating one or more of the oligosaccharide haptens selected in step c); and e) directly coupling the activated oligosaccharide haptens to a carrier which elicits a thymus dependent immune response in a subject, wherein the resulting composition is protectively immunogenic.

2. The method of claim 1 wherein said cleavage is performed using acid hydrolysis.

3. The method of claim 1 wherein said activation is acidification on a cation column.

4. The method of claim 1 wherein said coupling is performed using EDC or periodate.

5. The method of claim 1 wherein said coupling provides a predictable ratio of hapten to carrier.

6. The method of claim 1 wherein steps a) through d) are repeated using at least one additional bacterial or viral polysaccharide to result in a di- or multi-valent conjugate.

7. The method of claim 6 wherein said bacterial polysaccharides are selected from the group consisting of capsular polysaccharides of S. pneumococcus serotypes 1, 2, 3, 4, 5, 6B, 7, 7F, 8, 9N, 9V, 10A, 11A, 12, 12F, 14, 15B, 17F, 18C, 19F, 19A, 20, 22, 23F and 33F.

* * * * *